(12) United States Patent
Shibata et al.

(10) Patent No.: US 6,872,729 B2
(45) Date of Patent: Mar. 29, 2005

(54) PYRIMIDINYLBENZIMIDAZOLE AND TRIAZINYLBENZIMIDAZOLE DERIVATIVES AND AGRICULTURAL/HORTICULTURAL FUNGICIDES

(75) Inventors: Masaru Shibata, Shizouka (JP); Kiyoshi Kawai, Shizouka (JP); Takechi Makihara, Shizouka (JP); Norihisa Yonekura, Shizouka (JP); Takehiro Kawashima, Shizouka (JP); Junetsu Sakai, Shizouka (JP); Norimichi Muramatsu, Shizouka (JP)

(73) Assignees: Kumiai Chemical Industry Co., Ltd., Tokyo (JP); Ihara Chemical Industry Co., Ltd., Tokyo (JP)

( * ) Notice: Subject to any disclaimer, the term of this patent is extended or adjusted under 35 U.S.C. 154(b) by 133 days.

(21) Appl. No.: 10/383,693

(22) Filed: Mar. 10, 2003

(65) Prior Publication Data
US 2004/0023966 A1 Feb. 5, 2004

Related U.S. Application Data

(62) Division of application No. 09/830,578, filed as application No. PCT/JP99/06364 on Nov. 15, 1999, now Pat. No. 6,576,631.

(30) Foreign Application Priority Data

Nov. 17, 1998 (JP) .......................................... 10/343614
Feb. 18, 1999 (JP) ............................................ 11/39566

(51) Int. Cl.[7] ...................... C07D 239/42; A01N 43/54
(52) U.S. Cl. ...................... 514/272; 514/273; 514/241; 544/320; 544/321; 544/330; 544/331; 544/206; 544/207; 544/209; 544/219
(58) Field of Search ................. 544/320, 321, 544/330, 332, 331; 514/272, 273

(56) References Cited

U.S. PATENT DOCUMENTS

| | | | |
|---|---|---|---|
| 4,659,363 A | 4/1987 | Hubele et al. | 544/326 |
| 4,694,009 A | 9/1987 | Hubele et al. | 544/321 |
| 4,698,091 A | 10/1987 | Brunner et al. | 544/334 |
| 4,802,909 A | 2/1989 | Rempfler et al. | 544/323 |
| 4,973,690 A | 11/1990 | Rempfler et al. | 544/279 |
| 4,999,046 A | 3/1991 | Rempfler | 544/322 |
| 5,179,098 A | 1/1993 | Clough et al. | 544/300 |
| 5,714,509 A | 2/1998 | Luo et al. | 514/415 |
| 5,739,129 A | 4/1998 | Aquino et al. | 514/221 |

FOREIGN PATENT DOCUMENTS

| | | |
|---|---|---|
| DE | 151 404 | 10/1981 |
| EP | 0 945 443 | 9/1999 |
| EP | 1 020 462 | 7/2000 |
| FR | 1 476 529 | 4/1967 |
| JP | 56-65804 | 6/1981 |
| WO | WO 99/05138 | 2/1999 |
| WO | WO-01 25220 | 4/2001 |

OTHER PUBLICATIONS

Patent Abstracts of Hungary, HU 217084, Nov. 19, 1999.
Patent Abstracts of Hungary, HU 195962, Aug. 29, 1988.
L. Forlani, Journal of Heterocyclic Chemistry, vol. 29, No. 6, pp. 1461–1464, "Tautomerism of Some Amino Aza–Containing Heterocycles," Oct.–Nov. 1992.
Y. Obara et al. Nippon Nogeikagaku Kaisha, vol. 55, No. 12, pp. 1205–1212, "Studies on the Biological Activity of Heterocyclic Copmpounds, Part IV, on the Blinding Acrivities and Acute Oral Toxicities of Aminobenzenes, Pyrimidines, Purines, Amino–S–Triazines and Their Related Compounds an Baby Chicks," 1981.
K. Nakamura et al., Bulletin of the Chemical Society of Japan, vol. 45, No. 10, pp. 3140–3147, "The N1–N2 Migration of the s–Triazynyl Group of 4–Substituted N1,N1–Bis–(s–Triazinyl)–o–Phenylenediamines," 1972.
N. Nohara et al., Chemical Abstrats, vol. 73, No. 35337z, p. 327, "Derivatives of Ditriazinylamine and Tritriazinylamine," 1970.

Primary Examiner—Richard L. Raymond
Assistant Examiner—Venkataraman Balasubramanian
(74) Attorney, Agent, or Firm—Oblon, Spivak, McClelland, Maier & Neustadt, P.C.

(57) ABSTRACT

A pyrimidinylbenzimidazole or triazinylbenzimidazole derivative represented by the general formula (I):

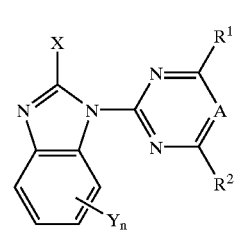

wherein A is N or $CR^3$, and $R^1$, $R^2$, $R^3$, X, Y and n are as defined in the disclosure.

5 Claims, No Drawings

PYRIMIDINYLBENZIMIDAZOLE AND TRIAZINYLBENZIMIDAZOLE DERIVATIVES AND AGRICULTURAL/HORTICULTURAL FUNGICIDES

This application is a Division of application Ser. No. 09/830,578 filed on May 8, 2001 now U.S. Pat. No. 6,576,631, which was filed as International Application No. PCT/JP99/06364 filed Nov. 15, 1999.

TECHNICAL FIELD

The present invention relates to novel pyrimidinylbenzimidazole and triazinylbenzimidazole derivatives and agricultural/horticultural fungicides containing said derivatives as the active ingredients.

BACKGROUND ART

As compounds related to the pyrimidinylbenzimidazole derivatives of the present invention, 4-aminopyrimidine derivatives disclosed as pharmaceuticals in U.S. Pat. No. 5,525,604 and European Patent No. 640,599 and pyrimidine derivatives disclosed as herbicides in International Publication No. WO94/17059, are mentioned, but no disclosure regarding agricultural/horticultural fungicides has been made. French Patent No. 1,476,529 discloses benzimidazolyl sulfonamide derivatives having insecticidal and fungicidal activities, but no disclosure regarding the present compounds has been made. Further, as compounds related to the triazinylbenzimidazole derivatives of the present invention, triazine derivatives disclosed in JP-A-47-36837, JP-A-49-17677 and Kogyo Kagaku Zassi (Journal of Industrial Chemistry) vol 73, No. 5, p1000 (1970) as coloring agents for textile goods, may be mentioned, but no disclosure regarding agricultural/horticultural fungicides has been made. Further, anilinopyrimidine derivatives as production intermediates therefor have not been known.

The present invention provides novel pyrimidinylbenzimidazole and triazinylbenzimidazole derivatives and agricultural/horticultural fungicides containing them as the active ingredients.

The present inventors have conducted extensive studies to create novel agricultural/horticultural fungicides and as a result, found that the pyrimidinylbenzimidazole and triazinylbenzimidazole derivatives of the present invention (hereinafter referred to as compounds of the present invention) are novel compounds which are not disclosed in any literatures and have outstanding effects as agricultural/horticultural fungicides, and the present invention has been accomplished.

DISCLOSURE OF THE INVENTION

Namely, the present invention resides in a pyrimidinylbenzimidazole or triazinylbenzimidazole derivative represented by the general formula [I]:

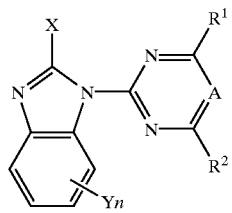

[I]

{wherein A is N or $CR^3$, each of $R^1$ and $R^2$ which are independent of each other, is a hydrogen atom, a halogen atom, a $(C_1-C_6)$ alkyl group, a $(C_2-C_6)$ alkenyl group, a $(C_2-C_6)$ alkynyl group, a $(C_3-C_6)$ cycloalkyl group, a $(C_1-C_4)$ haloalkyl group, a $(C_1-C_6)$ alkoxy group, a $(C_2-C_6)$ alkenyloxy group, a $(C_2-C_6)$ alkynyloxy group, a $(C_3-C_6)$ cycloalkoxy group, a $(C_1-C_4)$ haloalkoxy group, a cyano $(C_1-C_4)$ alkyloxy group, a $(C_1-C_4)$ alkoxy $(C_1-C_4)$ alkyloxy group, a $(C_3-C_6)$ cycloalkyl $(C_1-C_4)$ alkoxy group, a benzyloxy group [said group may be substituted by a halogen atom, a $(C_1-C_4)$ alkyl group or a $(C_1-C_4)$ alkoxy group], a $(C_1-C_6)$ alkylthio group, a $(C_1-C_4)$ alkoxy $(C_1-C_4)$ alkyl group, a phenoxy group [said group may be substituted by a halogen atom, a $(C_1-C_4)$ alkyl group or a $(C_1-C_4)$ alkoxy group], a $(C_1-C_4)$ alkylcarbonyl group, a formyl group, a phenyl group, a di($C_1-C_4$) alkylamino group, a cyano group or a $(C_1-C_6)$ alkylsulfonyl group, $R^3$ is a hydrogen atom, a $(C_1-C_6)$ alkyl group, a $(C_1-C_6)$ alkoxy group or a halogen atom, X is a hydrogen atom, a halogen atom, a nitro group, a cyano group, a $(C_1-C_6)$ alkyl group, a $(C_2-C_6)$ alkenyl group, a $(C_2-C_6)$ alkynyl group, a $(C_3-C_6)$ cycloalkyl group, a benzyl group [said group may be substituted by a halogen atom, a $(C_1-C_4)$ alkyl group or a $(C_1-C_4)$ alkoxy group], a $(C_1-C_6)$ alkoxy group, a $(C_2-C_6)$ alkenyloxy group, a $(C_2-C_6)$ alkynyloxy group, a $(C_1-C_6)$ alkylthio group, a $(C_1-C_6)$ alkylsulfonyl group, a phenoxy group, a $(C_1-C_4)$ alkoxy $(C_1-C_4)$ alkyl group, a $(C_1-C_4)$ haloalkyl group, a $(C_1-C_4)$ haloalkoxy group, a $(C_1-C_4)$ alkylcarbonyl group, a $(C_1-C_4)$ alkoxycarbonyl group, an amino group, a mono $(C_1-C_4)$ alkylamino group, a di($C_1-C_4$) alkylamino group, an anilino group or a phenyl group [said group may be substituted by a halogen atom, a $(C_1-C_4)$ alkyl group or a $(C_1-C_4)$ alkoxy group], Y is a halogen atom, a nitro group, a cyano group, a $(C_1-C_6)$ alkyl group, a $(C_2-C_6)$ alkenyl group, a $(C_2-C_6)$ alkynyl group, a $(C_1-C_6)$ alkoxy group, a $(C_2-C_6)$ alkenyloxy group, a $(C_2-C_6)$ alkynyloxy group, a $(C_1-C_4)$ haloalkoxy group, a $(C_1-C_6)$ alkylthio group, a $(C_1-C_4)$ alkoxy $(C_1-C_4)$ alkyl group, a $(C_1-C_4)$ haloalkyl group, a $(C_1-C_4)$ alkylcarbonyl group, a $(C_1-C_4)$ alkoxycarbonyl group, a benzoyl group, an amino group, a mono $(C_1-C_4)$ alkylamino group, a di($C_1-C_4$) alkylamino group, a phenyl group [said group may be substituted by a halogen atom, a $(C_1-C_4)$ alkyl group or a $(C_1-C_4)$ alkoxy group] or a phenoxy group [said group may be substituted by a halogen atom, a $(C_1-C_4)$ alkyl group or a $(C_1-C_4)$ alkoxy group], and n is 0 or an integer of from 1 to 3}, an anilinopyrimidine or anilinotriazine derivative, as an intermediate therefor, represented by the general formula [XV]:

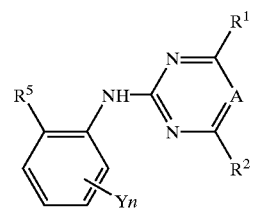

[XV]

{wherein A is N or $CR^3$, each of $R^1$ and $R^2$ which are independent of each other, is a hydrogen atom, a halogen atom, a $(C_1-C_6)$ alkyl group, a $(C_2-C_6)$ alkenyl group, a $(C_2-C_6)$ alkynyl group, a $(C_3-C_6)$ cycloalkyl group, a $(C_1-C_4)$ haloalkyl group, a $(C_1-C_6)$ alkoxy group, a $(C_2-C_6)$ alkenyloxy group, a $(C_2-C_6)$ alkynyloxy group, a $(C_3-C_6)$ cycloalkoxy group, a $(C_1-C_4)$ haloalkoxy group, a cyano $(C_1-C_4)$ alkyloxy group, a $(C_1-C_4)$ alkoxy $(C_1-C_4)$ alkyloxy group, a $(C_3-C_6)$ cycloalkyl $(C_1-C_4)$ alkoxy group, a benzyloxy group [said group may be substituted by a halogen atom, a $(C_1-C_4)$ alkyl group or a $(C_1-C_4)$ alkoxy group], a ($C_1$–$C_6$) alkylthio group, a ($C_1$–$C_4$) alkoxy ($C_1$–$C_4$) alkyl group, a phenoxy group [said group may be substituted by a halogen atom, a ($C_1$–$C_4$) alkyl group or a ($C_1$–$C_4$) alkoxy group], a ($C_1$–$C_4$) alkylcarbonyl group, a formyl group, a phenyl group, a di($C_1$–$C_4$) alkylamino group, a cyano group or a ($C_1$–$C_6$) alkylsulfonyl group, $R^3$ is a hydrogen atom, a ($C_1$–$C_6$) alkyl group, a ($C_1$–$C_6$) alkoxy group or a halogen atom, $R^5$ is an amino group, a nitro group or —NHCOX, X is a hydrogen atom, a halogen atom, a nitro group, a cyano group, a ($C_1$–$C_6$) alkyl group, a ($C_2$–$C_6$) alkenyl group, a ($C_2$–$C_6$) alkynyl group, a ($C_3$–$C_6$) cycloalkyl group, a benzyl group [said group may be substituted by a halogen atom, a ($C_1$–$C_4$) alkyl group or a ($C_1$–$C_4$) alkoxy group], a ($C_1$–$C_6$) alkoxy group, a ($C_2$–$C_6$) alkenyloxy group, a ($C_2$–$C_6$) alkynyloxy group, a ($C_1$–$C_6$) alkylthio group, a ($C_1$–$C_6$) alkylsulfonyl group, a phenoxy group, a ($C_1$–$C_4$) alkoxy ($C_1$–$C_4$) alkyl group, a ($C_1$–$C_4$) haloalkyl group, a ($C_1$–$C_4$) haloalkoxy group, a ($C_1$–$C_4$) alkylcarbonyl group, a ($C_1$–$C_4$) alkoxycarbonyl group, an amino group, a mono($C_1$–$C_4$) alkylamino group, a di($C_1$–$C_4$) alkylamino group, an anilino group or a phenyl group [said group may be substituted by a halogen atom, a ($C_1$–$C_4$) alkyl group or a ($C_1$–$C_4$) alkoxy group], Y is a halogen atom, a nitro group, a cyano group, a ($C_1$–$C_6$) alkyl group, a ($C_2$–$C_6$) alkenyl group, a ($C_2$–$C_6$) alkynyl group, a ($C_1$–$C_6$) alkoxy group, a ($C_2$–$C_6$) alkenyloxy group, a ($C_2$–$C_6$) alkynyloxy group, a ($C_1$–$C_4$) haloalkoxy group, a ($C_1$–$C_6$) alkylthio group, a ($C_1$–$C_4$) alkoxy ($C_1$–$C_4$) alkyl group, a ($C_1$–$C_4$) haloalkyl group, a ($C_1$–$C_4$) alkylcarbonyl group, a ($C_1$–$C_4$) alkoxycarbonyl group, a benzoyl group, an amino group, a mono($C_1$–$C_4$) alkylamino group, a di($C_1$–$C_4$) alkylamino group, a phenyl group [said group may be substituted by a halogen atom, a ($C_1$–$C_4$) alkyl group or a ($C_1$–$C_4$) alkoxy group] or a phenoxy group [said group may be substituted by a halogen atom, a ($C_1$–$C_4$) alkyl group or a ($C_1$–$C_4$) alkoxy group], and n is 0 or an integer of from 1 to 3}, and an agricultural/horticultural fungicide containing the pyrimidinylbenzimidazole or triazinylbenzimidazole derivative as the active ingredient.

Now, the symbols and terms used in the present specification will be explained below.

The halogen atom is a fluorine atom, a chlorine atom, a bromine atom or an iodine atom.

A notation such as ($C_1$–$C_6$) indicates that the carbon number of a substituent following this notation is from 1 to 6 in this case.

The ($C_1$–$C_6$) alkyl group is a linear or branched alkyl group and may, for example, be methyl, ethyl, n-propyl, isopropyl, n-butyl, isobutyl, sec-butyl, tert-butyl, n-pentyl, isopentyl, neopentyl, n-hexyl or 3,3-dimethylbutyl.

The ($C_3$–$C_6$) cycloalkyl may, for example, be cyclopropyl, cyclopentyl or cyclohexyl.

The ($C_1$–$C_4$) haloalkyl group is a linear or branched alkyl group substituted by a halogen atom and may, for example, be fluoromethyl, chloromethyl, difluoromethyl, dichloromethyl, trifluoromethyl or pentafluoroethyl.

The ($C_2$–$C_6$) alkenyl group is a linear or branched alkenyl group and may, for example, be vinyl, 1-propenyl, 2-propenyl, isopropenyl, 1-butenyl or 2-butenyl.

The ($C_2$–$C_6$) alkynyl group is a linear or branched alkynyl group and may, for example, be ethynyl, 1-propynyl, 2-propynyl, 1-butynyl, 2-butynyl, 3-butynyl, 4-methyl-1-pentynyl or 3-methyl-1-pentynyl.

The ($C_1$–$C_6$) alkoxy group is an alkyloxy group wherein the alkyl moiety has the above meaning and may, for example, be methoxy, ethoxy, n-propoxy, isopropoxy, n-butoxy, isobutoxy, sec-butoxy, tert-butoxy, n-pentyloxy, isopentyloxy or n-hexyloxy.

The ($C_2$–$C_6$) alkenyloxy group is an alkenyloxy group wherein the alkenyl moiety has the above meaning, and may, for example, be allyloxy, isopropenyloxy or 2-butenyloxy.

The ($C_2$–$C_6$) alkynyloxy group is an alkynyloxy group wherein the alkynyl moiety has the above meaning, and may, for example, be 2-propynyloxy, 2-butynyloxy or 3-butynyloxy.

The ($C_3$–$C_6$) cycloalkoxy group is a cycloalkyloxy group wherein the cycloalkyl moiety has the above meaning, and may, for example, be cyclopropyloxy, cyclopentyloxy or cyclohexyloxy.

The ($C_1$–$C_4$) haloalkoxy group is a haloalkyloxy group wherein the haloalkyl moiety has the above meaning, and may, for example, be fluoromethoxy, difluoromethoxy, trifluoromethoxy or pentafluoroethoxy.

The ($C_1$–$C_6$) alkylthio group is an alkylthio group wherein the alkyl moiety has the above meaning, and may, for example, be methylthio, ethylthio, n-propylthio, isopropylthio, n-butylthio, isobutylthio, sec-butylthio, tert-butylthio or n-hexylthio.

The ($C_3$–$C_6$) cycloalkyl ($C_1$–$C_4$) alkoxy group may, for example, be cyclopropylmethyloxy, cyclopentylmethyloxy or cyclohexylmethyloxy.

The ($C_1$–$C_4$) alkoxy ($C_1$–$C_4$) alkyl group is a group wherein the alkyl moiety and the alkoxy moiety have the above meanings, and may, for example, be a group such as methoxymethyl, ethoxymethyl, isopropoxymethyl, pentyloxymethyl, methoxyethyl or butoxyethyl.

The ($C_1$–$C_4$) alkoxy ($C_1$–$C_4$) alkyloxy group is a group wherein the alkyl moiety and the alkoxy moiety have the above meanings, and may, for example, be a group such as methoxymethyloxy, ethoxymethyloxy, isopropoxymethyloxy, pentyloxymethyloxy, methoxyethyloxy or butoxyethyloxy.

The cyano ($C_1$–$C_4$) alkyloxy group is a group wherein the alkyl moiety has the above meaning, and may, for example, be a group such as cyanomethyloxy, cyanoethyloxy or cyanopropyloxy.

The ($C_1$–$C_4$) alkylcarbonyl group is an alkylcarbonyl group wherein the alkyl moiety has the above meaning, and may, for example, be a group such as acetyl, propionyl, butyryl, isobutyryl, pivaloyl or hexanoyl.

The ($C_1$–$C_4$) alkoxycarbonyl group is an alkoxycarbonyl group wherein the alkoxy moiety has the above meaning, and may, for example, be methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentyloxycarbonyl or n-hexyloxycarbonyl.

The mono ($C_1$–$C_4$) alkylamino group is a monoalkylamino group wherein the alkyl moiety has the above meaning, and may, for example, be methylamino, ethylamino, n-propylamino, isopropylamino, n-butylamino, isobutylamino, sec-butylamino, tert-butylamino or n-hexylamino.

The di ($C_1$–$C_4$) alkylamino group may, for example, be dimethylamino, diethylamino, dipropylamino or dibutylamino.

The ($C_1$–$C_6$) alkylsulfonyl group is an alkylsulfonyl group wherein the alkyl moiety has the above meaning, and may, for example, be methylsulfonyl, ethylsulfonyl, n-propylsulfonyl, isopropylsulfonyl, n-butylsulfonyl, isobutylsulfonyl, sec-butylsulfonyl, tert-butylsulfonyl or n-hexylsulfonyl.

Now, specific examples of the compounds of the present invention represented by the general formula [I] will be disclosed in Tables 1 to 35. However, the compounds of the present invention are not limited to such compounds. Here, the compound numbers will be referred to in the subsequent description.

Symbols in the Tables have the following meanings respectively. Me represents methyl, Et represents ethyl, Pr represents n-propyl, Pr-i represents isopropyl, Bu represents n-butyl, Pr-c represents cyclopropyl, Pn-c represents cyclopentyl, Ph represents phenyl, and Bn represents benzyl. Further, Ph(2-Cl) represents 2-chlorophenyl, and Bn(4-Cl) represents 4-chlorobenzyl, for example.

TABLE 1

| Compound No. | X | Yn | A | R$^1$ | R$^2$ | m.p. (° C.) or RI ($n_D^{20}$) |
|---|---|---|---|---|---|---|
| I-1 | H | H | CH | OMe | OMe | 167–169 |
| I-2 | Cl | H | CH | OMe | OMe | 90–91 |
| I-3 | Br | H | CH | OMe | OMe | 87–90 |
| I-4 | SMe | H | CH | OMe | OMe | 135–137 |
| I-5 | SO$_2$Me | H | CH | OMe | OMe | 114–117 |
| I-6 | Me | H | CH | OMe | OMe | 132–134 |
| I-7 | Et | H | CH | OMe | OMe | 102–104 |
| I-8 | Pr | H | CH | OMe | OMe | 107–110 |
| I-9 | Pr-i | H | CH | OMe | OMe | 70–73 |
| I-10 | Pr-c | H | CH | OMe | OMe | 62–64 |
| I-11 | Bu | H | CH | OMe | OMe | |
| I-12 | Bn | H | CH | OMe | OMe | 94–96 |
| I-13 | Bn(4-Cl) | H | CH | OMe | OMe | 122–125 |
| I-14 | Bn(4-Me) | H | CH | OMe | OMe | 88–90 |
| I-15 | Bn(4-OMe) | H | CH | OMe | OMe | |
| I-16 | CH=CH$_2$ | H | CH | OMe | OMe | |
| I-17 | C≡CH | H | CH | OMe | OMe | |
| I-18 | OMe | H | CH | OMe | OMe | 121–122 |
| I-19 | OCH$_2$CH=CH$_2$ | H | CH | OMe | OMe | |
| I-20 | OCH$_2$C≡CH | H | CH | OMe | OMe | |
| I-21 | CH$_2$CF$_3$ | H | CH | OMe | OMe | |
| I-22 | CH$_2$OEt | H | CH | OMe | OMe | 103–104 |
| I-23 | CH$_2$Cl | H | CH | OMe | OMe | 132–135 |
| I-24 | CH$_2$I | H | CH | OMe | OMe | 138–141 |
| I-25 | CCl$_3$ | H | CH | OMe | OMe | 128–131 |
| I-26 | CF$_3$ | H | CH | OMe | OMe | 79–80 |
| I-27 | C$_2$F$_5$ | H | CH | OMe | OMe | 97–100 |
| I-28 | NH$_2$ | H | CH | OMe | OMe | | m.p. Melting point
RI: Refractive index

TABLE 2

| Compound No. | X | Yn | A | R$^1$ | R$^2$ | m.p. (° C.) or RI ($n_D^{20}$) |
|---|---|---|---|---|---|---|
| I-29 | NHMe | H | CH | OMe | OMe | 135–138 |
| I-30 | N(Me)$_2$ | H | CH | OMe | OMe | 1.5642 |
| I-31 | NHPh | H | CH | OMe | OMe | |
| I-32 | CO$_2$Et | H | CH | OMe | OMe | |
| I-33 | COMe | H | CH | OMe | OMe | |
| I-34 | Ph | H | CH | OMe | OMe | 1.6219 |
| I-35 | Ph(4-Cl) | H | CH | OMe | OMe | 141–144 |
| I-36 | Ph(4-Me) | H | CH | OMe | OMe | |
| I-37 | Ph(4-OMe) | H | CH | OMe | OMe | |
| I-38 | CN | H | CH | OMe | OMe | 167–168 |
| I-39 | NO$_2$ | H | CH | OMe | OMe | |
| I-40 | H | H | N | OMe | OMe | 148–151 |
| I-41 | Cl | H | N | OMe | OMe | 168–171 |
| I-42 | Br | H | N | OMe | OMe | |
| I-43 | SMe | H | N | OMe | OMe | |
| I-44 | SO$_2$Me | H | N | OMe | OMe | |
| I-45 | Me | H | N | OMe | OMe | 180–182 |
| I-46 | Et | H | N | OMe | OMe | |
| I-47 | Pr | H | N | OMe | OMe | 127–128 |
| I-48 | Pr-i | H | N | OMe | OMe | 135–141 |
| I-49 | Pr-c | H | N | OMe | OMe | |
| I-50 | Bu | H | N | OMe | OMe | |
| I-51 | Bn | H | N | OMe | OMe | |
| I-52 | Bn(4-Cl) | H | N | OMe | OMe | |
| I-53 | Bn(4-Me) | H | N | OMe | OMe | |
| I-54 | Bn(4-OMe) | H | N | OMe | OMe | |
| I-55 | CH=CH$_2$ | H | N | OMe | OMe | |
| I-56 | C≡CH | H | N | OMe | OMe | |
| I-57 | OMe | H | N | OMe | OMe | |
| I-58 | OCH$_2$CH=CH$_2$ | H | N | OMe | OMe | |
| I-59 | OCH$_2$C≡CH | H | N | OMe | OMe | |
| I-60 | OCH$_2$CF$_3$ | H | N | OMe | OMe | |
| I-61 | OPh | H | N | OMe | OMe | |
| I-62 | CH$_2$OEt | H | N | OMe | OMe | |

TABLE 3

| Compound No. | X | Yn | A | R$^1$ | R$^2$ | m.p. (° C.) or RI ($n_D^{20}$) |
|---|---|---|---|---|---|---|
| I-63 | CH$_2$Cl | H | N | OMe | OMe | |
| I-64 | CH$_2$I | H | N | OMe | OMe | |
| I-65 | CCl$_3$ | H | N | OMe | OMe | |
| I-66 | CF$_3$ | H | N | OMe | OMe | 143–146 |
| I-67 | C$_2$F$_2$ | H | N | OMe | OMe | |
| I-68 | NH$_2$ | H | N | OMe | OMe | 261–264 |
| I-69 | NHMe | H | N | OMe | OMe | |
| I-70 | N(Me)$_2$ | H | N | OMe | OMe | |
| I-71 | NHPh | H | N | OMe | OMe | |
| I-72 | CO$_2$Et | H | N | OMe | OMe | |
| I-73 | COMe | H | N | OMe | OMe | |
| I-74 | Ph | H | N | OMe | OMe | |
| I-75 | Ph(4-Cl) | H | N | OMe | OMe | |
| I-76 | Ph(4-Me) | H | N | OMe | OMe | |
| I-77 | Ph(4-OMe) | H | N | OMe | OMe | |
| I-78 | CN | H | N | OMe | OMe | |
| I-79 | NO$_2$ | H | N | OMe | OMe | |
| I-80 | H | 4-Me | CH | OMe | OMe | 138–141 |
| I-81 | H | 4-Cl | CH | OMe | OMe | |

TABLE 3-continued

| Compound No. | X | Yn | A | R¹ | R² | m.p. (° C.) or RI ($n_D^{20}$) |
|---|---|---|---|---|---|---|
| I-82 | H | 5-F | CH | OMe | OMe | 175–178 |
| I-83 | H | 5-Cl | CH | OMe | OMe | 181–184 |
| I-84 | H | 5-Br | CH | OMe | OMe | 181–184 |
| I-85 | H | 5-Me | CH | OMe | OMe | 168–169 |
| I-86 | H | 5-Bu-t | CH | OMe | OMe | 138–141 |
| I-87 | H | 5-CF₃ | CH | OMe | OMe | 173–174 |
| I-88 | H | 5-OMe | CH | OMe | OMe | 162–164 |
| I-89 | H | 5-OEt | CH | OMe | OMe | 169–171 |
| I-90 | H | 5-OPr | CH | OMe | OMe | |
| I-91 | H | 5-OCF₃ | CH | OMe | OMe | 138–141 |
| I-92 | H | 5-OCH₂CH=CH₂ | CH | OMe | OMe | |
| I-93 | H | 5-OCH₂C≡CH | CH | OMe | OMe | |
| I-94 | H | 5-OPh | CH | OMe | OMe | |
| I-95 | H | 5-OPh(4-Cl) | CH | OMe | OMe | |
| I-96 | H | 5-OPh(4-Me) | CH | OMe | OMe | |

TABLE 4

| Compound No. | X | Yn | A | R¹ | R² | m.p. (° C.) or RI ($n_D^{20}$) |
|---|---|---|---|---|---|---|
| I-97 | H | 5-OPh(4-OMe) | CH | OMe | OMe | |
| I-98 | H | 5-SMe | CH | OMe | OMe | |
| I-99 | H | 5-CH₂OMe | CH | OMe | OMe | |
| I-100 | H | 5-COMe | CH | OMe | OMe | |
| I-101 | H | 5-COPh | CH | OMe | OMe | 223–226 |
| I-102 | H | 5-CO₂Et | CH | OMe | OMe | 185–188 |
| I-103 | H | 5-Ph | CH | OMe | OMe | 162–165 |
| I-104 | H | 5-Ph(4-Cl) | CH | OMe | OMe | |
| I-105 | H | 5-Ph(4-Me) | CH | OMe | OMe | |
| I-106 | H | 5-Ph(4-OMe) | CH | OMe | OMe | |
| I-107 | H | 5-NO₂ | CH | OMe | OMe | |
| I-108 | H | 5-NH₂ | CH | OMe | OMe | |
| I-109 | H | 5-NHMe | CH | OMe | OMe | |
| I-110 | H | 5-N(Me)₂ | CH | OMe | OMe | |
| I-111 | H | 5-CN | CH | OMe | OMe | 249–252 |
| I-112 | H | 6-F | CH | OMe | OMe | 192–193 |
| I-113 | H | 6-Cl | CH | OMe | OMe | 199–202 |
| I-114 | H | 6-Me | CH | OMe | OMe | 134–136 |
| I-115 | H | 6-CF₃ | CH | OMe | OMe | 192–193 |
| I-116 | H | 6-OMe | CH | OMe | OMe | 184–185 |
| I-117 | H | 6-CO₂Et | CH | OMe | OMe | 184–187 |
| I-118 | H | 6-COPh | CH | OMe | OMe | 176–179 |
| I-119 | H | 7-Me | CH | OMe | OMe | 134–137 |
| I-120 | H | 7-Cl | CH | OMe | OMe | |
| I-121 | H | 5,6-Cl₂ | CH | OMe | OMe | 217–220 |
| I-122 | H | 5,6-(Me)₂ | CH | OMe | OMe | 185–187 |
| I-123 | H | 5,6-(OMe)₂ | CH | OMe | OMe | |
| I-124 | H | 4-Br, 6-CF₃ | CH | OMe | OMe | 188–191 |
| I-125 | H | 4-Cl, 6-CF₃ | CH | OMe | OMe | 204–206 |
| I-126 | H | 4,5,6-F₃ | CH | OMe | OMe | |
| I-127 | H | 4-Me | N | OMe | OMe | |
| I-128 | H | 4-Cl | N | OMe | OMe | |
| I-129 | H | 5-F | N | OMe | OMe | |
| I-130 | H | 5-Cl | N | OMe | OMe | 175–178 |

TABLE 5

| Compound No. | X | Yn | A | R¹ | R² | m.p. (° C.) or RI ($n_D^{20}$) |
|---|---|---|---|---|---|---|
| I-131 | H | 5-Br | N | OMe | OMe | >300 |
| I-132 | H | 5-I | N | OMe | OMe | 145–148 |
| I-133 | H | 5-Me | N | OMe | OMe | 177–180 |
| I-134 | H | 5-Et | N | OMe | OMe | 120–123 |
| I-135 | H | 5-Pr | N | OMe | OMe | 101–104 |
| I-136 | H | 5-Pr-i | N | OMe | OMe | 87–90 |
| I-137 | H | 5-Bu-t | N | OMe | OMe | 146–147 |
| I-138 | H | 5-CH=CH₂ | N | OMe | OMe | |
| I-139 | H | 5-C≡CBu | N | OMe | OMe | |
| I-140 | H | 5-CF₃ | N | OMe | OMe | |
| I-141 | H | 5-OMe | N | OMe | OMe | 164–167 |
| I-142 | H | 5-OEt | N | OMe | OMe | |
| I-143 | H | 5-OPr | N | OMe | OMe | |
| I-144 | H | 5-OCF₃ | N | OMe | OMe | |
| I-145 | H | 5-OCH₂CH=CH₂ | N | OMe | OMe | |
| I-146 | H | 5-OCH₂C≡CH | N | OMe | OMe | |
| I-147 | H | 5-OPh | N | OMe | OMe | |
| I-148 | H | 5-OPh(4-Cl) | N | OMe | OMe | |
| I-149 | H | 5-OPh(4-Me) | N | OMe | OMe | |
| I-150 | H | 5-OPh(4-OMe) | N | OMe | OMe | |
| I-151 | H | 5-SMe | N | OMe | OMe | |
| I-152 | H | 5-CH₂OMe | N | OMe | OMe | |
| I-153 | H | 5-COMe | N | OMe | OMe | |
| I-154 | H | 5-COPh | N | OMe | OMe | |
| I-155 | H | 5-CO₂Et | N | OMe | OMe | |
| I-156 | H | 5-Ph | N | OMe | OMe | |
| I-157 | H | 5-Ph(4-Cl) | N | OMe | OMe | |
| I-158 | H | 5-Ph(4-Me) | N | OMe | OMe | |
| I-159 | H | 5-Ph(4-OMe) | N | OMe | OMe | |
| I-160 | H | 5-NO₂ | N | OMe | OMe | 210–213 |
| I-161 | H | 5-NH₂ | N | OMe | OMe | |
| I-162 | H | 5-NHMe | N | OMe | OMe | |
| I-163 | H | 5-N(Me)₂ | N | OMe | OMe | |
| I-164 | H | 5-CN | N | OMe | OMe | |

TABLE 6

| Compound No. | X | Yn | A | R¹ | R² | m.p. (° C.) or RI ($n_D^{20}$) |
|---|---|---|---|---|---|---|
| I-165 | H | 6-F | N | OMe | OMe | |
| I-166 | H | 6-Cl | N | OMe | OMe | |
| I-167 | H | 6-Me | N | OMe | OMe | |
| I-168 | H | 6-CF₃ | N | OMe | OMe | |
| I-169 | H | 6-OMe | N | OMe | OMe | |
| I-170 | H | 6-NO₂ | N | OMe | OMe | >300 |
| I-171 | H | 6-CO₂Et | N | OMe | OMe | |
| I-172 | H | 6-COPh | N | OMe | OMe | |
| I-173 | H | 7-Me | N | OMe | OMe | |
| I-174 | H | 7-Cl | N | OMe | OMe | |
| I-175 | H | 5,6-Cl₂ | N | OMe | OMe | 176–179 |
| I-176 | H | 5,6-(Me)₂ | N | OMe | OMe | 193–196 |

TABLE 6-continued

| Compound No. | X | Yn | A | R¹ | R² | m.p. (° C.) or RI ($n_D^{20}$) |
|---|---|---|---|---|---|---|
| I-177 | H | 5,6-(OMe)₂ | N | OMe | OMe | |
| I-178 | H | 4-Br, 6-CF₃ | N | OMe | OMe | |
| I-179 | H | 4-Cl, 6-CF₃ | N | OMe | OMe | |
| I-180 | H | 4,5,6-F₃ | N | OMe | OMe | |
| I-181 | Me | 4-Me | CH | OMe | OMe | 127–130 |
| I-182 | Me | 4-Cl | CH | OMe | OMe | |
| I-183 | Me | 5-F | CH | OMe | OMe | 163–165 |
| I-184 | Me | 5-Cl | CH | OMe | OMe | 153–156 |
| I-185 | Me | 5-Br | CH | OMe | OMe | 180–183 |
| I-186 | Me | 5-Me | CH | OMe | OMe | 163–166 |
| I-187 | Me | 5-Bu-t | CH | OMe | OMe | 126–129 |
| I-188 | Me | 5-CF₃ | CH | OMe | OMe | 129–132 |
| I-189 | Me | 5-OMe | CH | OMe | OMe | 190–193 |
| I-190 | Me | 5-OEt | CH | OMe | OMe | 211–214 |
| I-191 | Me | 5-OPr | CH | OMe | OMe | |
| I-192 | Me | 5-OCF₃ | CH | OMe | OMe | 137–139 |
| I-193 | Me | 5-OPh | CH | OMe | OMe | |
| I-194 | Me | 5-CO₂Et | CH | OMe | OMe | 173–176 |
| I-195 | Me | 5-COPh | CH | OMe | OMe | 169–171 |
| I-196 | Me | 5-Ph | CH | OMe | OMe | 164–166 |
| I-197 | Me | 5-NH₂ | CH | OMe | OMe | |
| I-198 | Me | 5-N(Me)₂ | CH | OMe | OMe | |

TABLE 7

| Compound No. | X | Yn | A | R¹ | R² | m.p. (° C.) or RI ($n_D^{20}$) |
|---|---|---|---|---|---|---|
| I-199 | Me | 5-CN | CH | OMe | OMe | 211–214 |
| I-200 | Me | 6-F | CH | OMe | OMe | 162–163 |
| I-201 | Me | 6-Cl | CH | OMe | OMe | 165–166 |
| I-202 | Me | 6-Me | CH | OMe | OMe | 128–131 |
| I-203 | Me | 6-CF₃ | CH | OMe | OMe | 162–165 |
| I-204 | Me | 6-OMe | CH | OMe | OMe | 158–161 |
| I-205 | Me | 6-OEt | CH | OMe | OMe | |
| I-206 | Me | 6-OPr | CH | OMe | OMe | |
| I-207 | Me | 6-CO₂Et | CH | OMe | OMe | 184–187 |
| I-208 | Me | 6-COPh | CH | OMe | OMe | 179–182 |
| I-209 | Me | 5,6-Cl₂ | CH | OMe | OMe | 204–206 |
| I-210 | Me | 5,6-(Me)₂ | CH | OMe | OMe | 169–172 |
| I-211 | Me | 5,6-(OMe)₂ | CH | OMe | OMe | |
| I-212 | Me | 4-Me | N | OMe | OMe | 180–182 |
| I-213 | Me | 4-Cl | N | OMe | OMe | |
| I-214 | Me | 5-F | N | OMe | OMe | 185–188 |
| I-215 | Me | 5-Cl | N | OMe | OMe | 173–176 |
| I-216 | Me | 5-Br | N | OMe | OMe | >300 |
| I-217 | Me | 5-I | N | OMe | OMe | 161–164 |
| I-218 | Me | 5-Me | N | OMe | OMe | 192–195 |
| I-219 | Me | 5-Et | N | OMe | OMe | 113–116 |
| I-220 | Me | 5-Pr | N | OMe | OMe | 128–131 |
| I-221 | Me | 5-Pr-i | N | OMe | OMe | 124–125 |
| I-222 | Me | 5-Bu-t | N | OMe | OMe | 143–144 |
| I-223 | Me | 5-CH=CH₂ | N | OMe | OMe | |
| I-224 | Me | 5-C≡CBu | N | OMe | OMe | 111–114 |
| I-225 | Me | 5-CF₃ | N | OMe | OMe | 167–170 |
| I-226 | Me | 5-OMe | N | OMe | OMe | 161–164 |
| I-227 | Me | 5-OEt | N | OMe | OMe | |
| I-228 | Me | 5-OPr | N | OMe | OMe | |
| I-229 | Me | 5-OCF₃ | N | OMe | OMe | 128–131 |
| I-230 | Me | 5-OPh | N | OMe | OMe | |
| I-231 | Me | 5-SMe | N | OMe | OMe | |
| I-232 | Me | 5-CO₂Me | N | OMe | OMe | 148–151 |

TABLE 8

| Compound No. | X | Yn | A | R¹ | R² | m.p. (° C.) or RI ($n_D^{20}$) |
|---|---|---|---|---|---|---|
| I-233 | Me | 5-CO₂Et | N | OMe | OMe | |
| I-234 | Me | 5-COMe | N | OMe | OMe | 155–158 |
| I-235 | Me | 5-COPh | N | OMe | OMe | 163–166 |
| I-236 | Me | 5-Ph | N | OMe | OMe | |
| I-237 | Me | 5-NH₂ | N | OMe | OMe | |
| I-238 | Me | 5-N(Me)₂ | N | OMe | OMe | |
| I-239 | Me | 5-CN | N | OMe | OMe | 188–191 |
| I-240 | Me | 6-F | N | OMe | OMe | |
| I-241 | Me | 6-Cl | N | OMe | OMe | |
| I-242 | Me | 6-Me | N | OMe | OMe | 130–133 |
| I-243 | Me | 6-CF₃ | N | OMe | OMe | |
| I-244 | Me | 6-OMe | N | OMe | OMe | |
| I-245 | Me | 6-OEt | N | OMe | OMe | |
| I-246 | Me | 6-OPr | N | OMe | OMe | |
| I-247 | Me | 6-CO₂Et | N | OMe | OMe | |
| I-248 | Me | 6-COPh | N | OMe | OMe | |
| I-249 | Me | 5,6-Cl₂ | N | OMe | OMe | |
| I-250 | Me | 4,6-(Me)₂ | N | OMe | OMe | 172–175 |
| I-251 | Me | 5,6-(Me)₂ | N | OMe | OMe | 165–168 |
| I-252 | Me | 5,6-(OMe)₂ | N | OMe | OMe | |
| I-253 | Cl | 4-Me | CH | OMe | OMe | |
| I-254 | Cl | 4-Cl | CH | OMe | OMe | |
| I-255 | Cl | 5-F | CH | OMe | OMe | 139–142 |
| I-256 | Cl | 5-Cl | CH | OMe | OMe | 159–161 |
| I-257 | Cl | 5-Br | CH | OMe | OMe | |
| I-258 | Cl | 5-Me | CH | OMe | OMe | 145–148 |
| I-259 | Cl | 5-CF₃ | CH | OMe | OMe | 136–139 |
| I-260 | Cl | 5-OMe | CH | OMe | OMe | 148–150 |
| I-261 | Cl | 5-OEt | CH | OMe | OMe | 187–190 |
| I-262 | Cl | 5-OPr | CH | OMe | OMe | |
| I-263 | Cl | 5-OCF₃ | CH | OMe | OMe | 102–105 |
| I-264 | Cl | 5-OPh | CH | OMe | OMe | |
| I-265 | Cl | 5-COPh | CH | OMe | OMe | |
| I-266 | Cl | 5-Ph | CH | OMe | OMe | |

TABLE 9

| Compound No. | X | Yn | A | R¹ | R² | m.p. (° C.) or RI ($n_D^{20}$) |
|---|---|---|---|---|---|---|
| I-267 | Cl | 5-NH₂ | CH | OMe | OMe | |
| I-268 | Cl | 5-N(Me)₂ | CH | OMe | OMe | |
| I-269 | Cl | 5-CN | CH | OMe | OMe | |
| I-270 | Cl | 6-F | CH | OMe | OMe | |
| I-271 | Cl | 6-Cl | CH | OMe | OMe | 163–164 |
| I-272 | Cl | 6-Me | CH | OMe | OMe | 98–101 |
| I-273 | Cl | 5,6-(OMe)₂ | CH | OMe | OMe | |
| I-274 | Cl | 4-Me | N | OMe | OMe | |
| I-275 | Cl | 4-Cl | N | OMe | OMe | |
| I-276 | Cl | 5-F | N | OMe | OMe | |
| I-277 | Cl | 5-Cl | N | OMe | OMe | 146–149 |
| I-278 | Cl | 5-Br | N | OMe | OMe | |
| I-279 | Cl | 5-Me | N | OMe | OMe | 159–162 |
| I-280 | Cl | 5-CF₃ | N | OMe | OMe | |
| I-281 | Cl | 5-OMe | N | OMe | OMe | |
| I-282 | Cl | 5-OEt | N | OMe | OMe | |
| I-283 | Cl | 5-OPr | N | OMe | OMe | |
| I-284 | Cl | 5-OCF₃ | N | OMe | OMe | |
| I-285 | Cl | 5-OPh | N | OMe | OMe | |
| I-286 | Cl | 5-COPh | N | OMe | OMe | |
| I-287 | Cl | 5-Ph | N | OMe | OMe | |
| I-288 | Cl | 5-NH₂ | N | OMe | OMe | |
| I-289 | Cl | 5-N(Me)₂ | N | OMe | OMe | |
| I-290 | Cl | 5-CN | N | OMe | OMe | |
| I-291 | Cl | 6-F | N | OMe | OMe | |
| I-292 | Cl | 6-Cl | N | OMe | OMe | |
| I-293 | Cl | 6-Me | N | OMe | OMe | |
| I-294 | Cl | 5,6-(OMe)₂ | N | OMe | OMe | |
| I-295 | CF₃ | 5-F | CH | OMe | OMe | 133–136 |
| I-296 | CF₃ | 5-Cl | CH | OMe | OMe | 114-116 |
| I-297 | CF₃ | 5-Br | CH | OMe | OMe | |

TABLE 9-continued

| Compound No. | X | Yn | A | R¹ | R² | m.p. (° C.) or RI ($n_D^{20}$) |
|---|---|---|---|---|---|---|
| I-298 | CF₃ | 5-Me | CH | OMe | OMe | 93–96 |
| I-299 | CF₃ | 5-CF₃ | CH | OMe | OMe | 78–79 |
| I-300 | CF₃ | 5-OMe | CH | OMe | OMe | 129–132 |

TABLE 10

| Compound No. | X | Yn | A | R¹ | R² | m.p. (° C.) or RI ($n_D^{20}$) |
|---|---|---|---|---|---|---|
| I-301 | CF₃ | 5-OEt | CH | OMe | OMe | 151–154 |
| I-302 | CF₃ | 5-OPr | CH | OMe | OMe | |
| I-303 | CF₃ | 5-N(Me)₂ | CH | OMe | OMe | |
| I-304 | CF₃ | 5-CN | CH | OMe | OMe | |
| I-305 | CF₃ | 6-F | CH | OMe | OMe | |
| I-306 | CF₃ | 6-Cl | CH | OMe | OMe | |
| I-307 | CF₃ | 6-Me | CH | OMe | OMe | 132–135 |
| I-308 | CF₃ | 5,6-(OMe)₂ | CH | OMe | OMe | |
| I-309 | CF₃ | 5-F | N | OMe | OMe | 170–173 |
| I-310 | CF₃ | 5-Cl | N | OMe | OMe | 135–138 |
| I-311 | CF₃ | 5-Br | N | OMe | OMe | 111–114 |
| I-312 | CF₃ | 5-Me | N | OMe | OMe | 137–140 |
| I-313 | CF₃ | 5-Et | N | OMe | OMe | 104–107 |
| I-314 | CF₃ | 5-Pr | N | OMe | OMe | 89–92 |
| I-315 | CF₃ | 5-Pr-i | N | OMe | OMe | 118–121 |
| I-316 | CF₃ | 5-Bu-t | N | OMe | OMe | 113–116 |
| I-317 | CF₃ | 5-CF₃ | N | OMe | OMe | |
| I-318 | CF₃ | 5-OMe | N | OMe | OMe | 165–168 |
| I-319 | CF₃ | 5-OEt | N | OMe | OMe | |
| I-320 | CF₃ | 5-OPr | N | OMe | OMe | |
| I-321 | CF₃ | 5-OCF₃ | N | OMe | OMe | 187–190 |
| I-322 | CF₃ | 5-SMe | N | OMe | OMe | |
| I-323 | CF₃ | 5-NHMe | N | OMe | OMe | |
| I-324 | CF₃ | 5-N(Me)₂ | N | OMe | OMe | |
| I-325 | CF₃ | 5-CN | N | OMe | OMe | 188–191 |
| I-326 | CF₃ | 5-CO₂Me | N | OMe | OMe | 126–129 |
| I-327 | CF₃ | 5-I | N | OMe | OMe | 115–118 |
| I-328 | CF₃ | 6-F | N | OMe | OMe | |
| I-329 | CF₃ | 6-Cl | N | OMe | OMe | |
| I-330 | CF₃ | 6-Me | N | OMe | OMe | |
| I-331 | CF₃ | 5,6-(OMe)₂ | N | OMe | OMe | |
| I-332 | Et | 5-F | CH | OMe | OMe | 135–138 |
| I-333 | Et | 5-Cl | CH | OMe | OMe | 137–140 |
| I-334 | Et | 5-Me | CH | OMe | OMe | 120–122 |

TABLE 11

| Compound No. | X | Yn | A | R¹ | R² | m.p. (° C.) or RI ($n_D^{20}$) |
|---|---|---|---|---|---|---|
| I-335 | Et | 5-CF₃ | CH | OMe | OMe | 117–118 |
| I-336 | Et | 5-OMe | CH | OMe | OMe | 118–120 |
| I-337 | Et | 5-OEt | CH | OMe | OMe | |
| I-338 | Et | 5-OPr | CH | OMe | OMe | |
| I-339 | Et | 5-N(Me)₂ | CH | OMe | OMe | |
| I-340 | Et | 5-CN | CH | OMe | OMe | |
| I-341 | Et | 6-F | CH | OMe | OMe | |
| I-342 | Et | 6-Cl | CH | OMe | OMe | |
| I-343 | Et | 6-Me | CH | OMe | OMe | |
| I-344 | Et | 5,6-(OMe)₂ | CH | OMe | OMe | |
| I-345 | Et | 5-F | N | OMe | OMe | |
| I-346 | Et | 5-Cl | N | OMe | OMe | 125–128 |
| I-347 | Et | 5-Me | N | OMe | OMe | |
| I-348 | Et | 5-CF₃ | N | OMe | OMe | |
| I-349 | Et | 5-OMe | N | OMe | OMe | |
| I-350 | Et | 5-OEt | N | OMe | OMe | |
| I-351 | Et | 5-OPr | N | OMe | OMe | |
| I-352 | Et | 5-N(Me)₂ | N | OMe | OMe | |
| I-353 | Et | 5-CN | N | OMe | OMe | |

TABLE 11-continued

| Compound No. | X | Yn | A | R¹ | R² | m.p. (° C.) or RI ($n_D^{20}$) |
|---|---|---|---|---|---|---|
| I-354 | Et | 6-F | N | OMe | OMe | |
| I-355 | Et | 6-Cl | N | OMe | OMe | |
| I-356 | Et | 6-Me | N | OMe | OMe | |
| I-357 | Et | 5,6-(OMe)₂ | N | OMe | OMe | |
| I-358 | Pr | 5-Cl | N | OMe | OMe | 128–131 |
| I-359 | Pr-i | 5-Cl | N | OMe | OMe | 160–163 |
| I-360 | Pr-c | 5-Cl | N | OMe | OMe | 146–149 |
| I-361 | NH₂ | 5-F | CH | OMe | OMe | 236–239 |
| I-362 | NH₂ | 5-Me | CH | OMe | OMe | >300 |
| I-363 | NH₂ | 5-CF₃ | CH | OMe | OMe | 268–271 |
| I-364 | NH₂ | 5-OMe | CH | OMe | OMe | 232–235 |
| I-365 | NH₂ | 5-OEt | CH | OMe | OMe | 239–242 |
| I-366 | NH₂ | 6-Me | CH | OMe | OMe | >300 |
| I-367 | NH₂ | 5,6-(OMe)₂ | CH | OMe | OMe | |
| I-368 | NH₂ | 5-Cl | N | OMe | OMe | 293–296 |

TABLE 12

| Compound No. | X | Yn | A | R¹ | R² | m.p. (° C.) or RI ($n_D^{20}$) |
|---|---|---|---|---|---|---|
| I-369 | NH₂ | 5-Me | N | OMe | OMe | 272–275 |
| I-370 | NH₂ | 5-CF₃ | N | OMe | OMe | |
| I-371 | NH₂ | 5-OMe | N | OMe | OMe | |
| I-372 | NH₂ | 5-OEt | N | OMe | OMe | |
| I-373 | NH₂ | 6-Me | N | OMe | OMe | |
| I-374 | NH₂ | 5,6-(OMe)₂ | N | OMe | OMe | |
| I-375 | NHMe | 5-Cl | N | OMe | OMe | 238–241 |
| I-376 | N(Me)₂ | 5-Cl | N | OMe | OMe | 66–69 |
| I-377 | CH₂OMe | 5-Cl | N | OMe | OMe | 105–108 |
| I-378 | Ph | 5-Cl | N | OMe | OMe | 137–140 |
| I-379 | Bn | 5-Cl | N | OMe | OMe | 192–195 |
| I-380 | CN | 5-Cl | CH | OMe | OMe | 223–226 |
| I-381 | CN | 5-Me | CH | OMe | OMe | 229–231 |
| I-382 | CN | 5-CF₃ | CH | OMe | OMe | |
| I-383 | CN | 5-OMe | CH | OMe | OMe | |
| I-384 | CN | 5-Cl | N | OMe | OMe | |
| I-385 | CN | 5-Me | N | OMe | OMe | |
| I-386 | CN | 5-CF₃ | N | OMe | OMe | |
| I-387 | CN | 5-OMe | N | OMe | OMe | |
| I-388 | SMe | 5-Cl | CH | OMe | OMe | 184–187 |
| I-389 | SMe | 5-Me | CH | OMe | OMe | 155–158 |
| I-390 | SMe | 5-CF₃ | CH | OMe | OMe | |
| I-391 | SMe | 5-OMe | CH | OMe | OMe | |
| I-392 | SMe | 6-Cl | CH | OMe | OMe | |
| I-393 | SMe | 6-Me | CH | OMe | OMe | |
| I-394 | SMe | 5-Cl | N | OMe | OMe | 135–138 |
| I-395 | SMe | 5-Me | N | OMe | OMe | |
| I-396 | SMe | 5-CF₃ | N | OMe | OMe | |
| I-397 | SMe | 5-OMe | N | OMe | OMe | |
| I-398 | SMe | 6-Cl | N | OMe | OMe | |
| I-399 | SMe | 6-Me | N | OMe | OMe | |
| I-400 | CCl₃ | 5-Cl | CH | OMe | OMe | 132–134 |
| I-401 | CCl₃ | 5-Me | CH | OMe | OMe | |
| I-402 | CCl₃ | 5-OMe | CH | OMe | OMe | |

TABLE 13

| Compound No. | X | Yn | A | R¹ | R² | m.p. (° C.) or RI ($n_D^{20}$) |
|---|---|---|---|---|---|---|
| I-403 | CCl₃ | 6-Cl | CH | OMe | OMe | |
| I-404 | CCl₃ | 6-Me | CH | OMe | OMe | 136–139 |
| I-405 | CCl₃ | 5-Cl | N | OMe | OMe | 123–126 |
| I-406 | CCl₃ | 5-Me | N | OMe | OMe | 140–151 |
| I-407 | CCl₃ | 5-OMe | N | OMe | OMe | |

TABLE 13-continued

| Compound No. | X | Yn | A | R¹ | R² | m.p. (° C.) or RI ($n_D^{20}$) |
|---|---|---|---|---|---|---|
| I-408 | CCl₃ | 5-Br | N | OMe | OMe | |
| I-409 | CCl₃ | 6-Cl | N | OMe | OMe | |
| I-410 | CCl₃ | 6-Me | N | OMe | OMe | |
| I-411 | CF₂Cl | 5-Me | N | OMe | OMe | 109–111 |
| I-412 | CF₂Cl | 5-Cl | N | OMe | OMe | 86–89 |
| I-413 | CF₂Cl | 5-Br | N | OMe | OMe | |
| I-414 | CF₂Cl | 5-OMe | N | OMe | OMe | |
| I-415 | CH₂Cl | 5-Me | N | OMe | OMe | 143–145 |
| I-416 | CH₂Cl | 5-Cl | N | OMe | OMe | 160–161 |
| I-417 | CH₂Cl | 5-Br | N | OMe | OMe | |
| I-418 | CH₂Cl | 5-OMe | N | OMe | OMe | |
| I-419 | C₂F₅ | 5-Me | N | OMe | OMe | |
| I-420 | C₂F₅ | 5-Cl | N | OMe | OMe | |
| I-421 | C₂F₅ | 5-Br | N | OMe | OMe | |
| I-422 | C₂F₅ | 5-OMe | N | OMe | OMe | |
| I-423 | SO₂Me | 5-Cl | CH | OMe | OMe | 149–152 |
| I-424 | SO₂Me | 5-Me | CH | OMe | OMe | 176–177 |
| I-425 | SO₂Me | 6-Me | CH | OMe | OMe | |
| I-426 | SO₂Me | 5-Cl | N | OMe | OMe | |
| I-427 | SO₂Me | 5-Me | N | OMe | OMe | |
| I-428 | SO₂Me | 6-Me | N | OMe | OMe | |
| I-429 | OMe | 5-Cl | CH | OMe | OMe | 182–185 |
| I-430 | OMe | 6-Cl | CH | OMe | OMe | 178–180 |
| I-431 | OMe | 5-Cl | N | OMe | OMe | |
| I-432 | OMe | 6-Cl | N | OMe | OMe | |
| I-433 | H | H | N | OMe | OEt | |
| I-434 | H | 5-Cl | N | OMe | OEt | |
| I-435 | H | 5-Br | N | OMe | OEt | 194–196 |
| I-436 | H | 5-Me | N | OMe | OEt | |

TABLE 14

| Compound No. | X | Yn | A | R¹ | R² | m.p. (° C.) or RI ($n_D^{20}$) |
|---|---|---|---|---|---|---|
| I-437 | Me | H | N | OMe | OEt | |
| I-438 | Me | 5-Cl | N | OMe | OEt | 153–156 |
| I-439 | Me | 5-Br | N | OMe | OEt | 143–145 |
| I-440 | Me | 5-Me | N | OMe | OEt | 155–156 |
| I-441 | Cl | 5-Cl | N | OMe | OEt | |
| I-442 | Cl | 5-Br | N | OMe | OEt | |
| I-443 | Cl | 5-Me | N | OMe | OEt | |
| I-444 | CF₃ | H | N | OMe | OEt | |
| I-445 | CF₃ | 5-Me | N | OMe | OEt | 147–150 |
| I-446 | CF₃ | 5-Cl | N | OMe | OEt | 149–151 |
| I-447 | CF₃ | 5-Br | N | OMe | OEt | 138–139 |
| I-448 | CF₂Cl | 5-Cl | N | OMe | OEt | |
| I-449 | CF₂Cl | 5-Br | N | OMe | OEt | |
| I-450 | CF₂Cl | 5-Me | N | OMe | OEt | |
| I-451 | CH₂Cl | 5-Cl | N | OMe | OEt | |
| I-452 | CH₂Cl | 5-Br | N | OMe | OEt | |
| I-453 | CH₂Cl | 5-Me | N | OMe | OEt | |
| I-454 | C₂F₅ | 5-Cl | N | OMe | OEt | |
| I-455 | C₂F₅ | 5-Br | N | OMe | OEt | |
| I-456 | C₂F₅ | 5-Me | N | OMe | OEt | |
| I-457 | H | H | CH | OEt | OEt | 122–124 |
| I-458 | Cl | H | CH | OEt | OEt | 79–82 |
| I-459 | Br | H | CH | OEt | OEt | |
| I-460 | SMe | H | CH | OEt | OEt | 122–125 |
| I-461 | Me | H | CH | OEt | OEt | 88–91 |
| I-462 | Et | H | CH | OEt | OEt | 90–93 |
| I-463 | OMe | H | CH | OEt | OEt | 87–89 |
| I-464 | OEt | H | CH | OEt | OEt | 96–99 |
| I-465 | CF₃ | H | CH | OEt | OEt | 90–92 |
| I-466 | NH₂ | H | CH | OEt | OEt | 222–225 |
| I-467 | CN | H | CH | OEt | OEt | 153–156 |
| I-468 | H | H | N | OEt | OEt | |
| I-469 | Cl | H | N | OEt | OEt | |
| I-470 | Br | H | N | OEt | OEt | |

TABLE 15

| Compound No. | X | Yn | A | R¹ | R² | m.p. (° C.) or RI ($n_D^{20}$) |
|---|---|---|---|---|---|---|
| I-471 | SMe | H | N | OEt | OEt | |
| I-472 | Me | H | N | OEt | OEt | |
| I-473 | Et | H | N | OEt | OEt | |
| I-474 | OMe | H | N | OEt | OEt | |
| I-475 | OEt | H | N | OEt | OEt | |
| I-476 | CF₃ | H | N | OEt | OEt | |
| I-477 | NH₂ | H | N | OEt | OEt | |
| I-478 | CN | H | N | OEt | OEt | |
| I-479 | H | 5-F | CH | OEt | OEt | 156–159 |
| I-480 | H | 5-Cl | CH | OEt | OEt | 177–180 |
| I-481 | H | 5-Br | CH | OEt | OEt | |
| I-482 | H | 5-Me | CH | OEt | OEt | 135–138 |
| I-483 | H | 5-CF₃ | CH | OEt | OEt | 165–168 |
| I-484 | H | 5-OMe | CH | OEt | OEt | |
| I-485 | H | 5-OEt | CH | OEt | OEt | |
| I-486 | H | 6-Cl | CH | OEt | OEt | 164–167 |
| I-487 | H | 5,6-(OMe)₂ | CH | OEt | OEt | |
| I-488 | H | 5-F | N | OEt | OEt | |
| I-489 | H | 5-Cl | N | OEt | OEt | |
| I-490 | H | 5-Br | N | OEt | OEt | 170–173 |
| I-491 | H | 5-Me | N | OEt | OEt | |
| I-492 | H | 5-Bu-t | N | OEt | OEt | 107–110 |
| I-493 | H | 5-CF₃ | N | OEt | OEt | |
| I-494 | H | 5-OMe | N | OEt | OEt | |
| I-495 | H | 5-OEt | N | OEt | OEt | |
| I-496 | H | 6-Cl | N | OEt | OEt | |
| I-497 | H | 5,6-(OMe)₂ | N | OEt | OEt | |
| I-498 | Me | 5-F | CH | OEt | OEt | 131–133 |
| I-499 | Me | 5-Cl | CH | OEt | OEt | 171–174 |
| I-500 | Me | 5-Br | CH | OEt | OEt | |
| I-501 | Me | 5-Me | CH | OEt | OEt | 119–122 |
| I-502 | Me | 5-CF₃ | CH | OEt | OEt | 131–134 |
| I-503 | Me | 5-OMe | CH | OEt | OEt | 141–144 |
| I-504 | Me | 5-OEt | CH | OEt | OEt | |

TABLE 16

| Compound No. | X | Yn | A | R¹ | R² | m.p. (° C.) or RI ($n_D^{20}$) |
|---|---|---|---|---|---|---|
| I-505 | Me | 5-OCF₃ | CH | OEt | OEt | |
| I-506 | Me | 5-CN | CH | OEt | OEt | |
| I-507 | Me | 6-F | CH | OEt | OEt | 133–134 |
| I-508 | Me | 6-Cl | CH | OEt | OEt | 146–149 |
| I-509 | Me | 6-Me | CH | OEt | OEt | |
| I-510 | Me | 6-CF₃ | CH | OEt | OEt | 138–141 |
| I-511 | Me | 6-OMe | CH | OEt | OEt | 135–138 |
| I-512 | Me | 5,6-(OMe)₂ | CH | OEt | OEt | |
| I-513 | Me | 5-F | N | OEt | OEt | |
| I-514 | Me | 5-Cl | N | OEt | OEt | 175–178 |
| I-515 | Me | 5-Br | N | OEt | OEt | 169–172 |
| I-516 | Me | 5-Me | N | OEt | OEt | 141–144 |
| I-517 | Me | 5-Bu-t | N | OEt | OEt | 107–109 |
| I-518 | Me | 5-CF₃ | N | OEt | OEt | |
| I-519 | Me | 5-OMe | N | OEt | OEt | |
| I-520 | Me | 5-OEt | N | OEt | OEt | |
| I-521 | Me | 5-OCF₃ | N | OEt | OEt | |
| I-522 | Me | 5-CN | N | OEt | OEt | |
| I-523 | Me | 6-F | N | OEt | OEt | |
| I-524 | Me | 6-Cl | N | OEt | OEt | |
| I-525 | Me | 6-Me | N | OEt | OEt | |
| I-526 | Me | 6-CF₃ | N | OEt | OEt | |
| I-527 | Me | 6-OMe | N | OEt | OEt | |
| I-528 | Me | 5,6-(OMe)₂ | N | OEt | OEt | |
| I-529 | Cl | 5-Cl | CH | OEt | OEt | |
| I-530 | Cl | 5-Me | CH | OEt | OEt | 101–103 |
| I-531 | Cl | 5-OMe | CH | OEt | OEt | 153–156 |
| I-532 | Cl | 5-OEt | CH | OEt | OEt | |
| I-533 | Cl | 5,6-(OMe)₂ | CH | OEt | OEt | |

TABLE 16-continued

| Compound No. | X | Yn | A | R¹ | R² | m.p. (° C.) or RI ($n_D^{20}$) |
|---|---|---|---|---|---|---|
| I-534 | Cl | 5-Cl | N | OEt | OEt | 130–133 |
| I-535 | Cl | 5-Me | N | OEt | OEt | |
| I-536 | Cl | 5-OMe | N | OEt | OEt | |
| I-537 | Cl | 5-OEt | N | OEt | OEt | |
| I-538 | Cl | 5,6-(OMe)₂ | N | OEt | OEt | |

TABLE 17

| Compound No. | X | Yn | A | R¹ | R² | m.p. (° C.) or RI ($n_D^{20}$) |
|---|---|---|---|---|---|---|
| I-539 | CF₃ | 5-Me | CH | OEt | OEt | |
| I-540 | CF₃ | 5-OMe | CH | OEt | OEt | |
| I-541 | CF₃ | 5,6-(OMe)₂ | CH | OEt | OEt | |
| I-542 | CF₃ | H | N | OEt | OEt | |
| I-543 | CF₃ | 5-Me | N | OEt | OEt | 163–165 |
| I-544 | CF₃ | 5-OMe | N | OEt | OEt | 140–143 |
| I-545 | CF₃ | 5-Cl | N | OEt | OEt | 138–141 |
| I-546 | CF₃ | 5-Br | N | OEt | OEt | 120–123 |
| I-547 | Et | 5-Me | CH | OEt | OEt | |
| I-548 | Et | 5-OMe | CH | OEt | OEt | |
| I-549 | Et | 5,6-(OMe)₂ | CH | OEt | OEt | |
| I-550 | CCl₃ | 5-Cl | N | OEt | OEt | 110–113 |
| I-551 | CCl₃ | 5-Br | N | OEt | OEt | |
| I-552 | CCl₃ | 5-Me | N | OEt | OEt | |
| I-553 | CCl₃ | 5-OMe | N | OEt | OEt | |
| I-554 | CF₂Cl | 5-Cl | N | OEt | OEt | |
| I-555 | CF₂Cl | 5-Br | N | OEt | OEt | |
| I-556 | CF₂Cl | 5-Me | N | OEt | OEt | |
| I-557 | CH₂Cl | 5-Cl | N | OEt | OEt | |
| I-558 | CH₂Cl | 5-Br | N | OEt | OEt | |
| I-559 | CH₂Cl | 5-Me | N | OEt | OEt | |
| I-560 | C₂F₅ | 5-Cl | N | OEt | OEt | |
| I-561 | C₂F₅ | 5-Br | N | OEt | OEt | |
| I-562 | C₂F₅ | 5-Me | N | OEt | OEt | |
| I-563 | CN | 5-Cl | CH | OEt | OEt | 170–172 |
| I-564 | CN | 5-OMe | CH | OEt | OEt | |
| I-565 | CN | 5,6-(OMe)₂ | CH | OEt | OEt | |
| I-566 | CN | 5-Me | N | OEt | OEt | |
| I-567 | CN | 5-OMe | N | OEt | OEt | |
| I-568 | CN | 5-Cl | N | OEt | OEt | |
| I-569 | SMe | 5-Cl | CH | OEt | OEt | 167–169 |
| I-570 | SMe | 5-Me | CH | OEt | OEt | |
| I-571 | SMe | 5-Cl | N | OEt | OEt | |
| I-572 | SMe | 5-Me | N | OEt | OEt | |

TABLE 18

| Compound No. | X | Yn | A | R¹ | R² | m.p. (° C.) or RI ($n_D^{20}$) |
|---|---|---|---|---|---|---|
| I-573 | SO₂Me | 5-Cl | CH | OEt | OEt | 167–170 |
| I-574 | SO₂Me | 5-Me | CH | OEt | OEt | |
| I-575 | OMe | 5-Cl | CH | OEt | OEt | 143–146 |
| I-576 | H | H | CH | OPr | OPr | 89–90 |
| I-577 | H | H | N | OPr | OPr | |
| I-578 | H | 5-Cl | N | OPr | OPr | |
| I-579 | H | 5-Br | N | OPr | OPr | |
| I-580 | Me | 5-Cl | N | OPr | OPr | 128–131 |
| I-581 | Me | 5-Br | N | OPr | OPr | |
| I-582 | Me | 5-Me | N | OPr | OPr | |
| I-583 | CF₃ | 5-Cl | N | OPr | OPr | 71–74 |
| I-584 | CF₃ | 5-Br | N | OPr | OPr | |
| I-585 | CF₃ | 5-Me | N | OPr | OPr | |
| I-586 | H | H | CH | OPr-i | OPr-i | 115–117 |
| I-587 | Me | 5-Cl | CH | OPr-i | OPr-i | |
| I-588 | Me | 5-Me | CH | OPr-i | OPr-i | |
| I-589 | H | H | N | OPr-i | OPr-i | |
| I-590 | H | 5-Cl | N | OPr-i | OPr-i | |
| I-591 | H | 5-Br | N | OPr-i | OPr-i | |
| I-592 | Me | 5-Cl | N | OPr-i | OPr-i | 85–88 |
| I-593 | Me | 5-Br | N | OPr-i | OPr-i | |
| I-594 | Me | 5-Me | N | OPr-i | OPr-i | |
| I-595 | CF₃ | 5-Cl | N | OPr-i | OPr-i | 97–100 |
| I-596 | CF₃ | 5-Br | N | OPr-i | OPr-i | |
| I-597 | CF₃ | 5-Me | N | OPr-i | OPr-i | |
| I-598 | H | H | N | OCH₂CH=CH₂ | OCH₂CH=CH₂ | |
| I-599 | H | 5-Cl | N | OCH₂CH=CH₂ | OCH₂CH=CH₂ | |
| I-600 | H | 5-Br | N | OCH₂CH=CH₂ | OCH₂CH=CH₂ | |
| I-601 | Me | 5-Cl | N | OCH₂CH=CH₂ | OCH₂CH=CH₂ | 158–161 |
| I-602 | Me | 5-Br | N | OCH₂CH=CH₂ | OCH₂CH=CH₂ | |
| I-603 | Me | 5-Me | N | OCH₂CH=CH₂ | OCH₂CH=CH₂ | |
| I-604 | CF₃ | 5-Cl | N | OCH₂CH=CH₂ | OCH₂CH=CH₂ | |
| I-605 | CF₃ | 5-Br | N | OCH₂CH=CH₂ | OCH₂CH=CH₂ | |
| I-606 | CF₃ | 5-Me | N | OCH₂CH=CH₂ | OCH₂CH=CH₂ | |

TABLE 19

| Compound No. | X | Yn | A | R¹ | R² | m.p. (° C.) or RI ($n_D^{20}$) |
|---|---|---|---|---|---|---|
| I-607 | H | H | N | OCH$_2$C≡CH | OCH$_2$C≡CH | |
| I-608 | H | 5-Cl | N | OCH$_2$C≡CH | OCH$_2$C≡CH | |
| I-609 | H | 5-Br | N | OCH$_2$C≡CH | OCH$_2$C≡CH | |
| I-610 | Me | 5-Cl | N | OCH$_2$C≡CH | OCH$_2$C≡CH | |
| I-611 | Me | 5-Br | N | OCH$_2$C≡CH | OCH$_2$C≡CH | |
| I-612 | Me | 5-Me | N | OCH$_2$C≡CH | OCH$_2$C≡CH | |
| I-613 | CF$_3$ | 5-Cl | N | OCH$_2$C≡CH | OCH$_2$C≡CH | |
| I-614 | CF$_3$ | 5-Br | N | OCH$_2$C≡CH | OCH$_2$C≡CH | |
| I-615 | CF$_3$ | 5-Me | N | OCH$_2$C≡CH | OCH$_2$C≡CH | |
| I-616 | Me | 5-Cl | CH | OCH$_2$CN | OCH$_2$CN | |
| I-617 | Me | 5-Me | CH | OCH$_2$CN | OCH$_2$CN | |
| I-618 | H | 5-Br | N | OCH$_2$CN | OCH$_2$CN | |
| I-619 | Me | 5-Cl | N | OCH$_2$CN | OCH$_2$CN | |
| I-620 | Me | 5-Br | N | OCH$_2$CN | OCH$_2$CN | |
| I-621 | Me | 5-Me | N | OCH$_2$CN | OCH$_2$CN | |
| I-622 | CF$_3$ | 5-Cl | N | OCH$_2$CN | OCH$_2$CN | |
| I-623 | CF$_3$ | 5-Br | N | OCH$_2$CN | OCH$_2$CN | |
| I-624 | CF$_3$ | 5-Me | N | OCH$_2$CN | OCH$_2$CN | |
| I-625 | Me | 5-Cl | CH | OCH$_2$CH$_2$OMe | OCH$_2$CH$_2$OMe | |
| I-626 | Me | 5-Me | CH | OCH$_2$CH$_2$OMe | OCH$_2$CH$_2$OMe | |
| I-627 | H | 5-Br | N | OCH$_2$CH$_2$OMe | OCH$_2$CH$_2$OMe | |
| I-628 | Me | 5-Cl | N | OCH$_2$CH$_2$OMe | OCH$_2$CH$_2$OMe | |
| I-629 | Me | 5-Br | N | OCH$_2$CH$_2$OMe | OCH$_2$CH$_2$OMe | |
| I-630 | Me | 5-Me | N | OCH$_2$CH$_2$OMe | OCH$_2$CH$_2$OMe | |
| I-631 | CF$_3$ | 5-Cl | N | OCH$_2$CH$_2$OMe | OCH$_2$CH$_2$OMe | |
| I-632 | CF$_3$ | 5-Br | N | OCH$_2$CH$_2$OMe | OCH$_2$CH$_2$OMe | |
| I-633 | CF$_3$ | 5-Me | N | OCH$_2$CH$_2$OMe | OCH$_2$CH$_2$OMe | |
| I-634 | H | 5-Br | N | OCH$_2$Pr-c | OCH$_2$Pr-c | |
| I-635 | Me | 5-Cl | N | OCH$_2$Pr-c | OCH$_2$Pr-c | |
| I-636 | Me | 5-Br | N | OCH$_2$Pr-c | OCH$_2$Pr-c | |
| I-637 | Me | 5-Me | N | OCH$_2$Pr-c | OCH$_2$Pr-c | |
| I-638 | CF$_3$ | 5-Cl | N | OCH$_2$Pr-c | OCH$_2$Pr-c | |
| I-639 | CF$_3$ | 5-Br | N | OCH$_2$Pr-c | OCH$_2$Pr-c | |
| I-640 | CF$_3$ | 5-Me | N | OCH$_2$Pr-c | OCH$_2$Pr-c | |

TABLE 20

| Compound No. | X | Yn | A | R¹ | R² | m.p. (° C.) or RI ($n_D^{20}$) |
|---|---|---|---|---|---|---|
| I-641 | Me | 5-Me | CH | OCH$_2$CH$_2$Cl | OCH$_2$CH$_2$Cl | |
| I-642 | Me | 5-Cl | CH | OCH$_2$CH$_2$Cl | OCH$_2$CH$_2$Cl | |
| I-643 | Me | 5-Me | N | OCH$_2$CH$_2$Cl | OCH$_2$CH$_2$Cl | |
| I-644 | Me | 5-Cl | N | OCH$_2$CH$_2$Cl | OCH$_2$CH$_2$Cl | |
| I-645 | CF$_3$ | 5-Me | N | OCH$_2$CH$_2$Cl | OCH$_2$CH$_2$Cl | |
| I-646 | CF$_3$ | 5-Cl | N | OCH$_2$CH$_2$Cl | OCH$_2$CH$_2$Cl | |
| I-647 | Me | 5-Cl | N | OCH$_2$CH$_2$F | OCH$_2$CH$_2$F | |
| I-648 | Me | 5-Me | N | OCH$_2$CH$_2$F | OCH$_2$CH$_2$F | |
| I-649 | CF$_3$ | 5-Me | N | OCH$_2$CH$_2$F | OCH$_2$CH$_2$F | |
| I-650 | CF$_3$ | 5-Cl | N | OCH$_2$CH$_2$F | OCH$_2$CH$_2$F | |
| I-651 | Me | 5-Cl | N | OCH$_2$CF$_3$ | OCH$_2$CF$_3$ | |
| I-652 | Me | 5-Me | N | OCH$_2$CF$_3$ | OCH$_2$CF$_3$ | |
| I-653 | CF$_3$ | 5-Me | N | OCH$_2$CF$_3$ | OCH$_2$CF$_3$ | |
| I-654 | CF$_3$ | 5-Cl | N | OCH$_2$CF$_3$ | OCH$_2$CF$_3$ | |
| I-655 | H | H | CH | OBn | OBn | |
| I-656 | H | H | N | OBn | OBn | |
| I-657 | H | H | N | OBn(4-Cl) | OBn(4-Cl) | |
| I-658 | H | H | N | OBn(4-Me) | OBn(4-Me) | |
| I-659 | H | H | N | OBn(4-OMe) | OBn(4-OMe) | |
| I-660 | H | H | CH | OMe | OPh | 131–132 |
| I-661 | H | H | N | OMe | OPh | |
| I-662 | H | H | N | OMe | OPh(4-Cl) | |
| I-663 | H | H | N | OMe | OPh(4-Me) | |
| I-664 | H | H | N | OMe | OPh(4-OMe) | |
| I-665 | H | H | CH | OMe | OCHF$_2$ | 138–139 |
| I-666 | H | H | N | OMe | OCHF$_2$ | |
| I-667 | H | H | CH | OMe | H | 114–116 |
| I-668 | Me | H | CH | OMe | H | |
| I-669 | H | 5-Cl | CH | OMe | H | 173–176 |
| I-670 | H | 5-Me | CH | OMe | H | 140–142 |
| I-671 | Me | 5-Cl | CH | OMe | H | 127–130 |
| I-672 | Me | 5-Me | CH | OMe | H | 113–114 |
| I-673 | Me | 5-CF$_3$ | CH | OMe | H | |
| I-674 | Me | 5-OMe | CH | OMe | H | |

TABLE 21

| Compound No. | X | Yn | A | R¹ | R² | m.p. (° C.) or RI ($n_D^{20}$) |
|---|---|---|---|---|---|---|
| I-675 | Me | 6-Cl | CH | OMe | H | 126–130 |
| I-676 | Me | 5,6-(OMe)$_2$ | CH | OMe | H | |
| I-677 | Cl | 5-Cl | CH | OMe | H | |
| I-678 | Cl | 5-Me | CH | OMe | H | |
| I-679 | Cl | 5-CF$_3$ | CH | OMe | H | |
| I-680 | Cl | 5-OMe | CH | OMe | H | |
| I-681 | Cl | 5,6-(OMe)$_2$ | CH | OMe | H | |
| I-682 | CF$_3$ | 5-Cl | CH | OMe | H | 107–108 |
| I-683 | CF$_3$ | 5-Me | CH | OMe | H | 76–79 |
| I-684 | CF$_3$ | 5-CF$_3$ | CH | OMe | H | |

TABLE 21-continued

| Compound No. | X | Yn | A | R¹ | R² | m.p. (° C.) or RI ($n_D^{20}$) |
|---|---|---|---|---|---|---|
| I-685 | CF₃ | 5-OMe | CH | OMe | H | |
| I-686 | Et | 5-Cl | CH | OMe | H | |
| I-687 | Et | 5-Me | CH | OMe | H | |
| I-688 | Et | 5-CF₃ | CH | OMe | H | |
| I-689 | Et | 5-OMe | CH | OMe | H | |
| I-690 | H | H | CH | OEt | H | 104–107 |
| I-691 | Me | H | CH | OEt | H | |
| I-692 | H | 5-Cl | CH | OEt | H | 158–160 |
| I-693 | H | 5-Me | CH | OEt | H | 131–132 |
| I-694 | Me | 5-Cl | CH | OEt | H | 153–155 |
| I-695 | Me | 5-Me | CH | OEt | H | 109–111 |
| I-696 | Me | 5-CF₃ | CH | OEt | H | |
| I-697 | Me | 5-OMe | CH | OEt | H | |
| I-698 | Me | 5,6-(OMe)₂ | CH | OEt | H | |
| I-699 | Me | 6-Cl | CH | OEt | H | 117–118 |
| I-700 | Cl | 5-Me | CH | OEt | H | |
| I-701 | Cl | 5-CF₃ | CH | OEt | H | |
| I-702 | Cl | 5-OMe | CH | OEt | H | |
| I-703 | Cl | 5,6-(OMe)₂ | CH | OEt | H | |
| I-704 | CF₃ | 5-Cl | CH | OEt | H | 125–128 |
| I-705 | CF₃ | 5-Me | CH | OEt | H | 86–87 |
| I-706 | CF₃ | 5-OMe | CH | OEt | H | |
| I-707 | Et | 5-Cl | CH | OEt | H | |
| I-708 | Et | 5-Me | CH | OEt | H | |

TABLE 22

| Compound No. | X | Yn | A | R¹ | R² | m.p. (° C.) or RI ($n_D^{20}$) |
|---|---|---|---|---|---|---|
| I-709 | Et | 5-CF₃ | CH | OEt | H | |
| I-710 | Et | 5-OMe | CH | OEt | H | |
| I-711 | H | H | CH | OPr | H | 83–86 |
| I-712 | Me | 5-Me | CH | OPr | H | |
| I-713 | Me | 5-Cl | CH | OPr | H | |
| I-714 | Me | 5-OMe | CH | OPr | H | |
| I-715 | H | H | CH | OCH₂CH=CH₂ | H | |
| I-716 | Me | 5-Me | CH | OCH₂CH=CH₂ | H | |
| I-717 | Me | 5-Cl | CH | OCH₂CH=CH₂ | H | |
| I-718 | Me | 5-OMe | CH | OCH₂CH=CH₂ | H | |
| I-719 | H | H | CH | OBn | H | |
| I-720 | Me | 5-Me | CH | OBn | H | |
| I-721 | Me | 5-Cl | CH | OBn | H | |
| I-722 | H | H | CH | OPh | H | 257–260 |
| I-723 | H | H | CH | OPh(4-Cl) | H | |
| I-724 | H | H | CH | OPh(4-Me) | H | |
| I-725 | H | H | CH | OPh(4-OMe) | H | |
| I-726 | H | H | CH | OMe | Me | 107–110 |
| I-727 | Me | H | CH | OMe | Me | |
| I-728 | H | 5-Cl | CH | OMe | Me | |
| I-729 | H | 5-Me | CH | OMe | Me | |
| I-730 | H | 5-CF₃ | CH | OMe | Me | |
| I-731 | Me | 5-Cl | CH | OMe | Me | 124–127 |
| I-732 | Me | 5-Me | CH | OMe | Me | |
| I-733 | Me | 5-CF₃ | CH | OMe | Me | |
| I-734 | Me | 5-OMe | CH | OMe | Me | |
| I-735 | Me | 6-Cl | CH | OMe | Me | |
| I-736 | Me | 5,6-(OMe)₂ | CH | OMe | Me | |
| I-737 | Cl | 5-Cl | CH | OMe | Me | |
| I-738 | Cl | 5-Me | CH | OMe | Me | |
| I-739 | Cl | 5-OMe | CH | OMe | Me | |
| I-740 | Cl | 5,6-(OMe)₂ | CH | OMe | Me | |
| I-741 | CF₃ | 5-Cl | CH | OMe | Me | |
| I-742 | CF₃ | 5-Me | CH | OMe | Me | |

TABLE 23

| Compound No. | X | Yn | A | R¹ | R² | m.p. (° C.) or RI ($n_D^{20}$) |
|---|---|---|---|---|---|---|
| I-743 | CF₃ | 5-OMe | CH | OMe | Me | |
| I-744 | Et | 5-Cl | CH | OMe | Me | |
| I-745 | Et | 5-Me | CH | OMe | Me | |
| I-746 | Et | 5-OMe | CH | OMe | Me | |
| I-747 | H | H | N | OMe | Me | |
| I-748 | H | 5-Cl | N | OMe | Me | |
| I-749 | H | 5-Me | N | OMe | Me | |
| I-750 | H | 5-CF₃ | N | OMe | Me | |
| I-751 | Me | 5-Cl | N | OMe | Me | |
| I-752 | Me | 5-Me | N | OMe | Me | 124–127 |
| I-753 | Me | 5-CF₃ | N | OMe | Me | |
| I-754 | Me | 5-OMe | N | OMe | Me | |
| I-755 | Me | 6-Cl | N | OMe | Me | |
| I-756 | Me | 5,6-(OMe)₂ | N | OMe | Me | |
| I-757 | Cl | 5-Cl | N | OMe | Me | |
| I-758 | Cl | 5-Me | N | OMe | Me | 117–120 |
| I-759 | Cl | 5-OMe | N | OMe | Me | |
| I-760 | Cl | 5,6-(OMe)₂ | N | OMe | Me | |
| I-761 | CF₃ | 5-Cl | N | OMe | Me | |
| I-762 | CF₃ | 5-Me | N | OMe | Me | 117–120 |
| I-763 | CF₃ | 5-OMe | N | OMe | Me | |
| I-764 | Et | 5-Cl | N | OMe | Me | |
| I-765 | Et | 5-Me | N | OMe | Me | |
| I-766 | Et | 5-OMe | N | OMe | Me | |
| I-767 | NH₂ | 5-Me | N | OMe | Me | >300 |

TABLE 23-continued

| Compound No. | X | Yn | A | R¹ | R² | m.p. (° C.) or RI ($n_D^{20}$) |
|---|---|---|---|---|---|---|
| I-768 | H | H | CH | OEt | Me | 57–60 |
| I-769 | Me | H | CH | OEt | Me | 92–94 |
| I-770 | CF₃ | H | CH | OEt | Me | |
| I-771 | Cl | H | CH | OEt | Me | 95–96 |
| I-772 | H | 5-Me | CH | OEt | Me | 105–108 |
| I-773 | Me | 5-F | CH | OEt | Me | |
| I-774 | Me | 5-Cl | CH | OEt | Me | |
| I-775 | Me | 5-Me | CH | OEt | Me | 108–110 |
| I-776 | Me | 5-CF₃ | CH | OEt | Me | |

TABLE 24

| Compound No. | X | Yn | A | R¹ | R² | m.p. (° C.) or RI ($n_D^{20}$) |
|---|---|---|---|---|---|---|
| I-777 | Me | 5-OMe | CH | OEt | Me | |
| I-778 | Me | 5-CN | CH | OEt | Me | |
| I-779 | Me | 6-Cl | CH | OEt | Me | |
| I-780 | Me | 5,6-(OMe)₂ | CH | OEt | Me | |
| I-781 | Cl | 5-Cl | CH | OEt | Me | |
| I-782 | Cl | 5-Me | CH | OEt | Me | |
| I-783 | Cl | 5-CF₃ | CH | OEt | Me | |
| I-784 | Cl | 5-OMe | CH | OEt | Me | |
| I-785 | Cl | 5,6-(OMe)₂ | CH | OEt | Me | |
| I-786 | CF₃ | 5-Cl | CH | OEt | Me | |
| I-787 | CF₃ | 5-Me | CH | OEt | Me | 117–118 |
| I-788 | CF₃ | 5-OMe | CH | OEt | Me | |
| I-789 | Et | 5-Cl | CH | OEt | Me | |
| I-790 | Et | 5-Me | CH | OEt | Me | |
| I-791 | Et | 5-CF₃ | CH | OEt | Me | |
| I-792 | Et | 5-OMe | CH | OEt | Me | |
| I-793 | H | H | N | OEt | Me | |
| I-794 | H | 5-Br | N | OEt | Me | |
| I-795 | Me | 5-Cl | N | OEt | Me | |
| I-796 | Me | 5-Br | N | OEt | Me | |
| I-797 | Me | 5-Me | N | OEt | Me | |
| I-798 | Me | 5-CF₃ | N | OEt | Me | |
| I-799 | Cl | 5-Cl | N | OEt | Me | |
| I-800 | Cl | 5-Me | N | OEt | Me | |
| I-801 | CF₃ | 5-Cl | N | OEt | Me | |
| I-802 | CF₃ | 5-Br | N | OEt | Me | |
| I-803 | CF₃ | 5-Me | N | OEt | Me | |
| I-804 | H | H | CH | OPr | Me | 47–50 |
| I-805 | H | 5-OMe | CH | OPr | Me | 100–102 |
| I-806 | Me | H | CH | OPr | Me | 75–78 |
| I-807 | CF₃ | H | CH | OPr | Me | |
| I-808 | H | 5-Cl | CH | OPr | Me | |
| I-809 | H | 5-Me | CH | OPr | Me | 73–76 |
| I-810 | Me | 5-F | CH | OPr | Me | |

TABLE 25

| Compound No. | X | Yn | A | R¹ | R² | m.p. (° C.) or RI ($n_D^{20}$) |
|---|---|---|---|---|---|---|
| I-811 | Me | 5-Cl | CH | OPr | Me | 90–93 |
| I-812 | Me | 5-Me | CH | OPr | Me | 59–62 |
| I-813 | Me | 5-OMe | CH | OPr | Me | 99–101 |
| I-814 | Me | 6-Cl | CH | OPr | Me | 109–112 |
| I-815 | Me | 5,6-(OMe)₂ | CH | OPr | Me | |
| I-816 | Cl | 5-Cl | CH | OPr | Me | |
| I-817 | Cl | 5-Me | CH | OPr | Me | 76–77 |
| I-818 | Cl | 5-OMe | CH | OPr | Me | 87–90 |
| I-819 | Cl | 5,6-(OMe)₂ | CH | OPr | Me | |
| I-820 | CF₃ | 5-Cl | CH | OPr | Me | |
| I-821 | CF₃ | 5-Me | CH | OPr | Me | |
| I-822 | CF₃ | 5-CF₃ | CH | OPr | Me | |
| I-823 | CF₃ | 5-OMe | CH | OPr | Me | |
| I-824 | Et | 5-Cl | CH | OPr | Me | |
| I-825 | Et | 5-Me | CH | OPr | Me | |
| I-826 | Et | 5-OMe | CH | OPr | Me | |
| I-827 | H | H | N | OPr | Me | |
| I-828 | H | 5-Br | N | OPr | Me | |
| I-829 | Me | 5-Cl | N | OPr | Me | |
| I-830 | Me | 5-Br | N | OPr | Me | |
| I-831 | Me | 5-Me | N | OPr | Me | 104–107 |
| I-832 | Me | 5-CF₃ | N | OPr | Me | |
| I-833 | Cl | 5-Cl | N | OPr | Me | |
| I-834 | Cl | 5-Me | N | OPr | Me | |
| I-835 | CF₃ | 5-Cl | N | OPr | Me | |
| I-836 | CF₃ | 5-Br | N | OPr | Me | |
| I-837 | CF₃ | 5-Me | N | OPr | Me | |
| I-838 | NH₂ | 5-Me | N | OPr | Me | 152–153 |
| I-839 | H | H | CH | OPr-i | Me | 66–68 |
| I-840 | Me | H | CH | OPr-i | Me | 1.5805 |
| I-841 | CF₃ | H | CH | OPr-i | Me | |
| I-842 | H | 5-Cl | CH | OPr-i | Me | |
| I-843 | H | 5-Me | CH | OPr-i | Me | |
| I-844 | Me | 5-F | CH | OPr-i | Me | |

TABLE 26

| Compound No. | X | Yn | A | R¹ | R² | m.p. (° C.) or RI ($n_D^{20}$) |
|---|---|---|---|---|---|---|
| I-845 | Me | 5-Cl | CH | OPr-i | Me | |
| I-846 | Me | 5-Me | CH | OPr-i | Me | |
| I-847 | Me | 5-OMe | CH | OPr-i | Me | |
| I-848 | Me | 6-Cl | CH | OPr-i | Me | |
| I-849 | Me | 5,6-(OMe)₂ | CH | OPr-i | Me | |
| I-850 | Cl | 5-Cl | CH | OPr-i | Me | |
| I-851 | Cl | 5-Me | CH | OPr-i | Me | |
| I-852 | Cl | 5-CF₃ | CH | OPr-i | Me | |
| I-853 | Cl | 5-OMe | CH | OPr-i | Me | |
| I-854 | Cl | 5,6-(OMe)₂ | CH | OPr-i | Me | |
| I-855 | CF₃ | 5-Cl | CH | OPr-i | Me | |
| I-856 | CF₃ | 5-Me | CH | OPr-i | Me | |
| I-857 | CF₃ | 5-OMe | CH | OPr-i | Me | |
| I-858 | Et | 5-Cl | CH | OPr-i | Me | |
| I-859 | Et | 5-Me | CH | OPr-i | Me | |
| I-860 | Et | 5-OMe | CH | OPr-i | Me | |
| I-861 | H | H | N | OPr-i | Me | |
| I-862 | H | 5-Br | N | OPr-i | Me | |
| I-863 | Me | 5-Cl | N | OPr-i | Me | |
| I-864 | Me | 5-Br | N | OPr-i | Me | |
| I-865 | Me | 5-Me | N | OPr-i | Me | |
| I-866 | Me | 5-CF₃ | N | OPr-i | Me | |
| I-867 | Cl | 5-Cl | N | OPr-i | Me | |
| I-868 | Cl | 5-Me | N | OPr-i | Me | |
| I-869 | CF₃ | 5-Cl | N | OPr-i | Me | |
| I-870 | CF₃ | 5-Br | N | OPr-i | Me | |
| I-871 | CF₃ | 5-Me | N | OPr-i | Me | |
| I-872 | H | H | CH | OBu | Me | 1.5795 |
| I-873 | Me | H | CH | OBu | Me | 73–76 |
| I-874 | Me | 5-Cl | CH | OBu | Me | |
| I-875 | Me | 5-Me | CH | OBu | Me | |
| I-876 | Me | 5-OMe | CH | OBu | Me | |
| I-877 | Cl | 5-Cl | CH | OBu | Me | |
| I-878 | Cl | 5-Me | CH | OBu | Me | |

TABLE 27

| Compound No. | X | Yn | A | R¹ | R² | m.p. (° C.) or RI ($n_D^{20}$) |
|---|---|---|---|---|---|---|
| I-879 | Cl | 5-OMe | CH | OBu | Me | |
| I-880 | CF₃ | 5-Cl | CH | OBu | Me | |
| I-881 | CF₃ | 5-Me | CH | OBu | Me | |
| I-882 | CF₃ | 5-OMe | CH | OBu | Me | |
| I-883 | H | H | CH | OCH₂CH=CH₂ | Me | 55–58 |
| I-884 | H | 5-Me | CH | OCH₂CH=CH₂ | Me | |
| I-885 | Me | H | CH | OCH₂CH=CH₂ | Me | 84–87 |
| I-886 | Me | 5-Cl | CH | OCH₂CH=CH₂ | Me | |
| I-887 | Me | 5-Me | CH | OCH₂CH=CH₂ | Me | |
| I-888 | Me | 5-OMe | CH | OCH₂CH=CH₂ | Me | |
| I-889 | Cl | 5-Cl | CH | OCH₂CH=CH₂ | Me | |
| I-890 | Cl | 5-Me | CH | OCH₂CH=CH₂ | Me | |
| I-891 | CF₃ | 5-Cl | CH | OCH₂CH=CH₂ | Me | |
| I-892 | CF₃ | 5-Me | CH | OCH₂CH=CH₂ | Me | |
| I-893 | CF₃ | 5-OMe | CH | OCH₂CH=CH₂ | Me | |
| I-894 | H | H | CH | OCH₂C≡CH | Me | 145–148 |
| I-895 | H | 5-Me | CH | OCH₂C≡CH | Me | 183–186 |
| I-896 | Me | H | CH | OCH₂C≡CH | Me | 147–149 |
| I-897 | Me | 5-Cl | CH | OCH₂C≡CH | Me | |
| I-898 | Me | 5-Me | CH | OCH₂C≡CH | Me | 147–150 |
| I-899 | Me | 5-OMe | CH | OCH₂C≡CH | Me | |
| I-900 | Cl | 5-Cl | CH | OCH₂C≡CH | Me | |
| I-901 | Cl | 5-Me | CH | OCH₂C≡CH | Me | |
| I-902 | CF₃ | 5-Cl | CH | OCH₂C≡CH | Me | |
| I-903 | CF₃ | 5-Me | CH | OCH₂C≡CH | Me | 113–116 |
| I-904 | NH₂ | 5-Me | CH | OCH₂C≡CH | Me | 225–228 |
| I-905 | H | H | CH | OBn | Me | |
| I-906 | H | H | CH | OPn-c | Me | 1.5965 |
| I-907 | Me | H | CH | OPn-c | Me | 1.5941 |
| I-908 | Me | 5-Cl | CH | OPn-c | Me | |
| I-909 | Me | 5-Cl | N | OPn-c | Me | |
| I-910 | H | H | CH | SMe | Me | |
| I-911 | Me | H | CH | SMe | Me | 139–142 |
| I-912 | Me | 5-Me | CH | SMe | Me | |

TABLE 28

| Compound No. | X | Yn | A | R¹ | R² | m.p. (° C.) or RI ($n_D^{20}$) |
|---|---|---|---|---|---|---|
| I-913 | Me | 5-Cl | CH | SMe | Me | |
| I-914 | H | H | N | SMe | Me | |
| I-915 | Me | 5-Me | N | SMe | Me | 134–137 |
| I-916 | Me | 5-Cl | N | SMe | Me | |
| I-917 | H | H | CH | OMe | Et | |
| I-918 | Me | 5-Me | CH | OMe | Et | |
| I-919 | Me | 5-Cl | CH | OMe | Et | |
| I-920 | Me | 5-CF₃ | CH | OMe | Et | |
| I-921 | Me | 5-OMe | CH | OMe | Et | |
| I-922 | Cl | 5-Me | CH | OMe | Et | |
| I-923 | Cl | 5-Cl | CH | OMe | Et | |
| I-924 | H | H | CH | OEt | Et | |
| I-925 | Me | 5-Me | CH | OEt | Et | |
| I-926 | Me | 5-Cl | CH | OEt | Et | |
| I-927 | Me | 5-CF₃ | CH | OEt | Et | |
| I-928 | Me | 5-OMe | CH | OEt | Et | |
| I-929 | Cl | 5-Me | CH | OEt | Et | |
| I-930 | Cl | 5-Cl | CH | OEt | Et | |
| I-931 | H | H | CH | OPr | Et | |
| I-932 | Me | 5-Me | CH | OPr | Et | |
| I-933 | Me | 5-Cl | CH | OPr | Et | |
| I-934 | Me | 5-CF₃ | CH | OPr | Et | |
| I-935 | Me | 5-OMe | CH | OPr | Et | |
| I-936 | Cl | 5-Me | CH | OPr | Et | |
| I-937 | Cl | 5-Cl | CH | OPr | Et | |
| I-938 | H | H | N | OMe | Et | |
| I-939 | H | 5-Br | N | OMe | Et | 125–128 |
| I-940 | Me | 5-Me | N | OMe | Et | |
| I-941 | Me | 5-Cl | N | OMe | Et | 134–137 |

TABLE 28-continued

| Compound No. | X | Yn | A | R¹ | R² | m.p. (° C.) or RI ($n_D^{20}$) |
|---|---|---|---|---|---|---|
| I-942 | Me | 5-Br | N | OMe | Et | 134–141 |
| I-943 | Cl | 5-Me | N | OMe | Et | |
| I-944 | Cl | 5-Cl | N | OMe | Et | |
| I-945 | CF₃ | 5-Me | N | OMe | Et | 86–89 |
| I-946 | CF₃ | 5-Cl | N | OMe | Et | 79–82 |

TABLE 29

| Compound No. | X | Yn | A | R¹ | R² | m.p. (° C.) or RI ($n_D^{20}$) |
|---|---|---|---|---|---|---|
| I-947 | CF₃ | 5-Br | N | OMe | Et | 97–100 |
| I-948 | H | H | N | OEt | Et | |
| I-949 | H | 5-Br | N | OEt | Et | 79–82 |
| I-950 | Me | 5-Me | N | OEt | Et | |
| I-951 | Me | 5-Cl | N | OEt | Et | |
| I-952 | Me | 5-Br | N | OEt | Et | 96–98 |
| I-953 | Cl | 5-Me | N | OEt | Et | |
| I-954 | Cl | 5-Cl | N | OEt | Et | |
| I-955 | CF₃ | 5-Me | N | OEt | Et | |
| I-956 | CF₃ | 5-Cl | N | OEt | Et | 66–67 |
| I-957 | CF₃ | 5-Br | N | OEt | Et | 97–100 |
| I-958 | H | H | CH | OMe | Pr | 78–80 |
| I-959 | Me | H | CH | OMe | Pr | 1.5892 |
| I-960 | Cl | H | CH | OMe | Pr | 1.6009 |
| I-961 | H | 5-Cl | CH | OMe | Pr | |
| I-962 | H | 5-Me | CH | OMe | Pr | 116–119 |
| I-963 | Me | 5-F | CH | OMe | Pr | |
| I-964 | Me | 5-Cl | CH | OMe | Pr | 113–116 |
| I-965 | Me | 5-Me | CH | OMe | Pr | 105–107 |
| I-966 | Me | 5-OMe | CH | OMe | Pr | |
| I-967 | Me | 6-Cl | CH | OMe | Pr | 68–71 |
| I-968 | Cl | 5-Cl | CH | OMe | Pr | |
| I-969 | Cl | 5-Me | CH | OMe | Pr | |
| I-970 | Cl | 5-OMe | CH | OMe | Pr | |
| I-971 | CF₃ | 5-Cl | CH | OMe | Pr | |
| I-972 | CF₃ | 5-Me | CH | OMe | Pr | |
| I-973 | CF₃ | 5-OMe | CH | OMe | Pr | |
| I-974 | H | H | CH | OEt | Pr | |
| I-975 | H | 5-Cl | CH | OEt | Pr | |
| I-976 | H | 5-Me | CH | OEt | Pr | |
| I-977 | Me | 5-F | CH | OEt | Pr | |
| I-978 | Me | 5-Cl | CH | OEt | Pr | |
| I-979 | Me | 5-Me | CH | OEt | Pr | |
| I-980 | Me | 5-CF₃ | CH | OEt | Pr | |

TABLE 30

| Compound No. | X | Yn | A | R¹ | R² | m.p. (° C.) or RI ($n_D^{20}$) |
|---|---|---|---|---|---|---|
| I-981 | Me | 5-OMe | CH | OEt | Pr | |
| I-982 | Cl | 5-Cl | CH | OEt | Pr | |
| I-983 | Cl | 5-Me | CH | OEt | Pr | |
| I-984 | Cl | 5-CF₃ | CH | OEt | Pr | |
| I-985 | Cl | 5-OMe | CH | OEt | Pr | |
| I-986 | CF₃ | 5-Cl | CH | OEt | Pr | |
| I-987 | CF₃ | 5-Me | CH | OEt | Pr | |
| I-988 | CF₃ | 5-OMe | CH | OEt | Pr | |
| I-989 | H | H | CH | OPr | Pr | |
| I-990 | Me | 5-Me | CH | OPr | Pr | |
| I-991 | Me | 5-Cl | CH | OPr | Pr | |
| I-992 | Me | 5-OMe | CH | OPr | Pr | |
| I-993 | Cl | 5-Me | CH | OPr | Pr | |
| I-994 | Cl | 5-Cl | CH | OPr | Pr | |

TABLE 30-continued

| Compound No. | X | Yn | A | R¹ | R² | m.p. (° C.) or RI ($n_D^{20}$) |
|---|---|---|---|---|---|---|
| I-995 | H | H | N | OMe | Pr | |
| I-996 | H | 5-Br | N | OMe | Pr | |
| I-997 | Me | 5-Cl | N | OMe | Pr | |
| I-998 | Me | 5-Br | N | OMe | Pr | |
| I-999 | Me | 5-Me | N | OMe | Pr | 112–115 |
| I-1000 | Cl | 5-Cl | N | OMe | Pr | |
| I-1001 | Cl | 5-Me | N | OMe | Pr | |
| I-1002 | CF₃ | 5-Cl | N | OMe | Pr | |
| I-1003 | CF₃ | 5-Br | N | OMe | Pr | |
| I-1004 | CF₃ | 5-Me | N | OMe | Pr | 92–95 |
| I-1005 | H | H | N | OEt | Pr | |
| I-1006 | H | 5-Br | N | OEt | Pr | |
| I-1007 | Me | 5-Cl | N | OEt | Pr | |
| I-1008 | Me | 5-Br | N | OEt | Pr | |
| I-1009 | Me | 5-Me | N | OEt | Pr | |
| I-1010 | Cl | 5-Cl | N | OEt | Pr | |
| I-1011 | Cl | 5-Me | N | OPr | Pr | |
| I-1012 | CF₃ | 5-Cl | N | OPr | Pr | |
| I-1013 | CF₃ | 5-Br | N | OPr | Pr | |
| I-1014 | CF₃ | 5-Me | N | OPr | Pr | |

TABLE 31

| Compound No. | X | Yn | A | R¹ | R² | m.p. (° C.) or RI ($n_D^{20}$) |
|---|---|---|---|---|---|---|
| I-1015 | H | H | N | OMe | Pr-c | |
| I-1016 | H | 5-Br | N | OMe | Pr-c | 154–157 |
| I-1017 | Me | 5-Cl | N | OMe | Pr-c | 116–119 |
| I-1018 | Me | 5-Br | N | OMe | Pr-c | 121–124 |
| I-1019 | Me | 5-Me | N | OMe | Pr-c | 167–170 |
| I-1020 | CF₃ | 5-Cl | N | OMe | Pr-c | 101–104 |
| I-1021 | CF₃ | 5-Br | N | OMe | Pr-c | 119–122 |
| I-1022 | CF₃ | 5-Me | N | OMe | Pr-c | 116–119 |
| I-1023 | H | H | N | OEt | Pr-c | |
| I-1024 | H | 5-Br | N | OEt | Pr-c | 137–140 |
| I-1025 | Me | 5-Cl | N | OEt | Pr-c | 130–133 |
| I-1026 | Me | 5-Br | N | OEt | Pr-c | 124–127 |
| I-1027 | Me | 5-Me | N | OEt | Pr-c | 131–133 |
| I-1028 | CF₃ | 5-Cl | N | OEt | Pr-c | 82–85 |
| I-1029 | CF₃ | 5-Br | N | OEt | Pr-c | 105–108 |
| I-1030 | CF₃ | 5-Me | N | OEt | Pr-c | 79–82 |
| I-1031 | H | H | N | SMe | Pr-c | |
| I-1032 | H | 5-Br | N | SMe | Pr-c | |
| I-1033 | Me | 5-Cl | N | SMe | Pr-c | |
| I-1034 | Me | 5-Br | N | SMe | Pr-c | |
| I-1035 | Me | 5-Me | N | SMe | Pr-c | |
| I-1036 | CF₃ | 5-Cl | N | SMe | Pr-c | |
| I-1037 | CF₃ | 5-Br | N | SMe | Pr-c | |
| I-1038 | CF₃ | 5-Me | N | SMe | Pr-c | |
| I-1039 | Me | H | CH | SMe | SMe | 129–131 |
| I-1040 | H | 5-Cl | N | SMe | SMe | |
| I-1041 | H | 5-Br | N | SMe | SMe | |
| I-1042 | Me | H | N | SMe | SMe | 176–179 |
| I-1043 | Me | 5-Cl | N | SMe | SMe | 186–189 |
| I-1044 | Me | 5-Br | N | SMe | SMe | |
| I-1045 | Me | 5-Me | N | SMe | SMe | |
| I-1046 | CF₃ | 5-Cl | N | SMe | SMe | 144–146 |
| I-1047 | CF₃ | 5-Br | N | SMe | SMe | |
| I-1048 | CF₃ | 5-Me | N | SMe | Me | 106–109 |

TABLE 32

| Compound No. | X | Yn | A | R¹ | R² | m.p. (° C.) or RI ($n_D^{20}$) |
|---|---|---|---|---|---|---|
| I-1049 | H | 5-Br | N | OMe | SMe | |
| I-1050 | Me | 5-Cl | N | OMe | SMe | |
| I-1051 | Me | 5-Br | N | OMe | SMe | |
| I-1052 | Me | 5-Me | N | OMe | SMe | |
| I-1053 | CF₃ | 5-Cl | N | OMe | SMe | |
| I-1054 | CF₃ | 5-Br | N | OMe | SMe | |
| I-1055 | CF₃ | 5-Me | N | OMe | SMe | |
| I-1056 | H | H | CH | OMe | Ph | 160–162 |
| I-1057 | H | H | N | OMe | Ph | |
| I-1058 | Me | 5-Me | N | OMe | Ph | 165–168 |
| I-1059 | CF₃ | 6-Me | N | OMe | Ph | 150–153 |
| I-1060 | H | H | CH | Cl | Ph | 176–179 |
| I-1061 | H | H | N | Cl | Ph | |
| I-1062 | H | H | CH | Cl | Cl | 165–168 |
| I-1063 | Me | H | CH | Cl | Cl | 170–172 |
| I-1064 | Me | 5,6-Cl₂ | CH | Cl | Cl | 202–205 |
| I-1065 | H | H | N | Cl | Cl | |
| I-1066 | Me | H | N | Cl | Cl | >300 |
| I-1067 | H | H | CH | Cl | Me | 187–190 |
| I-1068 | Me | H | CH | Cl | Me | 122–125 |
| I-1069 | H | H | CH | Cl | N(Me)₂ | 205–208 |
| I-1070 | H | H | N | Cl | N(Me)₂ | |
| I-1071 | Me | 5-Cl | N | N(Me)₂ | N(Me)₂ | 203–206 |
| I-1072 | H | H | N | OMe | N(Me)₂ | 129–132 |
| I-1073 | H | H | CBr | OMe | OMe | >300 |
| I-1074 | H | H | CMe | OMe | OMe | 152–155 |
| I-1075 | H | H | CMe | Cl | Cl | 184–187 |
| I-1076 | H | H | COMe | H | H | 131–134 |
| I-1077 | Me | 5-Me | COMe | H | H | |
| I-1078 | Me | 5-Cl | COMe | H | H | |
| I-1079 | H | H | CH | Me | Me | 131–132 |
| I-1080 | Me | 5-Cl | CH | Me | Me | 138–140 |
| I-1081 | Me | 5-CF₃ | CH | Me | Me | |
| I-1082 | H | H | CH | Me | CF₃ | 107–110 |

TABLE 33

| Compound No. | X | Yn | A | R¹ | R² | m.p. (° C.) or RI ($n_D^{20}$) |
|---|---|---|---|---|---|---|
| I-1083 | Me | 5-Cl | CH | Me | CF₃ | |
| I-1084 | Me | 5-Cl | N | Me | CF₃ | |
| I-1085 | H | H | CH | Me | Et | 60–63 |
| I-1086 | H | 5-Me | CH | Me | Et | 55–58 |
| I-1087 | Me | 5-Me | CH | Me | Et | 109–112 |
| I-1088 | Me | 5-Cl | CH | Me | Et | 76–79 |
| I-1089 | Me | 5-OMe | CH | Me | Et | |
| I-1090 | Me | 6-Cl | CH | Me | Et | 84–87 |
| I-1091 | Cl | 5-Cl | CH | Me | Et | |
| I-1092 | Cl | 5-Me | CH | Me | Et | |
| I-1093 | H | H | CH | Et | Et | 58–61 |
| I-1094 | H | 5-Me | CH | Et | Et | 68–71 |
| I-1095 | Me | 5-Me | CH | Et | Et | 76–79 |
| I-1096 | Me | 5-Cl | CH | Et | Et | 78–80 |
| I-1097 | Me | 5-OMe | CH | Et | Et | |
| I-1098 | Me | 6-Cl | CH | Et | Et | 80–83 |
| I-1099 | Cl | 5-Cl | CH | Et | Et | |
| I-1100 | Cl | 5-Me | CH | Et | Et | |
| I-1101 | H | H | CH | Me | Pr-c | 124–125 |
| I-1102 | H | 5-Me | CH | Me | Pr-c | |
| I-1103 | Me | 5-Me | CH | Me | Pr-c | 153–156 |
| I-1104 | Me | 5-Cl | CH | Me | Pr-c | 119–122 |
| I-1105 | Me | 5-OMe | CH | Me | Pr-c | |
| I-1106 | Me | 6-Cl | CH | Me | Pr-c | 110–113 |
| I-1107 | Cl | 5-Cl | CH | Me | Pr-c | |
| I-1108 | Cl | 5-Me | CH | Me | Pr-c | |
| I-1109 | H | H | CH | Et | Pr-c | |
| I-1110 | Me | 5-Me | CH | Et | Pr-c | |
| I-1111 | Me | 5-Cl | CH | Et | Pr-c | |

TABLE 33-continued

| Compound No. | X | Yn | A | R¹ | R² | m.p. (° C.) or RI ($n_D^{20}$) |
|---|---|---|---|---|---|---|
| I-1112 | Me | 5-OMe | CH | Et | Pr-c | |
| I-1113 | Me | 6-Cl | CH | Et | Pr-c | |
| I-1114 | Cl | 5-Cl | CH | Et | Pr-c | |
| I-1115 | Cl | 5-Me | CH | Et | Pr-c | |
| I-1116 | H | H | CH | Et | Et | |

TABLE 34

| Compound No. | X | Yn | A | R¹ | R² | m.p. (° C.) or RI ($n_D^{20}$) |
|---|---|---|---|---|---|---|
| I-1117 | Me | 5-Me | CH | Et | Et | |
| I-1118 | Me | 5-Cl | CH | Et | Et | |
| I-1119 | Me | 5-OMe | CH | Et | Et | |
| I-1120 | Me | 6-Cl | CH | Et | Et | |
| I-1121 | Cl | 5-Cl | CH | Et | Et | |
| I-1122 | Cl | 5-Me | CH | Et | Et | |
| I-1123 | H | H | CH | C≡CMe | Me | 134–136 |
| I-1124 | Me | 5-Me | CH | C≡CMe | Me | |
| I-1125 | Me | 5-Cl | CH | C≡CMe | Me | |
| I-1126 | Me | 5-Me | N | C≡CMe | Me | |
| I-1127 | Me | 5-Cl | N | C≡CMe | Me | |
| I-1128 | Cl | 5-Cl | CH | C≡CMe | Me | |
| I-1129 | Cl | 5-Me | CH | C≡CMe | Me | |
| I-1130 | H | H | CH | CH=CH₂ | Me | |
| I-1131 | Me | 5-Me | CH | CH=CH₂ | Me | |
| I-1132 | Me | 5-Cl | CH | CH=CH₂ | Me | |
| I-1133 | Me | 5-Me | N | CH=CH₂ | Me | |
| I-1134 | Cl | 5-Cl | CH | CH=CH₂ | Me | |
| I-1135 | Cl | 5-Me | CH | CH=CH₂ | Me | |
| I-1136 | H | H | CH | CHO | Me | |
| I-1137 | Me | 5-Cl | CH | CHO | Me | |
| I-1138 | Me | 5-Cl | N | CHO | Me | |
| I-1139 | H | H | CH | COMe | Me | |
| I-1140 | Me | 5-Cl | CH | COMe | Me | |
| I-1141 | Me | 5-Cl | N | COMe | Me | |
| I-1142 | H | H | CH | CH₂OMe | Me | |
| I-1143 | Me | 5-Cl | CH | CH₂OMe | Me | |
| I-1144 | Me | 5-Me | CH | CH₂OMe | Me | |
| I-1145 | H | H | N | CH₂OMe | OMe | |
| I-1146 | Me | H | CH | CN | CN | |
| I-1147 | Me | H | CH | CN | Me | 187–189 |
| I-1148 | Me | H | N | CN | CN | |
| I-1149 | Me | H | N | CN | Me | |
| I-1150 | Me | H | CH | SO₂Me | SO₂Me | |

TABLE 35

| Compound No. | X | Yn | A | R¹ | R² | m.p. (° C.) or RI ($n_D^{20}$) |
|---|---|---|---|---|---|---|
| I-1151 | Me | H | N | SO₂Me | SO₂Me | |
| I-1152 | Me | H | CH | SO₂Me | Me | 183–186 |

Typical processes for producing pyrimidinylbenzimidazole and triazinylbenzimidazole derivatives represented by the general formula [I] as the compounds of the present invention, will be exemplified below.

Process 1

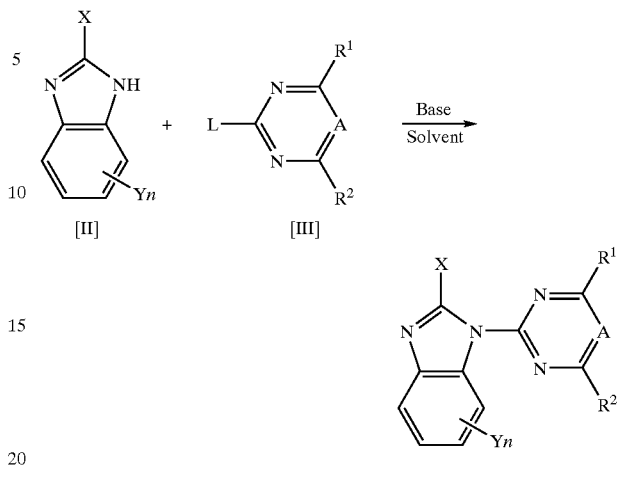

(wherein X, Y, R¹, R², A and n have the same meanings as mentioned above respectively, and L is a leaving group such as a halogen atom, a ($C_1$–$C_6$) alkylsulfonyl group or a benzylsulfonyl group.)

The compound of the present invention represented by the general formula [I] can be produced by reacting a benzimidazole derivative represented by the general formula [II] and a pyrimidine derivative or triazine derivative represented by the general formula [III] in the presence of a base in a solvent. Here, as the base, a carbonate, hydrogencarbonate, acetate, alcoholate, hydroxide, hydride or oxide of an alkali metal or alkaline earth metal, particularly sodium, potassium, magnesium or calcium, may, for example, be used. The solvent which can be used in the present reaction may be one which does not inhibit the progress of the present reaction, and an ether such as diethyl ether, diisopropyl ether, tetrahydrofuran, dioxane, monoglyme or diglyme, a halogenated hydrocarbon such as dichloroethane, chloroform, carbon tetrachloride or tetrachloroethane, an aromatic hydrocarbon such as benzene, chlorobenzene, nitrobenzene or toluene, or N,N-dimethylformamide, N,N-dimethylacetoamide, 1,3-dimethyl-2-imidazolinone or dimethylsulfoxide, may, for example, be used. These inert solvents may be used alone or as mixed. The reaction temperature may be selected within a range of from −20° C. to the boiling point of the inert solvent to be used, and preferably within a range of from 0° C. to 80° C. The reaction time varies depending upon e.g. the reaction temperature and the reaction amount, but may be selected within a range of from 1 hour to 48 hours in general. After completion of the reaction, the desired product is isolated from the reaction system by a conventional method and may be purified by e.g. column chromatography or recrystallization, as the case requires.

Here, the benzimidazole derivative represented by the general formula [II] may be a commercially available product or may be produced by a known method [e.g. a method as disclosed in Angewandte Chemie, vol 85, p866 (1973); Journal of the American Chemical Society, vol 69, p2459 (1947); Journal of the American Chemical Society, vol 82, p3138 (1960); Organic Syntheses, vol 2, p65 (1943); or Organic Syntheses, vol 4, p569 (1963)].

Process 2

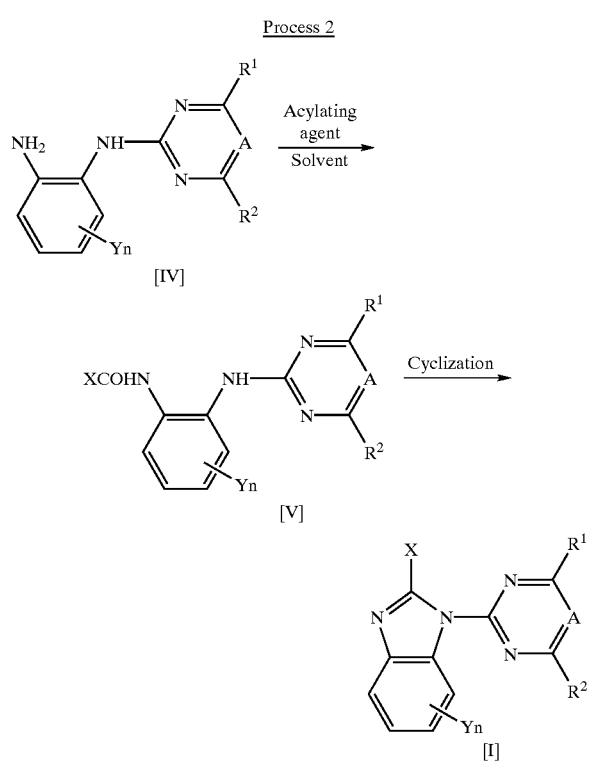

(wherein X, Y, $R^1$, $R^2$, A and n have the same meanings as mentioned above respectively.)

The anilide derivative represented by the general formula [V] can be produced by reacting an anilinopyrimidine derivative or anilinotriazine derivative represented by the general formula [IV] with an acylating agent in an inert solvent. The reaction is carried out preferably in the presence of a base. As the acylating agent, an acid halide such as acetyl chloride, propionyl chloride or benzoyl chloride, or an acid anhydride such as trifluoroacetic anhydride, propionic anhydride or benzoic anhydride may be mentioned. The inert solvent which can be used in the present reaction may be one which does not inhibit the progress of the present reaction, and for example, e.g. a ketone such as acetone, methyl ethyl ketone or cyclohexanone, an ether such as diethyl ether, diisopropyl ether, tetrahydrofuran, dioxane, monoglyme or diglyme, an ester such as ethyl acetate or methyl acetate, a halogenated hydrocarbon such as dichloroethane, chloroform, carbon tetrachloride or tetrachloroethane, an aromatic hydrocarbon such as benzene, chlorobenzene, nitrobenzene or toluene, a nitrile such as acetonitrile, or N,N-dimethylformamide, N,N-dimethylacetoamide, 1,3-dimethyl-2-imidazolinone, dimethylsulfoxide, pyridine or water, may be used. These inert solvents may be used alone or as mixed. As the base to be used in the present reaction, an inorganic base or an organic base may be used. For example, as an inorganic base, a carbonate or hydroxide of an alkali metal or alkaline earth metal, such as sodium carbonate, potassium carbonate, calcium carbonate, sodium hydrogencarbonate, sodium hydroxide, potassium hydroxide or calcium hydroxide, or a hydride of an alkali metal such as lithium hydride or sodium hydride, may be used, and as an organic base, triethylamine, diisopropylethylamine or pyridine may, for example, be used. The reaction temperature may be selected within a range of from −20° C. to the boiling point of the inert solvent to be used, and preferably within a range of from 0° C. to 50° C. The reaction time varies depending upon e.g. the reaction temperature and the reaction amount, but may be selected within a range of from several minutes to 48 hours in general.

Then, the anilide derivative represented by the general formula [V] is subjected to a cyclization reaction without a solvent or in a solvent, in the presence of a catalyst as the case requires, to produce the compound of the present invention represented by the general formula [I]. As the catalyst to be used here, an inorganic acid such as sulfuric acid or hydrochloric acid or an organic acid such as para-toluenesulfonic acid may, for example, be used. As the solvent which can be used in the present reaction, the solvent exemplified in Process 1 may be used. The reaction temperature may be selected within a range of from 0° C. to the boiling point of the solvent to be used, and preferably within a range of from room temperature to the boiling point of the solvent. The reaction time varies depending upon e.g. the reaction temperature and the reaction amount, but may be selected within a range of from 1 hour to 48 hours in general. After the completion of the reaction, the desired product is isolated from the reaction system by a conventional method and may be purified by e.g. column chromatography or recrystallization, as the case requires.

Process 3

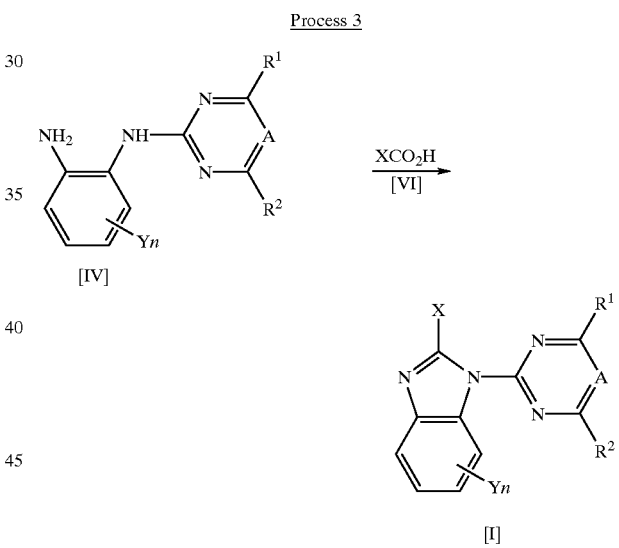

(wherein X, Y, $R^1$, $R^2$, A and n have the same meanings as mentioned above respectively.)

The compound of the present invention represented by the general formula [I] can be produced directly by heating an anilinopyrimidine derivative or anilinotriazine derivative represented by the general formula [IV] in a carboxylic acid represented by the general formula [VI], in the presence of an acid anhydride as the case requires. The reaction temperature may be selected within a range of from 0° C. to the boiling point of the carboxylic acid to be used, preferably within a range of from room temperature to the boiling point of the carboxylic acid. The reaction time may be selected within a range of from 1 hour to 48 hours in general. After the completion of the reaction, the desired product is isolated from the reaction system by a conventional method and may be purified by e.g. column chromatography or recrystallization, as the case requires.

Process 4

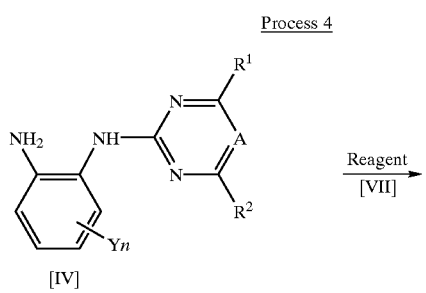

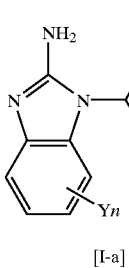

[I-a]

(wherein Y, $R^1$, $R^2$, A and n have the same meanings as mentioned above respectively.)

The compound represented by the general formula [I-a] can be produced by reacting an anilinopyrimidine derivative or anilinotriazine derivative represented by the general formula [IV] and a reagent [VII] such as BrCN or $H_2NCN$ by a method known from a literature [e.g. a method as disclosed in Journal of the American Chemical Society, vol 69, p2459 (1947); or Angewandte Chemie, vol 85, p866 (1973)] in a solvent. As the solvent which can be used in the present reaction, the solvent as exemplified in Process 1 may be used. The reaction temperature may be selected within a range of from −20° C. to the boiling point of the reaction mixture to be used, preferably within a range of from 0° C. to the boiling point of the reaction mixture. The reaction time varies depending upon e.g. the reaction temperature or the reaction amount, and may be selected within a range of from 1 hour to 48 hours in general. After the completion of the reaction, the desired product is isolated from the reaction system by a conventional method and may be purified by e.g. column chromatography or recrystallization, as the case requires.

Process 5

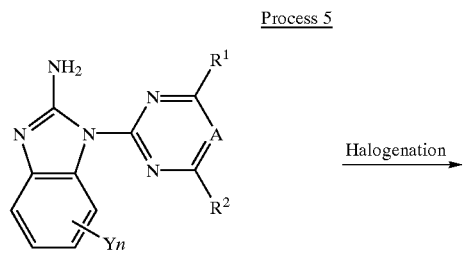

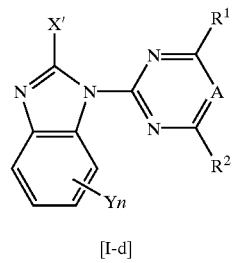

[I-d]

(wherein X' is a halogen atom, and Y, $R^1$, $R^2$, A and n have the same meanings as mentioned above respectively.)

The compound represented by the general formula [I-d] can be produced by diazotizing a 2-aminobenzimidazole derivative represented by the general formula [I-a] by a known method [e.g. Sandmeyer method, Schwechten method or Gattermann method] in a solvent at a reaction temperature which are conventionally employed, followed by halogenation. After the completion of the reaction, the desired product is isolated from the reaction system by a conventional method and may be purified by e.g. column chromatography or recrystallization, as the case requires.

Process 6

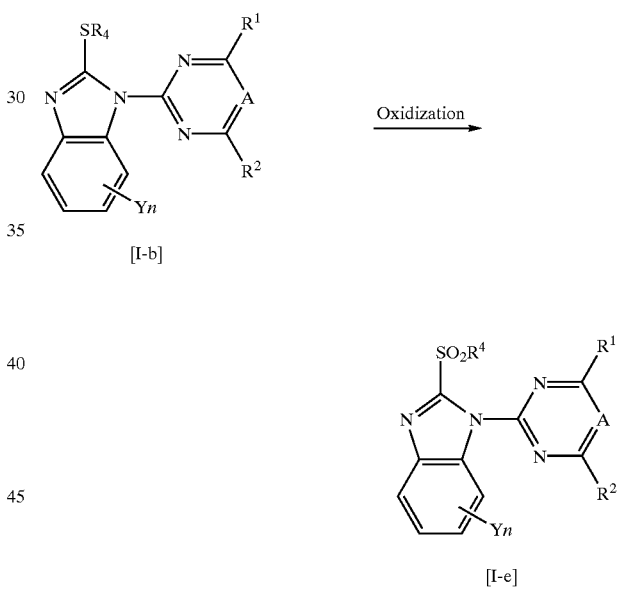

(wherein Y, $R^1$, $R^2$, A and n have the same meanings as mentioned above respectively, and $R^4$ is a $C_1$–$C_6$ alkyl group.)

The compound represented by the general formula [I-e] can be produced by oxidizing a pyrimidinylbenzimidazole derivative or triazinylbenzimidazole derivative represented by the general formula [I-b] by a known method. After the completion of the reaction, the desired product is isolated from the reaction system by a conventional method and may be purified by e.g. column chromatography or recrystallization, as the case requires. The oxidizing agent which can be used in the present reaction may, for example, be hydrogen peroxide or an organic peracid such as m-chloroperbenzoic acid. As the solvent which can be used, the solvent as exemplified in Process 1 may be used. The reaction temperature may be selected within a range of from −20° C. to the boiling point of the reaction mixture to be used, preferably within a range of from 5° C. to the boiling point of the reaction mixture. After the completion of the reaction, the desired product is isolated from the reaction system by a conventional method and may be purified by e.g. column chromatography or recrystallization, as the case requires.

Process 7

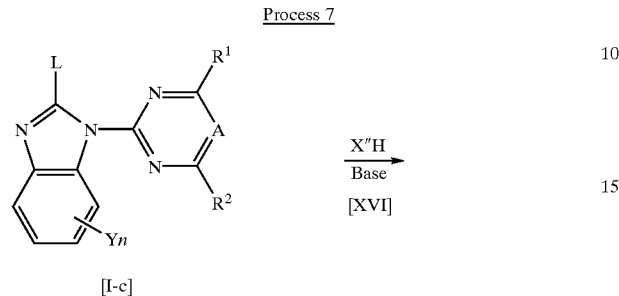

[I-c]

(wherein Y, $R^1$, $R^2$, A, L and n have the same meanings as mentioned above respectively, and X″ is a ($C_1$–$C_6$) alkoxy, ($C_2$–$C_6$) alkenyloxy, ($C_2$–$C_6$) alkynyloxy, ($C_1$–$C_6$) alkylthio or ($C_1$–$C_6$) alkylamino group.)

The compound of the present invention represented by the general formula [I-f] can be produced by reacting a pyrimidinylbenzimidazole derivative or triazinylbenzimidazole derivative represented by the general formula [I-c] and an alcohol, mercaptan or amine represented by the general formula [XVI] in the presence of a base without a solvent or in a solvent. As the base and the solvent which can be used in the present reaction, the base and the solvent as exemplified in Process 1 may be used. The reaction temperature may be selected within a range of from –20° C. to the boiling point of the reaction mixture to be used, preferably within a range of from room temperature to the boiling point of the reaction mixture. After the completion of the reaction, the desired product is isolated from the reaction system by a conventional method and may be purified by e.g. column chromatography or recrystallization, as the case requires.

Process 8

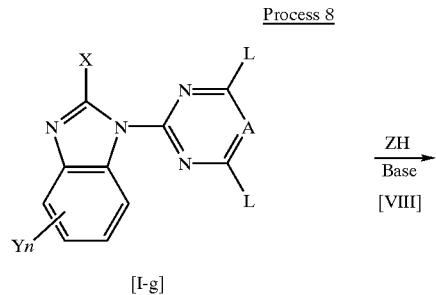

[I-g]

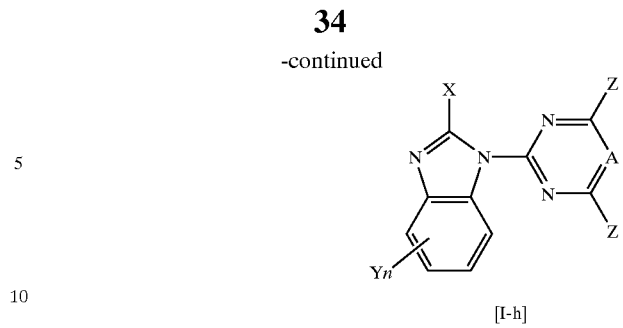

[I-h]

(wherein X, Y, A, L and n have the same meanings as mentioned above respectively, and Z is a ($C_1$–$C_6$) alkoxy, ($C_2$–$C_6$) alkenyloxy, ($C_2$–$C_6$) alkynloxy, ($C_1$–$C_6$) alkylthio or di ($C_1$–$C_6$) alkylamino group.)

The compound of the present invention represented by the general formula [I-h] can be produced by reacting a pyrimidinylbenzimidazole derivative or triazinylbenzimidazole derivative represented by the general formula [I-g] and an alcohol, mercaptan or amine represented by the general formula [VIII] in the presence of a base without a solvent or in a proper solvent. As the base and the solvent which can be used in the present reaction, the base and the solvent as exemplified in Process 1 may be used. The reaction temperature may be selected within a range of from –20° C. to the boiling point of the reaction mixture to be used, preferably within a range of from room temperature to the boiling point of the reaction mixture. After the completion of the reaction, the desired product is isolated from the reaction system by a conventional method and may be purified by e.g. column chromatography or recrystallization, as the case requires.

Process 9

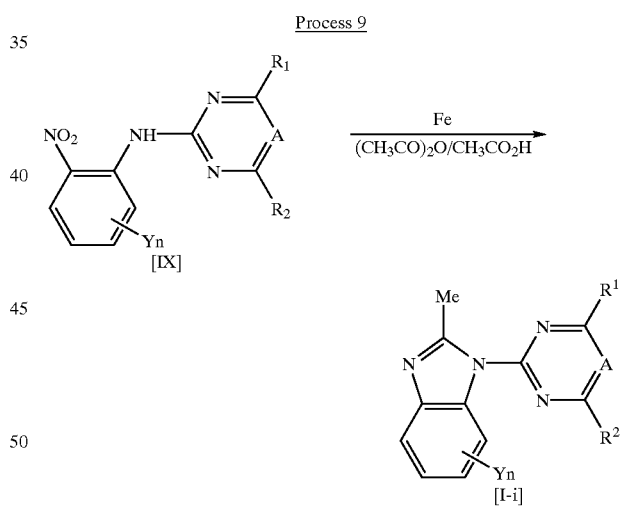

(wherein Y, $R^1$, $R^2$, A and n have the same meanings as mentioned above respectively.)

The compound of the present invention represented by the general formula [I-i] can be produced by reducing an anilinotriazine derivative represented by the general formula [IX] with iron powder in acetic acid or in a mixed solvent of acetic anhydride and acetic acid. The reaction temperature may be selected within a range of from –20° C. to the boiling point of the reaction mixture to be used, preferably within a range of from room temperature to the boiling point of the reaction mixture. After the completion of the reaction, the desired product is isolated from the reaction system by a conventional method and may be purified by e.g. column chromatography or recrystallization, as the case requires.

Now, processes for synthesizing the production intermediates for the compounds of the present invention will be explained in detail below.

Process 10

Synthesis of Production Intermediate Represented by the General Formula [IV]

The compound [IV] may be synthesized, for example, in accordance with the following process, but the process is not limited thereto.

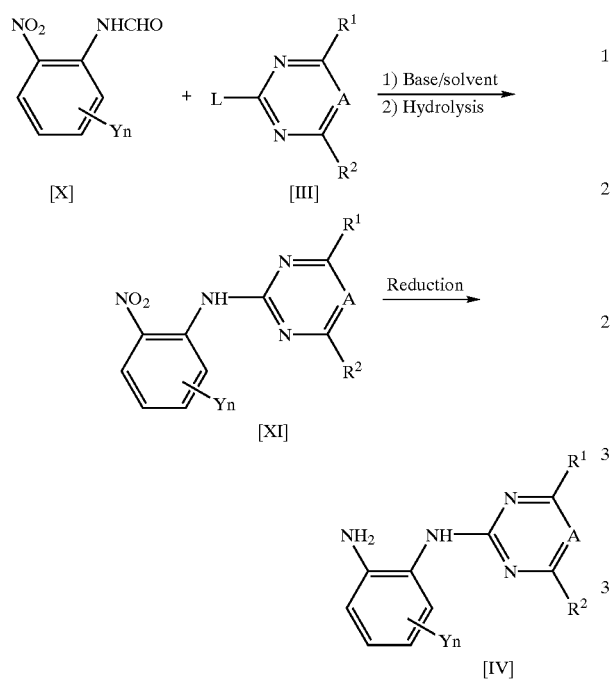

(wherein Y, $R^1$, $R^2$, A, L and n have the same meanings as mentioned above respectively.)

A formanilide derivative represented by the general formula [X] and a pyrimidine derivative or triazine derivative represented by the general formula [III] are reacted in the presence of a base in an inert solvent at a reaction temperature within a range of from $-20°$ C. to the boiling point of the solvent, preferably within a range of from room temperature to $80°$ C., followed by hydrolysis with e.g. an acid such as hydrochloric acid, hydrobromic acid or sulfuric acid or an alkali metal hydroxide such as sodium hydroxide or potassium hydroxide by a generally known method to obtain [XI]. Then, the obtained [XI] is reduced with a reducing agent such as iron, tin chloride, or a hydrogen atom accompanied with another catalyst such as palladium carbon or Raney Nickel, by a generally known method to produce an anilinopyrimidine derivative or anilinotriazine derivative represented by the general formula [IV].

Process 11

Synthesis of Production Intermediate Represented by the General Formula [XI-b]

The compound [XI-b] may be synthesized, for example, in accordance with the following process, but the process is not limited thereto.

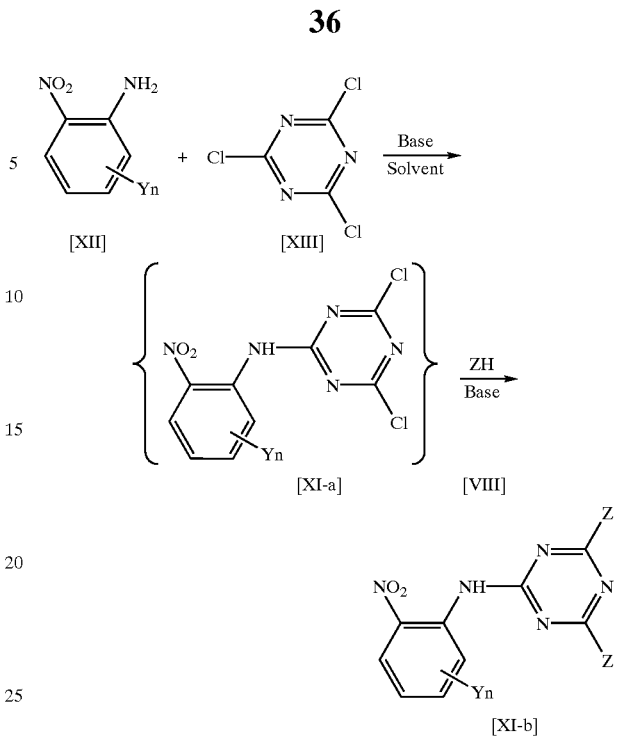

(wherein Y, Z and n have the same meanings as mentioned above respectively.)

A nitroaniline derivative represented by the general formula [XII] and cyanuric chloride represented by [XIII] are reacted in the presence of a base without a solvent or in a proper solvent to produce an anilinotriazine derivative represented by the general formula [XI-a], which is successively reacted with an alcohol, mercaptan or amine represented by the general formula [VIII] in the presence of a base without a solvent or in a proper solvent to produce an anilinotriazine derivative represented by the general formula [XI-b]. As the base and the solvent which can be used in the present reaction, the base and the solvent as exemplified in Process 1 may be used. The reaction temperature may be selected within a range of from $-20°$ C. to the boiling point of the reaction mixture to be used, preferably within a range of from room temperature to the boiling point of the reaction mixture. After the completion of the reaction, the desired product is isolated from the reaction system by a conventional method and may be purified by e.g. column chromatography or recrystallization, as the case requires.

Process 12

Synthesis of Production Intermediates Represented by the General Formulae [XI-c] and [XI-d]

The compounds [XI-c] and [XI-d] may be synthesized, for example, in accordance with the following process, but the process is not limited thereto.

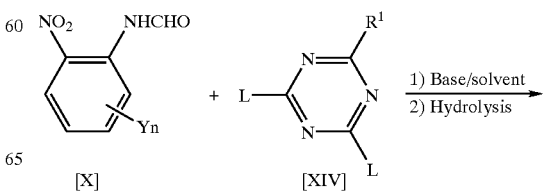

-continued

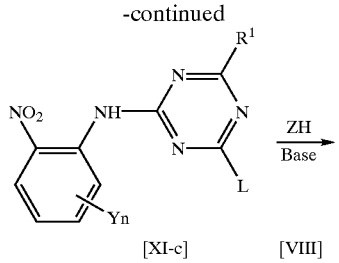

[XI-c] [VIII]

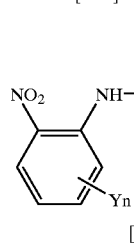

[XI-d]

(wherein R¹, Y, L, Z and n have the same meanings as mentioned above respectively.)

A formanilide derivative represented by the general formula [X] and a triazine derivative represented by [XIV] are reacted in the presence of a base without a solvent or in a proper solvent, followed by hydrolysis with e.g. an acid such as hydrochloric acid, hydrobromic acid or sulfuric acid or an alkali metal hydroxide such as sodium hydroxide or potassium hydroxide, by a generally known method to produce an anilinotriazine derivative represented by the general formula [XI-c], which is successively reacted with an alcohol, mercaptan or amine represented by the general formula [VIII] in the presence of a base without a solvent or in a proper solvent to produce an anilinotriazine derivative represented by the general formula [XI-d]. As the base and the solvent which can be used in the present reaction, the base and the solvent as exemplified in Process 1 may be used. The reaction temperature may be selected within a range of from −20° C. to the boiling point of the reaction mixture to be used, preferably within a range of from room temperature to the boiling point of the reaction mixture. After the completion of the reaction, the desired product is isolated from the reaction system by a conventional method and may be purified by e.g. column chromatography or recrystallization, as the case requires.

Here, the anilinopyrimidine and anilinotriazine derivatives represented by the general formulae [IV], [V] and [XI] are also novel compounds, and specific examples thereof will be disclosed in Tables 36 to 65.

TABLE 36

| Compound No. | X | Yn | A | R¹ | R² | m.p. (° C.) or RI ($n_D^{20}$) |
|---|---|---|---|---|---|---|
| 1-1 | H | H | CH | OMe | OMe | |
| 1-2 | Me | H | CH | OMe | OMe | |
| 1-3 | Et | H | CH | OMe | OMe | |

TABLE 36-continued

| Compound No. | X | Yn | A | R¹ | R² | m.p. (° C.) or RI ($n_D^{20}$) |
|---|---|---|---|---|---|---|
| 1-4 | Pr | H | CH | OMe | OMe | |
| 1-5 | Pr-i | H | CH | OMe | OMe | |
| 1-6 | Pr-c | H | CH | OMe | OMe | |
| 1-7 | Bu | H | CH | OMe | OMe | |
| 1-8 | Bn | H | CH | OMe | OMe | 169–172 |
| 1-9 | Bn(4-Cl) | H | CH | OMe | OMe | 187–200 |
| 1-10 | Bn(4-Me) | H | CH | OMe | OMe | 157–158 |
| 1-11 | Bn(4-OMe) | H | CH | OMe | OMe | |
| 1-12 | CH=CH₂ | H | CH | OMe | OMe | 147–149 |
| 1-13 | C≡CH | H | CH | OMe | OMe | |
| 1-14 | CH₂OEt | H | CH | OMe | OMe | |
| 1-15 | CH₂Cl | H | CH | OMe | OMe | 125–126 |
| 1-16 | CH₂CH₂Cl | H | CH | OMe | OMe | 162–165 |
| 1-17 | CH₂I | H | CH | OMe | OMe | |
| 1-18 | CCl₃ | H | CH | OMe | OMe | |
| 1-19 | CF₃ | H | CH | OMe | OMe | |
| 1-20 | C₂F₅ | H | CH | OMe | OMe | 82–85 |
| 1-21 | Ph | H | CH | OMe | OMe | 148–152 |
| 1-22 | Ph(4-Cl) | H | CH | OMe | OMe | |
| 1-23 | Ph(4-Me) | H | CH | OMe | OMe | |
| 1-24 | Ph(4-OMe) | H | CH | OMe | OMe | |
| 1-25 | H | H | N | OMe | OMe | |
| 1-26 | Me | H | N | OMe | OMe | |

TABLE 37

| Compound No. | X | Yn | A | R¹ | R² | m.p. (° C.) or RI ($n_D^{20}$) |
|---|---|---|---|---|---|---|
| 1-27 | Et | H | N | OMe | OMe | |
| 1-28 | Pr | H | N | OMe | OMe | |
| 1-29 | Pr-i | H | N | OMe | OMe | |
| 1-30 | Pr-c | H | N | OMe | OMe | |
| 1-31 | Bu | H | N | OMe | OMe | |
| 1-32 | Bn | H | N | OMe | OMe | |
| 1-33 | Bn(4-Cl) | H | N | OMe | OMe | |
| 1-34 | Bn(4-Me) | H | N | OMe | OMe | |
| 1-35 | Bn(4-OMe) | H | N | OMe | OMe | |
| 1-36 | CH=CH₂ | H | N | OMe | OMe | |
| 1-37 | C≡CH | H | N | OMe | OMe | |
| 1-38 | CH₂OEt | H | N | OMe | OMe | |
| 1-39 | CH₂Cl | H | N | OMe | OMe | |
| 1-40 | CH₂I | H | N | OMe | OMe | |
| 1-41 | CCl₃ | H | N | OMe | OMe | |
| 1-42 | CF₃ | H | N | OMe | OMe | |
| 1-43 | C₂F₅ | H | N | OMe | OMe | |
| 1-44 | Ph | H | N | OMe | OMe | |
| 1-45 | Ph(4-Cl) | H | N | OMe | OMe | |
| 1-46 | Ph(4-Me) | H | N | OMe | OMe | |
| 1-47 | Ph(OMe) | H | N | OMe | OMe | |
| 1-48 | H | 6-Me | CH | OMe | OMe | |
| 1-49 | H | 6-Cl | CH | OMe | OMe | |
| 1-50 | H | 5-F | CH | OMe | OMe | |
| 1-51 | H | 5-Cl | CH | OMe | OMe | |
| 1-52 | H | 5-Br | CH | OMe | OMe | |
| 1-53 | H | 5-Me | CH | OMe | OMe | |
| 1-54 | H | 5-Bu-t | CH | OMe | OMe | |
| 1-55 | H | 5-CF₃ | CH | OMe | OMe | |
| 1-56 | H | 5-OMe | CH | OMe | OMe | |

TABLE 37-continued

| Compound No. | X | Yn | A | R¹ | R² | m.p. (° C.) or RI ($n_D^{20}$) |
|---|---|---|---|---|---|---|
| 1-57 | H | 5-OEt | CH | OMe | OMe | |
| 1-58 | H | 5-OPr | CH | OMe | OMe | |
| 1-59 | H | 5-OCF₃ | CH | OMe | OMe | |

TABLE 38

| Compound No. | X | Yn | A | R¹ | R² | m.p. (° C.) or RI ($n_D^{20}$) |
|---|---|---|---|---|---|---|
| 1-60 | H | 5-OCH₂CH=CH₂ | CH | OMe | OMe | |
| 1-61 | H | 5-OCH₂C≡CH | CH | OMe | OMe | |
| 1-62 | H | 5-OPh | CH | OMe | OMe | |
| 1-63 | H | 5-OPh(4-Cl) | CH | OMe | OMe | |
| 1-64 | H | 5-OPh(4-Me) | CH | OMe | OMe | |
| 1-65 | H | 5-OPh(4-OMe) | CH | OMe | OMe | |
| 1-66 | H | 5-SMe | CH | OMe | OMe | |
| 1-67 | H | 5-CH₂OMe | CH | OMe | OMe | |
| 1-68 | H | 5-COMe | CH | OMe | OMe | |
| 1-69 | H | 5-COPh | CH | OMe | OMe | |
| 1-70 | H | 5-CO₂Et | CH | OMe | OMe | |
| 1-71 | H | 5-Ph | CH | OMe | OMe | |
| 1-72 | H | 5-Ph(4-Cl) | CH | OMe | OMe | |
| 1-73 | H | 5-Ph(4-Me) | CH | OMe | OMe | |
| 1-74 | H | 5-Ph(4-OMe) | CH | OMe | OMe | |
| 1-75 | H | 5-NO₂ | CH | OMe | OMe | |
| 1-76 | H | 5-NH₂ | CH | OMe | OMe | |
| 1-77 | H | 5-NHMe | CH | OMe | OMe | |
| 1-78 | H | 5-NMe₂ | CH | OMe | OMe | |
| 1-79 | H | 5-CN | CH | OMe | OMe | |
| 1-80 | H | 4-F | CH | OMe | OMe | |
| 1-81 | H | 4-Cl | CH | OMe | OMe | |
| 1-82 | H | 4-Me | CH | OMe | OMe | |
| 1-83 | H | 4-CF₃ | CH | OMe | OMe | |
| 1-84 | H | 4-OMe | CH | OMe | OMe | |
| 1-85 | H | 4-CO₂Et | CH | OMe | OMe | |
| 1-86 | H | 4-COPh | CH | OMe | OMe | |
| 1-87 | H | 3-Me | CH | OMe | OMe | |
| 1-88 | H | 3-Cl | CH | OMe | OMe | |
| 1-89 | H | 4,5-Cl₂ | CH | OMe | OMe | |
| 1-90 | H | 4,5-Me₂ | CH | OMe | OMe | |
| 1-91 | H | 4,5-(OMe)₂ | CH | OMe | OMe | |
| 1-92 | H | 4-CF₃, 6-Br | CH | OMe | OMe | |

TABLE 39

| Compound No. | X | Yn | A | R¹ | R² | m.p. (° C.) or RI ($n_D^{20}$) |
|---|---|---|---|---|---|---|
| 1-93 | H | 4-CF₃, 6-Cl | CH | OMe | OMe | |
| 1-94 | H | 4,5,6-F₃ | CH | OMe | OMe | |
| 1-95 | H | 6-Me | N | OMe | OMe | |
| 1-96 | H | 6-Cl | N | OMe | OMe | |
| 1-97 | H | 5-F | N | OMe | OMe | |
| 1-98 | H | 5-Cl | N | OMe | OMe | |
| 1-99 | H | 5-Br | N | OMe | OMe | |
| 1-100 | H | 5-Me | N | OMe | OMe | |
| 1-101 | H | 5-CF₃ | N | OMe | OMe | |
| 1-102 | H | 5-OMe | N | OMe | OMe | |
| 1-103 | H | 5-OEt | N | OMe | OMe | |
| 1-104 | H | 5-OPr | N | OMe | OMe | |
| 1-105 | H | 5-OCF₃ | N | OMe | OMe | |
| 1-106 | H | 5-OCH₂CH=CH₂ | N | OMe | OMe | |
| 1-107 | H | 5-OCH₂C≡CH | N | OMe | OMe | |
| 1-108 | H | 5-OPh | N | OMe | OMe | |
| 1-109 | H | 5-SMe | N | OMe | OMe | |

TABLE 39-continued

| Compound No. | X | Yn | A | R¹ | R² | m.p. (° C.) or RI ($n_D^{20}$) |
|---|---|---|---|---|---|---|
| 1-110 | H | 5-COPh | N | OMe | OMe | |
| 1-111 | H | 5-CO₂Et | N | OMe | OMe | |
| 1-112 | H | 5-Ph | N | OMe | OMe | |
| 1-113 | H | 5-Ph(4-Cl) | N | OMe | OMe | |
| 1-114 | H | 5-Ph(4-Me) | N | OMe | OMe | |
| 1-115 | H | 5-Ph(4-OMe) | N | OMe | OMe | |
| 1-116 | H | 5-NO₂ | N | OMe | OMe | |
| 1-117 | H | 5-NH₂ | N | OMe | OMe | |
| 1-118 | H | 5-NHMe | N | OMe | OMe | |
| 1-119 | H | 5-NMe₂ | N | OMe | OMe | |
| 1-120 | H | 5-CN | N | OMe | OMe | |
| 1-121 | H | 4-F | N | OMe | OMe | |
| 1-122 | H | 4-Cl | N | OMe | OMe | |
| 1-123 | H | 4-Me | N | OMe | OMe | |
| 1-124 | H | 4-CF₃ | N | OMe | OMe | |
| 1-125 | H | 4-OMe | N | OMe | OMe | |

TABLE 40

| Compound No. | X | Yn | A | R¹ | R² | m.p. (° C.) or RI ($n_D^{20}$) |
|---|---|---|---|---|---|---|
| 1-126 | H | 4-NO₂ | N | OMe | OMe | |
| 1-127 | H | 4-CO₂Et | N | OMe | OMe | |
| 1-128 | H | 4-COPh | N | OMe | OMe | |
| 1-129 | H | 3-Me | N | OMe | OMe | |
| 1-130 | H | 3-Cl | N | OMe | OMe | |
| 1-131 | H | 4,5-Cl₂ | N | OMe | OMe | |
| 1-132 | H | 4,5-Me₂ | N | OMe | OMe | |
| 1-133 | H | 4,5-(OMe)₂ | N | OMe | OMe | |
| 1-134 | H | 4-CF₃, 6-Br | N | OMe | OMe | |
| 1-135 | H | 4-CF₃, 6-Cl | N | OMe | OMe | |
| 1-136 | H | 4,5,6-F₃ | N | OMe | OMe | |
| 1-137 | Me | 6-Me | CH | OMe | OMe | |
| 1-138 | Me | 6-Cl | CH | OMe | OMe | |
| 1-139 | Me | 6-F | CH | OMe | OMe | |
| 1-140 | Me | 5-Cl | CH | OMe | OMe | |
| 1-141 | Me | 5-Br | CH | OMe | OMe | |
| 1-142 | Me | 5-Me | CH | OMe | OMe | |
| 1-143 | Me | 5-Bu-t | CH | OMe | OMe | |
| 1-144 | Me | 5-CF₃ | CH | OMe | OMe | |
| 1-145 | Me | 5-OMe | CH | OMe | OMe | |
| 1-146 | Me | 5-COPh | CH | OMe | OMe | |
| 1-147 | Me | 5-Ph | CH | OMe | OMe | |
| 1-148 | Me | 5-NH₂ | CH | OMe | OMe | |
| 1-149 | Me | 5-NMe₂ | CH | OMe | OMe | |
| 1-150 | Me | 5-CN | CH | OMe | OMe | |
| 1-151 | Me | 4-F | CH | OMe | OMe | |
| 1-152 | Me | 4-Cl | CH | OMe | OMe | |
| 1-153 | Me | 4-Me | CH | OMe | OMe | |
| 1-154 | Me | 4-CF₃ | CH | OMe | OMe | |
| 1-155 | Me | 4-OMe | CH | OMe | OMe | |
| 1-156 | Me | 4-COPh | CH | OMe | OMe | |
| 1-157 | Me | 4,5-Cl₂ | CH | OMe | OMe | |
| 1-158 | Me | 4,5-Me₂ | CH | OMe | OMe | |

TABLE 41

| Compound No. | X | Yn | A | R¹ | R² | m.p. (° C.) or RI ($n_D^{20}$) |
|---|---|---|---|---|---|---|
| 1-159 | Me | 4,5-(OMe)₂ | CH | OMe | OMe | |
| 1-160 | Me | 6-Me | N | OMe | OMe | |
| 1-161 | Me | 6-Cl | N | OMe | OMe | |
| 1-162 | Me | 5-F | N | OMe | OMe | |

TABLE 41-continued

| Compound No. | X | Yn | A | R¹ | R² | m.p. (° C.) or RI ($n_D^{20}$) |
|---|---|---|---|---|---|---|
| 1-163 | Me | 5-Cl | N | OMe | OMe | |
| 1-164 | Me | 5-Br | N | OMe | OMe | |
| 1-165 | Me | 5-Me | N | OMe | OMe | 180–183 |
| 1-166 | Me | 5-Et | N | OMe | OMe | |
| 1-167 | Me | 5-Pr | N | OMe | OMe | |
| 1-168 | Me | 5-Pr-i | N | OMe | OMe | |
| 1-169 | Me | 5-Bu-t | N | OMe | OMe | |
| 1-170 | Me | 5-CH=CH₂ | N | OMe | OMe | |
| 1-171 | Me | 5-C≡CBu | N | OMe | OMe | |
| 1-172 | Me | 5-CF₃ | N | OMe | OMe | |
| 1-173 | Me | 5-OMe | N | OMe | OMe | |
| 1-174 | Me | 5-SMe | N | OMe | OMe | |
| 1-175 | Me | 5-COPh | N | OMe | OMe | |
| 1-176 | Me | 5-Ph | N | OMe | OMe | |
| 1-177 | Me | 5-NH₂ | N | OMe | OMe | |
| 1-178 | Me | 5-NMe₂ | N | OMe | OMe | |
| 1-179 | Me | 5-CN | N | OMe | OMe | |
| 1-180 | Me | 4-F | N | OMe | OMe | |
| 1-181 | Me | 4-Cl | N | OMe | OMe | |
| 1-182 | Me | 4-Me | N | OMe | OMe | |
| 1-183 | Me | 4-CF₃ | N | OMe | OMe | |
| 1-184 | Me | 4-OMe | N | OMe | OMe | |
| 1-185 | Me | 4-OEt | N | OMe | OMe | |
| 1-186 | Me | 4-OPr | N | OMe | OMe | |
| 1-187 | Me | 4-CO₂Et | N | OMe | OMe | |
| 1-188 | Me | 4-COPh | N | OMe | OMe | |
| 1-189 | Me | 4,5-Cl₂ | N | OMe | OMe | |
| 1-190 | Me | 4,6-Me₂ | N | OMe | OMe | |
| 1-191 | Me | 4,5-Me₂ | N | OMe | OMe | |

TABLE 42

| Compound No. | X | Yn | A | R¹ | R² | m.p. (° C.) or RI ($n_D^{20}$) |
|---|---|---|---|---|---|---|
| 1-192 | Me | 4,5-(OMe)₂ | N | OMe | OMe | |
| 1-193 | CF₃ | 5-F | CH | OMe | OMe | 158–160 |
| 1-194 | CF₃ | 5-Cl | CH | OMe | OMe | 150–151 |
| 1-195 | CF₃ | 5-Br | CH | OMe | OMe | |
| 1-196 | CF₃ | 5-Me | CH | OMe | OMe | 144–147 |
| 1-197 | CF₃ | 5-CF₃ | CH | OMe | OMe | 168–171 |
| 1-198 | CF₃ | 5-OMe | CH | OMe | OMe | |
| 1-199 | CF₃ | 5-OEt | CH | OMe | OMe | 122–125 |
| 1-200 | CF₃ | 5-OPr | CH | OMe | OMe | |
| 1-201 | CF₃ | 5-NMe₂ | CH | OMe | OMe | |
| 1-202 | CF₃ | 5-CN | CH | OMe | OMe | |
| 1-203 | CF₃ | 4-F | CH | OMe | OMe | |
| 1-204 | CF₃ | 4-Cl | CH | OMe | OMe | |
| 1-205 | CF₃ | 4-Me | CH | OMe | OMe | |
| 1-206 | CF₃ | 4,5-(OMe)₂ | CH | OMe | OMe | |
| 1-207 | CF₃ | 5-F | N | OMe | OMe | 202–205 |
| 1-208 | CF₃ | 5-Cl | N | OMe | OMe | |
| 1-209 | CF₃ | 5-Br | N | OMe | OMe | |
| 1-210 | CF₃ | 5-Me | N | OMe | OMe | 195–198 |
| 1-211 | CF₃ | 5-Et | N | OMe | OMe | 182–185 |
| 1-212 | CF₃ | 5-Pr | N | OMe | OMe | 141–144 |
| 1-213 | CF₃ | 5-Pr-i | N | OMe | OMe | 193–196 |
| 1-214 | CF₃ | 5-Bu-t | N | OMe | OMe | 215–218 |
| 1-215 | CF₃ | 5-CF₃ | N | OMe | OMe | |
| 1-216 | CF₃ | 5-OMe | N | OMe | OMe | 183–185 |
| 1-217 | CF₃ | 5-OEt | N | OMe | OMe | |
| 1-218 | CF₃ | 5-OPr | N | OMe | OMe | |
| 1-219 | CF₃ | 5-OCF₃ | N | OMe | OMe | 188–191 |
| 1-220 | CF₃ | 5-SMe | N | OMe | OMe | |
| 1-221 | CF₃ | 5-NHMe | N | OMe | OMe | |
| 1-222 | CF₃ | 5-NMe₂ | N | OMe | OMe | |
| 1-223 | CF₃ | 5-CN | N | OMe | OMe | |
| 1-224 | CF₃ | 5-CO₂Me | N | OMe | OMe | 186–189 |

TABLE 43

| Compound No. | X | Yn | A | R¹ | R² | m.p. (° C.) or RI ($n_D^{20}$) |
|---|---|---|---|---|---|---|
| 1-225 | CF₃ | 5-I | N | OMe | OMe | 169–172 |
| 1-226 | CF₃ | 4-F | N | OMe | OMe | |
| 1-227 | CF₃ | 4-Cl | N | OMe | OMe | |
| 1-228 | CF₃ | 6-Me | N | OMe | OMe | |
| 1-229 | CF₃ | 4,5-(OMe)₂ | N | OMe | OMe | |
| 1-230 | Et | 5-F | CH | OMe | OMe | |
| 1-231 | Et | 5-Cl | CH | OMe | OMe | |
| 1-232 | Et | 5-Me | CH | OMe | OMe | |
| 1-233 | Et | 5-CF₃ | CH | OMe | OMe | |
| 1-234 | Et | 5-OMe | CH | OMe | OMe | |
| 1-235 | Et | 5-CN | CH | OMe | OMe | |
| 1-236 | Et | 4-F | CH | OMe | OMe | |
| 1-237 | Et | 4-Cl | CH | OMe | OMe | |
| 1-238 | Et | 4-Me | CH | OMe | OMe | |
| 1-239 | Et | 4,5-(OMe)₂ | CH | OMe | OMe | |
| 1-240 | Et | 5-F | N | OMe | OMe | |
| 1-241 | Et | 5-Cl | N | OMe | OMe | |
| 1-242 | Et | 5-Me | N | OMe | OMe | |
| 1-243 | Et | 5-CF₃ | N | OMe | OMe | |
| 1-244 | Et | 5-OMe | N | OMe | OMe | |
| 1-245 | Et | 5-CN | N | OMe | OMe | |
| 1-246 | Et | 4-F | N | OMe | OMe | |
| 1-247 | Et | 4-Cl | N | OMe | OMe | |
| 1-248 | Et | 4-Me | N | OMe | OMe | |
| 1-249 | Et | 4,5-(OMe)₂ | N | OMe | OMe | |
| 1-250 | Pr | 5-Cl | N | OMe | OMe | 137–140 |
| 1-251 | Pr-i | 5-Cl | N | OMe | OMe | 149–152 |
| 1-252 | Pr-c | 5-Cl | N | OMe | OMe | 181–184 |
| 1-253 | CH₂OMe | 5-Cl | N | OMe | OMe | |
| 1-254 | Ph | 5-Cl | N | OMe | OMe | 176–179 |
| 1-255 | Ph | 5-Br | N | OMe | OMe | |
| 1-256 | Ph(4-Cl) | 5-Cl | N | OMe | OMe | |
| 1-257 | Ph(4-Me) | 5-Cl | N | OMe | OMe | |

TABLE 44

| Compound No. | X | Yn | A | R¹ | R² | m.p. (° C.) or RI ($n_D^{20}$) |
|---|---|---|---|---|---|---|
| 1-258 | Ph(4-OMe) | 5-Cl | N | OMe | OMe | |
| 1-259 | Bn | 5-Cl | N | OMe | OMe | |
| 1-260 | CF₂Cl | 5-Me | N | OMe | OMe | |
| 1-261 | CF₂Cl | 5-Cl | N | OMe | OMe | |
| 1-262 | CF₂Cl | 5-Br | N | OMe | OMe | |
| 1-263 | CF₂Cl | 5-OMe | N | OMe | OMe | |
| 1-264 | CH₂Cl | 5-Me | N | OMe | OMe | |
| 1-265 | CH₂Cl | 5-Cl | N | OMe | OMe | |
| 1-266 | CH₂Cl | 5-Br | N | OMe | OMe | |
| 1-267 | CH₂Cl | 5-OMe | N | OMe | OMe | |
| 1-268 | C₂F₅ | 5-Me | N | OMe | OMe | |
| 1-269 | C₂F₅ | 5-Cl | N | OMe | OMe | |
| 1-270 | C₂F₅ | 5-Br | N | OMe | OMe | |
| 1-271 | C₂F₅ | 5-OMe | N | OMe | OMe | |
| 1-272 | Ph(4-Cl) | 5-OMe | CH | OMe | OMe | 187–200 |
| 1-273 | CH₂OMe | 5-Cl | N | OMe | OMe | 183–186 |
| 1-274 | CF₃ | 5-Me | N | OMe | OEt | |
| 1-275 | CF₃ | 5-Cl | N | OMe | OEt | |
| 1-276 | CF₃ | 5-Br | N | OMe | OEt | |
| 1-277 | CF₂Cl | 5-Cl | N | OMe | OEt | |
| 1-278 | CF₂Cl | 5-Br | N | OMe | OEt | |
| 1-279 | CF₂Cl | 5-Me | N | OMe | OEt | |
| 1-280 | CH₂Cl | 5-Cl | N | OMe | OEt | |
| 1-281 | CH₂Cl | 5-Br | N | OMe | OEt | |
| 1-282 | CH₂Cl | 5-Me | N | OMe | OEt | |
| 1-283 | C₂F₅ | 5-Cl | N | OMe | OEt | |
| 1-284 | C₂F₅ | 5-Br | N | OMe | OEt | |
| 1-285 | C₂F₅ | 5-Me | N | OMe | OEt | |
| 1-286 | Me | 5-F | CH | OEt | OEt | |
| 1-287 | Me | 5-Cl | CH | OEt | OEt | |

TABLE 44-continued

| Compound No. | X | Yn | A | R¹ | R² | m.p. (° C.) or RI ($n_D^{20}$) |
|---|---|---|---|---|---|---|
| 1-288 | Me | 5-Br | CH | OEt | OEt | |
| 1-289 | Me | 5-Me | CH | OEt | OEt | |
| 1-290 | Me | 5-CF₃ | CH | OEt | OEt | |

TABLE 45

| Compound No. | X | Yn | A | R¹ | R² | m.p. (° C.) or RI ($n_D^{20}$) |
|---|---|---|---|---|---|---|
| 1-291 | Me | 5-F | N | OEt | OEt | |
| 1-292 | Me | 5-Cl | N | OEt | OEt | |
| 1-293 | Me | 5-Br | N | OEt | OEt | |
| 1-294 | Me | 5-Me | N | OEt | OEt | |
| 1-295 | Me | 5-CF₃ | N | OEt | OEt | |
| 1-296 | CF₃ | 5-F | CH | OEt | OEt | |
| 1-297 | CF₃ | 5-Cl | CH | OEt | OEt | |
| 1-298 | CF₃ | 5-Br | CH | OEt | OEt | |
| 1-299 | CF₃ | 5-Me | CH | OEt | OEt | |
| 1-300 | CF₃ | 5-CF₃ | CH | OEt | OEt | |
| 1-301 | CF₃ | 5-OMe | N | OEt | OEt | 159–161 |

TABLE 45-continued

| Compound No. | X | Yn | A | R¹ | R² | m.p. (° C.) or RI ($n_D^{20}$) |
|---|---|---|---|---|---|---|
| 1-302 | CF₃ | 5-Cl | N | OEt | OEt | 194–197 |
| 1-303 | CF₃ | 5-Br | N | OEt | OEt | 191–194 |
| 1-304 | CF₃ | 5-Me | N | OEt | OEt | 201–204 |
| 1-305 | CF₃ | 5-CF₃ | N | OEt | OEt | |
| 1-306 | Ph | H | N | OEt | OEt | |
| 1-307 | Ph(4-Cl) | H | N | OEt | OEt | |
| 1-308 | Ph(4-Me) | H | N | OEt | OEt | |
| 1-309 | Ph(4-OMe) | H | N | OEt | OEt | |
| 1-310 | Ph | 5-Cl | N | OEt | OEt | |
| 1-311 | Ph(4-Cl) | 5-Cl | N | OEt | OEt | |
| 1-312 | Ph(4-Me) | 5-Cl | N | OEt | OEt | |
| 1-313 | Ph(4-OMe) | 5-Cl | N | OEt | OEt | |
| 1-314 | Ph | 5-Br | N | OEt | OEt | |
| 1-315 | Ph(4-Cl) | 5-Br | N | OEt | OEt | |
| 1-316 | Ph(4-Me) | 5-Br | N | OEt | OEt | |
| 1-317 | Ph(4-OMe) | 5-Br | N | OEt | OEt | |
| 1-318 | H | H | CH | OPr | OPr | |
| 1-319 | Me | 5-Cl | N | OPr | OPr | |
| 1-320 | Me | 5-Br | N | OPr | OPr | |
| 1-321 | Me | 5-Me | N | OPr | OPr | |
| 1-322 | CF₃ | 5-Cl | N | OPr | OPr | 150–153 |
| 1-323 | CF₃ | 5-Br | N | OPr | OPr | |

TABLE 46

| Compound No. | X | Yn | A | R¹ | R² | m.p. (° C.) or RI ($n_D^{20}$) |
|---|---|---|---|---|---|---|
| 1-324 | CF₃ | 5-Me | N | OPr | OPr | |
| 1-325 | H | H | CH | OPr-i | OPr-i | |
| 1-326 | Me | 5-Cl | CH | OPr-i | OPr-i | |
| 1-327 | Me | 5-Me | CH | OPr-i | OPr-i | |
| 1-328 | Me | 5-Cl | N | OPr-i | OPr-i | |
| 1-329 | Me | 5-Br | N | OPr-i | OPr-i | |
| 1-330 | Me | 5-Me | N | OPr-i | OPr-i | |
| 1-331 | CF₃ | 5-Cl | N | OPr-i | OPr-i | 198–201 |
| 1-332 | CF₃ | 5-Br | N | OPr-i | OPr-i | |
| 1-333 | CF₃ | 5-Me | N | OPr-i | OPr-i | |
| 1-334 | Me | 5-Cl | N | OCH₂CH=CH₂ | OCH₂CH=CH₂ | |
| 1-335 | Me | 5-Br | N | OCH₂CH=CH₂ | OCH₂CH=CH₂ | |
| 1-336 | Me | 5-Me | N | OCH₂CH=CH₂ | OCH₂CH=CH₂ | |
| 1-337 | CF₃ | 5-Cl | N | OCH₂CH=CH₂ | OCH₂CH=CH₂ | 121–124 |
| 1-338 | CF₃ | 5-Br | N | OCH₂CH=CH₂ | OCH₂CH=CH₂ | |
| 1-339 | CF₃ | 5-Me | N | OCH₂CH=CH₂ | OCH₂CH=CH₂ | |
| 1-340 | Me | 5-Cl | N | OCH₂C≡CH | OCH₂C≡CH | |
| 1-341 | Me | 5-Br | N | OCH₂C≡CH | OCH₂C≡CH | |
| 1-342 | Me | 5-Me | N | OCH₂C≡CH | OCH₂C≡CH | |
| 1-343 | CF₃ | 5-Cl | N | OCH₂C≡CH | OCH₂C≡CH | |
| 1-344 | CF₃ | 5-Br | N | OCH₂C≡CH | OCH₂C≡CH | |
| 1-345 | CF₃ | 5-Me | N | OCH₂C≡CH | OCH₂C≡CH | |
| 1-346 | Me | 5-Cl | CH | OCH₂CN | OCH₂CN | |
| 1-347 | Me | 5-Me | CH | OCH₂CN | OCH₂CN | |
| 1-348 | Me | 5-Cl | N | OCH₂CN | OCH₂CN | |
| 1-349 | Me | 5-Br | N | OCH₂CN | OCH₂CN | |
| 1-350 | Me | 5-Me | N | OCH₂CN | OCH₂CN | |
| 1-351 | CF₃ | 5-Cl | N | OCH₂CN | OCH₂CN | |
| 1-352 | CF₃ | 5-Br | N | OCH₂CN | OCH₂CN | |
| 1-353 | CF₃ | 5-Me | N | OCH₂CN | OCH₂CN | |
| 1-354 | Me | 5-Cl | CH | OCH₂CH₂OMe | OCH₂CH₂OMe | |
| 1-355 | Me | 5-Me | CH | OCH₂CH₂OMe | OCH₂CH₂OMe | |
| 1-356 | H | 5-Br | N | OCH₂CH₂OMe | OCH₂CH₂OMe | |

TABLE 47

| Compound No. | X | Yn | A | R¹ | R² | m.p. (° C.) or RI ($n_D^{20}$) |
|---|---|---|---|---|---|---|
| 1-357 | Me | 5-Cl | N | OCH₂CH₂OMe | OCH₂CH₂OMe | |
| 1-358 | Me | 5-Br | N | OCH₂CH₂OMe | OCH₂CH₂OMe | |
| 1-359 | Me | 5-Me | N | OCH₂CH₂OMe | OCH₂CH₂OMe | |
| 1-360 | CF₃ | 5-Cl | N | OCH₂CH₂OMe | OCH₂CH₂OMe | |
| 1-361 | CF₃ | 5-Br | N | OCH₂CH₂OMe | OCH₂CH₂OMe | |
| 1-362 | CF₃ | 5-Me | N | OCH₂CH₂OMe | OCH₂CH₂OMe | |
| 1-363 | H | 5-Br | N | OCH₂Pr-c | OCH₂Pr-c | |
| 1-364 | Me | 5-Cl | N | OCH₂Pr-c | OCH₂Pr-c | |
| 1-365 | Me | 5-Br | N | OCH₂Pr-c | OCH₂Pr-c | |
| 1-366 | Me | 5-Me | N | OCH₂Pr-c | OCH₂Pr-c | |
| 1-367 | CF₃ | 5-Cl | N | OCH₂Pr-c | OCH₂Pr-c | |
| 1-368 | CF₃ | 5-Br | N | OCH₂Pr-c | OCH₂Pr-c | |
| 1-369 | CF₃ | 5-Me | N | OCH₂Pr-c | OCH₂Pr-c | |
| 1-370 | H | H | CH | OBn | OBn | |
| 1-371 | H | H | N | OBn | OBn | |
| 1-372 | H | H | N | OBn(4-Cl) | OBn(4-Cl) | |
| 1-373 | H | H | N | OBn(4-Me) | OBn(4-Me) | |
| 1-374 | H | H | N | OBn(4-OMe) | OBn(4-OMe) | |
| 1-375 | H | H | CH | OMe | OPh | |
| 1-376 | H | H | N | OMe | OPh | |
| 1-377 | H | H | N | OMe | OPh(4-Cl) | |
| 1-378 | H | H | N | OMe | OPh(4-Me) | |
| 1-379 | H | H | N | OMe | OPh(4-OMe) | |
| 1-380 | H | H | CH | OMe | OCHF₂ | |
| 1-381 | H | H | N | OMe | OCHF₂ | |
| 1-382 | Me | 5-Cl | CH | OMe | H | |
| 1-383 | Me | 5-Me | CH | OMe | H | |
| 1-384 | Me | 5-CF₃ | CH | OMe | H | |
| 1-385 | Me | 5-OMe | CH | OMe | H | |
| 1-386 | CF₃ | 5-Cl | CH | OMe | H | 125–128 |
| 1-387 | CF₃ | 5-Me | CH | OMe | H | 130–133 |
| 1-388 | CF₃ | 5-CF₃ | CH | OMe | H | |
| 1-389 | CF₃ | 5-OMe | CH | OMe | H | 153–156 |

TABLE 48

| Compound No. | X | Yn | A | R¹ | R² | m.p. (° C.) or RI ($n_D^{20}$) |
|---|---|---|---|---|---|---|
| 1-390 | CF₃ | 5-Cl | CH | OEt | H | |
| 1-391 | CF₃ | 5-Me | CH | OEt | H | 125–127 |
| 1-392 | CF₃ | 5-OMe | CH | OEt | H | |
| 1-393 | Me | 5-Cl | CH | OMe | Me | |
| 1-394 | Me | 5-Me | CH | OMe | Me | |
| 1-395 | Me | 5-CF₃ | CH | OMe | Me | |
| 1-396 | CF₃ | 5-Cl | CH | OMe | Me | |
| 1-397 | CF₃ | 5-Me | CH | OMe | Me | |
| 1-398 | CF₃ | 5-OMe | CH | OMe | Me | |
| 1-399 | Me | 5-Cl | N | OMe | Me | |
| 1-400 | Me | 5-Me | N | OMe | Me | |
| 1-401 | Me | 5-CF₃ | N | OMe | Me | |
| 1-402 | CF₃ | 5-Cl | N | OMe | Me | |
| 1-403 | CF₃ | 5-Me | N | OMe | Me | 192–195 |
| 1-404 | CF₃ | 5-OMe | N | OMe | Me | |
| 1-405 | CF₃ | 5-Cl | N | OMe | Pr | |
| 1-406 | CF₃ | 5-Br | N | OMe | Pr | |
| 1-407 | CF₃ | 5-Me | N | OMe | Pr | 149–152 |
| 1-408 | CF₃ | 5-Cl | N | OMe | Pr-c | |
| 1-409 | CF₃ | 5-Br | N | OMe | Pr-c | |
| 1-410 | CF₃ | 5-Me | N | OMe | Pr-c | 103–106 |
| 1-411 | CF₃ | 5-Cl | N | OEt | Pr-c | |
| 1-412 | CF₃ | 5-Me | N | OEt | Pr-c | |
| 1-413 | CF₃ | 5-CF₃ | N | OEt | Pr-c | |
| 1-414 | Me | 5-Cl | CH | OEt | Me | |
| 1-415 | Me | 5-Me | CH | OEt | Me | |
| 1-416 | Me | 5-CF₃ | CH | OEt | Me | |
| 1-417 | Me | 5-OMe | CH | OEt | Me | |
| 1-418 | CF₃ | 5-Cl | CH | OEt | Me | |
| 1-419 | CF₃ | 5-Me | CH | OEt | Me | |
| 1-420 | CF₃ | 5-OMe | CH | OEt | Me | 136–139 |
| 1-421 | Me | 5-Cl | N | OEt | Me | |
| 1-422 | Me | 5-Br | N | OEt | Me | |

TABLE 49

| Compound No. | X | Yn | A | R¹ | R² | m.p. (° C.) or RI ($n_D^{20}$) |
|---|---|---|---|---|---|---|
| 1-423 | Me | 5-Me | N | OEt | Me | |
| 1-424 | Me | 5-CF₃ | N | OEt | Me | |
| 1-425 | CF₃ | 5-Cl | N | OEt | Me | |
| 1-426 | CF₃ | 5-Br | N | OEt | Me | |
| 1-427 | CF₃ | 5-Me | N | OEt | Me | |
| 1-428 | CF₃ | 5-Cl | CH | OCH₂CH=CH₂ | Me | |
| 1-429 | CF₃ | 5-Me | CH | OCH₂CH=CH₂ | Me | |
| 1-430 | CF₃ | 5-OMe | CH | OCH₂CH=CH₂ | Me | |
| 1-431 | CF₃ | 5-Cl | N | OCH₂CH=CH₂ | Me | |
| 1-432 | CF₃ | 5-Me | N | OCH₂CH=CH₂ | Me | 175–178 |
| 1-433 | CF₃ | 5-OMe | N | OCH₂CH=CH₂ | Me | |
| 1-434 | CF₃ | 5-Me | CH | SMe | Me | |
| 1-435 | CF₃ | 5-Cl | CH | SMe | Me | |
| 1-436 | CF₃ | 5-Me | N | SMe | Me | 196–199 |
| 1-437 | CF₃ | 5-Cl | N | SMe | Me | 157–160 |
| 1-438 | CF₃ | 5-Cl | N | OMe | Et | |
| 1-439 | CF₃ | 5-Br | N | OMe | Et | |
| 1-440 | CF₃ | 5-Me | N | OMe | Et | |
| 1-441 | CF₃ | 5-Cl | N | OEt | Et | |
| 1-442 | CF₃ | 5-Br | N | OEt | Et | |

TABLE 49-continued

| Compound No. | X | Yn | A | R¹ | R² | m.p. (° C.) or RI ($n_D^{20}$) |
|---|---|---|---|---|---|---|
| 1-443 | CF₃ | 5-Me | N | OEt | Et | |
| 1-444 | Me | 5-Cl | N | SMe | SMe | |
| 1-445 | Me | 5-Br | N | SMe | SMe | |
| 1-446 | Me | 5-Me | N | SMe | SMe | |
| 1-447 | CF₃ | 5-Cl | N | SMe | SMe | |
| 1-448 | CF₃ | 5-Br | N | SMe | SMe | |
| 1-449 | CF₃ | 5-Me | N | SMe | SMe | |
| 1-450 | Me | 5-Cl | N | OMe | SMe | |
| 1-451 | Me | 5-Br | N | OMe | SMe | |
| 1-452 | CF₃ | 5-Cl | N | OMe | SMe | |
| 1-453 | CF₃ | 5-Br | N | OMe | SMe | |
| 1-454 | CF₃ | 5-Me | N | OMe | SMe | |
| 1-455 | Me | 5-Me | N | OMe | Ph | |

TABLE 50

| Compound No. | X | Yn | A | R¹ | R² | m.p. (° C.) or RI ($n_D^{20}$) |
|---|---|---|---|---|---|---|
| 1-456 | CF₃ | 5-Me | N | OMe | Ph | 219–222 |
| 1-457 | Me | H | CH | Cl | Cl | |
| 1-458 | Me | 4,5-Cl₂ | CH | Cl | Cl | |
| 1-459 | Me | H | N | Cl | Cl | |
| 1-460 | Me | H | CH | Cl | Me | |
| 1-461 | Me | 5-Cl | N | NMe₂ | NMe₂ | |
| 1-462 | CF₃ | 5-Cl | N | NMe₂ | NMe₂ | 219–222 |
| 1-463 | H | H | CH | OMe | NMe₂ | |
| 1-464 | H | H | CBr | OMe | OMe | |
| 1-465 | H | H | CMe | Cl | Cl | |
| 1-466 | Me | 5-Me | COMe | H | H | |
| 1-467 | Me | 5-Cl | COMe | H | H | |
| 1-468 | Me | 5-Cl | CH | Me | Me | |
| 1-469 | Me | 5-CF₃ | CH | Me | Me | |
| 1-470 | Me | 5-Cl | CH | Me | CF₃ | |
| 1-471 | Me | 5-Me | CH | Me | Et | |
| 1-472 | Me | 5-Cl | CH | Me | Et | |
| 1-473 | CF₃ | 5-Me | CH | Me | Et | |
| 1-474 | CF₃ | 5-Cl | CH | Me | Et | |
| 1-475 | Me | 5-Me | CH | Me | Pr-c | |
| 1-476 | Me | 5-Cl | CH | Me | Pr-c | |
| 1-477 | CF₃ | 5-Me | CH | Me | Pr-c | |
| 1-478 | CF₃ | 5-Cl | CH | Me | Pr-c | |
| 1-479 | CF₃ | 5-Cl | CH | C≡CMe | Me | |
| 1-480 | CF₃ | 5-Cl | N | C≡CMe | Me | |
| 1-481 | CF₃ | 5-Cl | CH | CH=CH₂ | Me | |
| 1-482 | CF₃ | 5-Cl | N | CH=CH₂ | Me | |
| 1-483 | Me | 5-Cl | CH | CHO | Me | |
| 1-484 | Me | 5-Cl | N | CHO | Me | |
| 1-485 | Me | 5-Cl | CH | COMe | Me | |
| 1-486 | Me | 5-Cl | N | COMe | Me | |
| 1-487 | Me | 5-Cl | CH | CH₂OMe | Me | |
| 1-488 | Me | 5-Me | CH | CH₂OMe | Me | |

TABLE 51

| Compound No. | X | Yn | A | R¹ | R² | m.p. (° C.) or RI ($n_D^{20}$) |
|---|---|---|---|---|---|---|
| 1-489 | Me | H | CH | CN | CN | |
| 1-490 | Me | H | CH | CN | Me | |
| 1-491 | Me | H | N | CN | CN | |
| 1-492 | Me | H | N | CN | Me | |
| 1-493 | Me | H | CH | SO₂Me | SO₂Me | |
| 1-494 | Me | H | N | SO₂Me | SO₂Me | |
| 1-495 | Me | H | CH | SO₂Me | Me | |

TABLE 52

| Compound No. | Yn | A | R¹ | R² | m.p. (° C.) or RI ($n_D^{20}$) |
|---|---|---|---|---|---|
| 2-1 | 3-Me | CH | OMe | OMe | |
| 2-2 | 3-Cl | CH | OMe | OMe | |
| 2-3 | 4-F | CH | OMe | OMe | 194–196 |
| 2-4 | 4-Cl | CH | OMe | OMe | 188–190 |
| 2-5 | 4-Br | CH | OMe | OMe | 191–194 |
| 2-6 | 4-Me | CH | OMe | OMe | 158–161 |
| 2-7 | 4-Bu-t | CH | OMe | OMe | |
| 2-8 | 4-CF₃ | CH | OMe | OMe | 178–180 |
| 2-9 | 4-OMe | CH | OMe | OMe | 189–190 |
| 2-10 | 4-OEt | CH | OMe | OMe | 178–180 |
| 2-11 | 4-OPr | CH | OMe | OMe | |
| 2-12 | 4-OCF₃ | CH | OMe | OMe | 144–147 |
| 2-13 | 4-OCH₂CH=CH₂ | CH | OMe | OMe | |
| 2-14 | 4-OCH₂C≡CH | CH | OMe | OMe | |
| 2-15 | 4-OPh | CH | OMe | OMe | |
| 2-16 | 4-OPh(4-Cl) | CH | OMe | OMe | |
| 2-17 | 4-OPh(4-Me) | CH | OMe | OMe | |
| 2-18 | 4-OPh(4-OMe) | CH | OMe | OMe | |
| 2-19 | 4-SMe | CH | OMe | OMe | |
| 2-20 | 4-CH₂OMe | CH | OMe | OMe | |
| 2-21 | 4-COMe | CH | OMe | OMe | |
| 2-22 | 4-COPh | CH | OMe | OMe | |
| 2-23 | 4-CO₂Et | CH | OMe | OMe | |
| 2-24 | 4-Ph | CH | OMe | OMe | |

TABLE 53

| Compound No. | Yn | A | R¹ | R² | m.p. (° C.) or RI ($n_D^{20}$) |
|---|---|---|---|---|---|
| 2-25 | 4-Ph(4-Cl) | CH | OMe | OMe | |
| 2-26 | 4-Ph(4-Me) | CH | OMe | OMe | |
| 2-27 | 4-Ph(4-OMe) | CH | OMe | OMe | |
| 2-28 | 4-NO₂ | CH | OMe | OMe | |
| 2-29 | 4-NH₂ | CH | OMe | OMe | |
| 2-30 | 4-NHMe | CH | OMe | OMe | |
| 2-31 | 4-NMe₂ | CH | OMe | OMe | |
| 2-32 | 4-CN | CH | OMe | OMe | 241–244 |
| 2-33 | 5-F | CH | OMe | OMe | |
| 2-34 | 5-Cl | CH | OMe | OMe | |
| 2-35 | 5-Me | CH | OMe | OMe | |
| 2-36 | 5-CF₃ | CH | OMe | OMe | |
| 2-37 | 5-OMe | CH | OMe | OMe | |
| 2-38 | 5-CO₂Me | CH | OMe | OMe | |
| 2-39 | 5-COPh | CH | OMe | OMe | |
| 2-40 | 6-Me | CH | OMe | OMe | 136–139 |
| 2-41 | 6-Cl | CH | OMe | OMe | |
| 2-42 | 4,5-Cl₂ | CH | OMe | OMe | |
| 2-43 | 4,5-Me₂ | CH | OMe | OMe | |
| 2-44 | 4,5-(OMe)₂ | CH | OMe | OMe | |
| 2-45 | 4,6-Me₂ | CH | OMe | OMe | 139–142 |
| 2-46 | 3-Br, 5-CF₃ | CH | OMe | OMe | |
| 2-47 | 3-Cl, 5-CF₃ | CH | OMe | OMe | |
| 2-48 | 3,4,5-F₃ | CH | OMe | OMe | |
| 2-49 | H | N | OMe | OMe | 177–180 |
| 2-50 | 3-Me | N | OMe | OMe | |
| 2-51 | 3-Cl | N | OMe | OMe | |
| 2-52 | 4-F | N | OMe | OMe | 184–187 |
| 2-53 | 4-Cl | N | OMe | OMe | 206–208 |

TABLE 53-continued

| Compound No. | Yn | A | R¹ | R² | m.p. (° C.) or RI ($n_D^{20}$) |
|---|---|---|---|---|---|
| 2-54 | 4-Br | N | OMe | OMe | |
| 2-55 | 4-I | N | OMe | OMe | 218–221 |

TABLE 54

| Compound No. | Yn | A | R¹ | R² | m.p. (° C.) or RI ($n_D^{20}$) |
|---|---|---|---|---|---|
| 2-56 | 4-Me | N | OMe | OMe | 189–191 |
| 2-57 | 4-Et | N | OMe | OMe | 146–149 |
| 2-58 | 4-Pr | N | OMe | OMe | 170–173 |
| 2-59 | 4-CF₃ | N | OMe | OMe | |
| 2-60 | 4-Bu-t | N | OMe | OMe | 118–121 |
| 2-61 | 4-C≡CBu-t | N | OMe | OMe | 117–120 |
| 2-62 | 4-OMe | N | OMe | OMe | 197–199 |
| 2-63 | 4-OEt | N | OMe | OMe | |
| 2-64 | 4-OPr | N | OMe | OMe | |
| 2-65 | 4-OCF₃ | N | OMe | OMe | 119–122 |
| 2-66 | 4-OCH₂CH=CH₂ | N | OMe | OMe | |
| 2-67 | 4-OCH₂C≡CH | N | OMe | OMe | |
| 2-68 | 4-OPh | N | OMe | OMe | |
| 2-69 | 4-SMe | N | OMe | OMe | |
| 2-70 | 4-COPh | N | OMe | OMe | 221–224 |
| 2-71 | 4-CO₂Me | N | OMe | OMe | 289–292 |
| 2-72 | 4-Ph | N | OMe | OMe | |
| 2-73 | 4-Ph(4-Cl) | N | OMe | OMe | |
| 2-74 | 4-Ph(4-Me) | N | OMe | OMe | |
| 2-75 | 4-Ph(4-OMe) | N | OMe | OMe | |
| 2-76 | 4-NO₂ | N | OMe | OMe | |
| 2-77 | 4-NH₂ | N | OMe | OMe | |
| 2-78 | 4-NHMe | N | OMe | OMe | |
| 2-79 | 4-NMe₂ | N | OMe | OMe | 155–158 |
| 2-80 | 4-CN | N | OMe | OMe | 189–201 |
| 2-81 | 5-F | N | OMe | OMe | |
| 2-82 | 5-Cl | N | OMe | OMe | |
| 2-83 | 5-Me | N | OMe | OMe | 151–154 |
| 2-84 | 5-CF₃ | N | OMe | OMe | |
| 2-85 | 5-OMe | N | OMe | OMe | |
| 2-86 | 5-NO₂ | N | OMe | OMe | |

TABLE 55

| Compound No. | Yn | A | R¹ | R² | m.p. (° C.) or RI ($n_D^{20}$) |
|---|---|---|---|---|---|
| 2-87 | 5-CO₂Et | N | OMe | OMe | |
| 2-88 | 5-COPh | N | OMe | OMe | |
| 2-89 | 6-Me | N | OMe | OMe | |
| 2-90 | 6-Cl | N | OMe | OMe | |
| 2-91 | 4,5-Cl₂ | N | OMe | OMe | |
| 2-92 | 4,5-Me₂ | N | OMe | OMe | |
| 2-93 | 4,5-(OMe)₂ | N | OMe | OMe | |
| 2-94 | 3-Br,5-CF₃ | N | OMe | OMe | |
| 2-95 | 3-Cl,5-CF₃ | N | OMe | OMe | |
| 2-96 | 3,4,5-F₃ | N | OMe | OMe | |
| 2-97 | 4-Me | N | OMe | OEt | 173–175 |
| 2-98 | 4-Cl | N | OMe | OEt | 130–132 |
| 2-99 | 4-Br | N | OMe | OEt | |
| 2-100 | H | CH | OEt | OEt | 92–95 |
| 2-101 | 4-F | CH | OEt | OEt | 131–134 |
| 2-102 | 4-Cl | CH | OEt | OEt | 147–149 |
| 2-103 | 4-Br | CH | OEt | OEt | |
| 2-104 | 4-Me | CH | OEt | OEt | 147–150 |
| 2-105 | 4-CF₃ | CH | OEt | OEt | 134–137 |
| 2-106 | 4-F | N | OEt | OEt | |
| 2-107 | 4-Cl | N | OEt | OEt | |
| 2-108 | 4-Br | N | OEt | OEt | |
| 2-109 | 4-Me | N | OEt | OEt | |
| 2-110 | 4-CF₃ | N | OEt | OEt | |
| 2-111 | 4-Cl | N | OPr | OPr | |
| 2-112 | 4-Cl | CH | OPr-i | OPr-i | |
| 2-113 | 4-Me | CH | OPr-i | OPr-i | |
| 2-114 | 4-Cl | N | OPr-i | OPr-i | |
| 2-115 | 4-Br | N | OPr-i | OPr-i | |
| 2-116 | 4-Cl | N | OCH₂CH=CH₂ | OCH₂CH=CH₂ | |
| 2-117 | 4-Br | N | OCH₂CH=CH₂ | OCH₂CH=CH₂ | |

TABLE 56

| Compound No. | Yn | A | R¹ | R² | m.p. (° C.) or RI ($n_D^{20}$) |
|---|---|---|---|---|---|
| 2-118 | 4-Cl | N | OCH₂C≡CH | OCH₂C≡CH | |
| 2-119 | 4-Br | N | OCH₂C≡CH | OCH₂C≡CH | |
| 2-120 | 4-Cl | N | OCH₂CN | OCH₂CN | |
| 2-121 | 4-Br | N | OCH₂CN | OCH₂CN | |
| 2-122 | 4-Br | N | OCH₂CH₂OMe | OCH₂CH₂OMe | |
| 2-123 | 4-Cl | N | OCH₂CH₂OMe | OCH₂CH₂OMe | |
| 2-124 | 4-Br | N | OCH₂Pr-c | OCH₂Pr-c | |
| 2-125 | 4-Cl | N | OCH₂Pr-c | OCH₂Pr-c | 65–68 |
| 2-126 | H | CH | OBn | OBn | |
| 2-127 | H | N | OBn | OBn | |
| 2-128 | H | N | OBn(4-Cl) | OBn(4-Cl) | |
| 2-129 | H | N | OBn(4-Me) | OBn(4-Me) | |
| 2-130 | H | N | OBn(4-OMe) | OBn(4-OMe) | |
| 2-131 | H | CH | OMe | OPh | |
| 2-132 | H | N | OMe | OPh | |
| 2-133 | H | N | OMe | OPh(4-Cl) | |
| 2-134 | H | N | OMe | OPh(4-Me) | |
| 2-135 | H | N | OMe | OPh(4-OMe) | |
| 2-136 | H | CH | OMe | OCHF₂ | |
| 2-137 | H | N | OMe | OCHF₂ | |
| 2-138 | 4-Cl | CH | OMe | H | 136–139 |
| 2-139 | 4-Me | CH | OMe | H | 136–139 |
| 2-140 | 4-Cl | CH | OEt | H | 118–119 |
| 2-141 | 4-Me | CH | OEt | H | 99–100 |
| 2-142 | 4-Cl | CH | OMe | Me | |
| 2-143 | 4-Me | CH | OMe | Me | |
| 2-144 | 4-CF₃ | CH | OMe | Me | 155–158 |
| 2-145 | 4-Cl | N | OMe | Me | |
| 2-146 | 4-Me | N | OMe | Me | |
| 2-147 | 4-Cl | N | OMe | Pr | |
| 2-148 | 4-Me | N | OMe | Pr | 116–119 |

TABLE 57

| Compound No. | Yn | A | R¹ | R² | m.p. (° C.) or RI ($n_D^{20}$) |
|---|---|---|---|---|---|
| 2-149 | 4-Cl | N | OMe | Pr-c | |
| 2-150 | 4-Br | N | OMe | Pr-c | |
| 2-151 | 4-Me | N | OMe | Pr-c | 130133 |
| 2-152 | 4-Cl | N | OEt | Pr-c | |
| 2-153 | 4-Me | N | OEt | Pr-c | |
| 2-154 | 4-Cl | N | OMe | Et | 109–112 |
| 2-155 | 4-Br | N | OMe | Et | 113–116 |
| 2-156 | 4-Me | N | OMe | Et | |
| 2-157 | 4-Cl | N | OEt | Et | |
| 2-158 | 4-Br | N | OEt | Et | |
| 2-159 | 4-Me | N | OEt | Et | |
| 2-160 | 4-Me | N | OPr | Me | 175–178 |
| 2-161 | 4-Cl | N | OPr | Me | |
| 2-162 | 4-Me | CH | Me | Et | 75–78 |
| 2-163 | 4-Cl | CH | Me | Et | |
| 2-164 | 4-Me | CH | Et | Et | 64–67 |
| 2-165 | 4-Cl | CH | Et | Et | |
| 2-166 | 4-Me | N | Me | SMe | 174–177 |
| 2-167 | 4-Cl | N | SMe | SMe | 179–182 |
| 2-168 | 4-Br | N | SMe | SMe | |
| 2-169 | 4-Me | N | SMe | SMe | |
| 2-170 | 4-Cl | N | OMe | SMe | |
| 2-171 | 4-Me | N | OMe | SMe | |
| 2-172 | 4-Me | N | OMe | Ph | 165–168 |
| 2-173 | 4-Cl | N | NMe₂ | NMe₂ | >300 |
| 2-174 | H | CBr | OMe | OMe | |
| 2-175 | H | CMe | Cl | Cl | |
| 2-176 | 4-Me | COMe | H | H | |
| 2-177 | 4-Cl | COMe | H | H | |
| 2-178 | 4-Me | N | Cl | Ph | 106–109 |
| 2-179 | 4-Cl | N | Cl | Ph | |

TABLE 58

| Compound No. | Yn | A | R¹ | R² | m.p. (° C.) or RI ($n_D^{20}$) |
|---|---|---|---|---|---|
| 2-180 | 4-Cl | CH | C≡CMe | Me | |
| 2-181 | 4-Cl | N | C≡CMe | Me | |
| 2-182 | 4-Cl | CH | CH=CH₂ | Me | |
| 2-183 | 4-Cl | N | CH=CH₂ | Me | |
| 2-184 | 4-Cl | CH | CHO | Me | |
| 2-185 | 4-Cl | N | CHO | Me | |
| 2-186 | 4-Cl | CH | COMe | Me | |
| 2-187 | 4-Cl | N | COMe | Me | |
| 2-188 | 4-Cl | CH | CH₂OMe | Me | |
| 2-189 | 4-Me | CH | CH₂OMe | Me | |
| 2-190 | H | CH | CN | CN | |
| 2-191 | H | CH | CN | Me | |
| 2-192 | H | N | CN | CN | |
| 2-193 | H | N | CN | Me | |
| 2-194 | H | CH | SO₂Me | SO₂Me | |
| 2-195 | H | N | SO₂Me | SO₂Me | |
| 2-196 | H | CH | SO₂Me | Me | |

TABLE 59

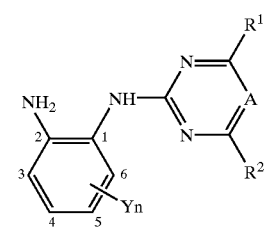

| Compound No. | Yn | A | R¹ | R² | m.p. (° C.) or RI ($n_D^{20}$) |
|---|---|---|---|---|---|
| 3-1 | 3-Me | CH | OMe | OMe | |
| 3-2 | 3-Cl | CH | OMe | OMe | |
| 3-3 | 4-F | CH | OMe | OMe | 120–123 |
| 3-4 | 4-Cl | CH | OMe | OMe | |
| 3-5 | 4-Br | CH | OMe | OMe | 117–118 |
| 3-6 | 4-Me | CH | OMe | OMe | 128–129 |
| 3-7 | 4-Bu-t | CH | OMe | OMe | |
| 3-8 | 4-CF₃ | CH | OMe | OMe | 113–115 |
| 3-9 | 4-OMe | CH | OMe | OMe | |
| 3-10 | 4-OEt | CH | OMe | OMe | 129–132 |
| 3-11 | 4-OPr | CH | OMe | OMe | |
| 3-12 | 4-OCF₃ | CH | OMe | OMe | 85–88 |
| 3-13 | 4-OCH₂CH=CH₂ | CH | OMe | OMe | |
| 3-14 | 4-OCH₂C≡CH | CH | OMe | OMe | |
| 3-15 | 4-OPh | CH | OMe | OMe | |
| 3-16 | 4-OPh(4-Cl) | CH | OMe | OMe | |
| 3-17 | 4-OPh(4-Me) | CH | OMe | OMe | |
| 3-18 | 4-OPh(4-OMe) | CH | OMe | OMe | |
| 3-19 | 4-SMe | CH | OMe | OMe | |
| 3-20 | 4-CH₂OMe | CH | OMe | OMe | |
| 3-21 | 4-COMe | CH | OMe | OMe | |
| 3-22 | 4-COPh | CH | OMe | OMe | |
| 3-23 | 4-CO₂Et | CH | OMe | OMe | |
| 3-24 | 4-Ph | CH | OMe | OMe | 130–132 |

TABLE 60

| Compound No. | Yn | A | R¹ | R² | m.p. (° C.) or RI ($n_D^{20}$) |
|---|---|---|---|---|---|
| 3-25 | 4-Ph(4-Cl) | CH | OMe | OMe | |
| 3-26 | 4-Ph(4-Me) | CH | OMe | OMe | |
| 3-27 | 4-Ph(4-OMe) | CH | OMe | OMe | |
| 3-28 | 4-NO₂ | CH | OMe | OMe | |
| 3-29 | 4-NH₂ | CH | OMe | OMe | |
| 3-30 | 4-NHMe | CH | OMe | OMe | |
| 3-31 | 4-NMe₂ | CH | OMe | OMe | |
| 3-32 | 4-CN | CH | OMe | OMe | 166–169 |
| 3-33 | 5-F | CH | OMe | OMe | |
| 3-34 | 5-Cl | CH | OMe | OMe | 124–125 |
| 3-35 | 5-Me | CH | OMe | OMe | 91–94 |
| 3-36 | 5-CF₃ | CH | OMe | OMe | |
| 3-37 | 5-OMe | CH | OMe | OMe | |
| 3-38 | 5-CO₂Me | CH | OMe | OMe | |
| 3-39 | 5-COPh | CH | OMe | OMe | |
| 3-40 | 6-Me | CH | OMe | OMe | |
| 3-41 | 6-Cl | CH | OMe | OMe | |
| 3-42 | 4,5-Cl₂ | CH | OMe | OMe | |
| 3-43 | 4,6-Me₂ | CH | OMe | OMe | 145–147 |
| 3-44 | 4,5-Me₂ | CH | OMe | OMe | |
| 3-45 | 4,5-(OMe)₂ | CH | OMe | OMe | |
| 3-46 | 3-Br,5-CF₃ | CH | OMe | OMe | |
| 3-47 | 3-Cl,5-CF₃ | CH | OMe | OMe | |
| 3-48 | 3,4,5-F₃ | CH | OMe | OMe | |
| 3-49 | H | N | OMe | OMe | 152–155 |
| 3-50 | 3-Me | N | OMe | OMe | |
| 3-51 | 3-Cl | N | OMe | OMe | |
| 3-52 | 4-F | N | OMe | OMe | 183–186 |
| 3-53 | 4-Cl | N | OMe | OMe | 202–205 |
| 3-54 | 4-Br | N | OMe | OMe | 200–203 |
| 3-55 | 4-I | N | OMe | OMe | 191–194 |

TABLE 61

| Compound No. | Yn | A | R¹ | R² | m.p. (° C.) or RI ($n_D^{20}$) |
|---|---|---|---|---|---|
| 3-56 | 4-Me | N | OMe | OMe | 180–183 |
| 3-57 | 4-Et | N | OMe | OMe | 123–126 |
| 3-58 | 4-Pr | N | OMe | OMe | 136–139 |
| 3-59 | 4-CF₃ | N | OMe | OMe | 177–180 |
| 3-60 | 4-Bu-t | N | OMe | OMe | 140–143 |
| 3-61 | 4-C≡CBu-t | N | OMe | OMe | 161–164 |
| 3-62 | 4-OMe | N | OMe | OMe | 182–185 |
| 3-63 | 4-OEt | N | OMe | OMe | |
| 3-64 | 4-OPr | N | OMe | OMe | |
| 3-65 | 4-OCF₃ | N | OMe | OMe | |
| 3-66 | 4-OCH₂CH=CH₂ | N | OMe | OMe | |
| 3-67 | 4-OCH₂C≡CH | N | OMe | OMe | |
| 3-68 | 4-OPh | N | OMe | OMe | |
| 3-69 | 4-SMe | N | OMe | OMe | |
| 3-70 | 4-COPh | N | OMe | OMe | 175–178 |
| 3-71 | 4-CO₂Me | N | OMe | OMe | 197–200 |
| 3-72 | 4-Ph | N | OMe | OMe | |
| 3-73 | 4-Ph(4-Cl) | N | OMe | OMe | |
| 3-74 | 4-Ph(4-Me) | N | OMe | OMe | |
| 3-75 | 4-Ph(4-OMe) | N | OMe | OMe | |
| 3-76 | 4-NO₂ | N | OMe | OMe | |
| 3-77 | 4-NH₂ | N | OMe | OMe | |
| 3-78 | 4-NHMe | N | OMe | OMe | |
| 3-79 | 4-NMe₂ | N | OMe | OMe | 115–118 |
| 3-80 | 4-CN | N | OMe | OMe | 215–218 |
| 3-81 | 5-F | N | OMe | OMe | |
| 3-82 | 5-Cl | N | OMe | OMe | |
| 3-83 | 5-Me | N | OMe | OMe | 131–134 |
| 3-84 | 5-CF₃ | N | OMe | OMe | |
| 3-85 | 5-OMe | N | OMe | OMe | |
| 3-86 | 5-NO₂ | N | OMe | OMe | |

TABLE 62

| Compound No. | Yn | A | R¹ | R² | m.p. (° C.) or RI ($n_D^{20}$) |
|---|---|---|---|---|---|
| 3-87 | 5-CO₂Et | N | OMe | OMe | |
| 3-88 | 5-COPh | N | OMe | OMe | |
| 3-89 | 6-Me | N | OMe | OMe | |
| 3-90 | 6-Cl | N | OMe | OMe | |
| 3-91 | 4,5-Cl₂ | N | OMe | OMe | |
| 3-92 | 4,5-Me₂ | N | OMe | OMe | |
| 3-93 | 4,5-(OMe)₂ | N | OMe | OMe | |
| 3-94 | 3-Br,5-CF₃ | N | OMe | OMe | |
| 3-95 | 3-Cl,5-CF₃ | N | OMe | OMe | |
| 3-96 | 3,4,5-F₃ | N | OMe | OMe | |
| 3-97 | 4-Me | N | OMe | OEt | 134–137 |
| 3-98 | 4-Cl | N | OMe | OEt | 132–135 |
| 3-99 | 4-Br | N | OMe | OEt | 140–142 |
| 3-100 | H | CH | OEt | OEt | 146–148 |
| 3-101 | 4-F | CH | OEt | OEt | |
| 3-102 | 4-Cl | CH | OEt | OEt | |
| 3-103 | 4-Br | CH | OEt | OEt | |
| 3-104 | 4-Me | CH | OEt | OEt | |
| 3-105 | 4-CF₃ | CH | OEt | OEt | 167–170 |
| 3-106 | 4-F | N | OEt | OEt | |
| 3-107 | 4-Cl | N | OEt | OEt | 163–166 |
| 3-108 | 4-Br | N | OEt | OEt | 172–175 |
| 3-109 | 4-Me | N | OEt | OEt | 158–161 |
| 3-110 | 4-Bu-t | N | OEt | OEt | 128–129 |
| 3-111 | 4-OMe | N | OEt | OEt | 128–129 |
| 3-112 | 4-CF₃ | N | OEt | OEt | |
| 3-113 | 4-Cl | N | OPr | OPr | 145–148 |
| 3-114 | 4-Cl | CH | OPr-i | OPr-i | |
| 3-115 | 4-Me | CH | OPr-i | OPr-i | |
| 3-116 | 4-Cl | N | OPr-i | OPr-i | 179–182 |
| 3-117 | 4-Br | N | OPr-i | OPr-i | |

TABLE 63

| Compound No. | Yn | A | R¹ | R² | m.p. (° C.) or RI ($n_D^{20}$) |
|---|---|---|---|---|---|
| 3-118 | 4-Cl | N | OCH₂CH=CH₂ | OCH₂CH=CH₂ | |
| 3-119 | 4-Br | N | OCH₂CH=CH₂ | OCH₂CH=CH₂ | |
| 3-120 | 4-Cl | N | OCH₂C≡CH | OCH₂C≡CH | |
| 3-121 | 4-Br | N | OCH₂C≡CH | OCH₂C≡CH | |
| 3-122 | 4-Cl | N | OCH₂CN | OCH₂CN | |
| 3-123 | 4-Br | N | OCH₂CN | OCH₂CN | |
| 3-124 | 4-Br | N | OCH₂CH₂OMe | OCH₂CH₂OMe | |
| 3-125 | 4-Cl | N | OCH₂CH₂OMe | OCH₂CH₂OMe | |
| 3-126 | 4-Br | N | OCH₂Pr-c | OCH₂Pr-c | |
| 3-127 | 4-Cl | N | OCH₂Pr-c | OCH₂Pr-c | 156–159 |
| 3-128 | H | CH | OBn | OBn | |
| 3-129 | H | N | OBn | OBn | |
| 3-130 | H | N | OBn(4-Cl) | OBn(4-Cl) | |
| 3-131 | H | N | OBn(4-Me) | OBn(4-Me) | |
| 3-132 | H | N | OBn(4-OMe) | OBn(4-OMe) | |
| 3-133 | H | CH | OMe | OPh | |
| 3-134 | H | N | OMe | OPh | |
| 3-135 | H | N | OMe | OPh(4-Cl) | |
| 3-136 | H | N | OMe | OPh(4-Me) | |
| 3-137 | H | N | OMe | OPh(4-OMe) | |
| 3-138 | H | CH | OMe | OCHF₂ | |
| 3-139 | H | N | OMe | OCHF₂ | |
| 3-140 | 4-Cl | CH | OMe | H | 136–139 |
| 3-141 | 4-Me | CH | OMe | H | 126–129 |
| 3-142 | 4-Cl | CH | OEt | H | 113–115 |
| 3-143 | 4-Me | CH | OEt | H | 103–105 |
| 3-144 | 4-Cl | CH | OMe | Me | |
| 3-145 | 4-Me | CH | OMe | Me | |
| 3-146 | 4-CF₃ | CH | OMe | Me | 134–137 |
| 3-147 | 4-Cl | N | OMe | Me | |
| 3-148 | 4-Me | N | OMe | Me | 202–205 |

TABLE 64

| Compound No. | Yn | A | R¹ | R² | m.p. (° C.) or RI ($n_D^{20}$) |
|---|---|---|---|---|---|
| 3-149 | 4-Cl | N | OMe | Pr | |
| 3-150 | 4-Me | N | OMe | Pr | 133–136 |
| 3-151 | 4-Cl | N | OMe | Pr-c | |
| 3-152 | 4-Br | N | OMe | Pr-c | 163–165 |
| 3-153 | 4-Me | N | OMe | Pr-c | 56–59 |
| 3-154 | 4-Cl | N | OEt | Pr-c | 163–166 |
| 3-155 | 4-Me | N | OEt | Pr-c | 105–108 |
| 3-156 | 4-Cl | N | OMe | Et | 155–158 |
| 3-157 | 4-Br | N | OMe | Et | 162–165 |
| 3-158 | 4-Me | N | OMe | Et | 171–174 |
| 3-159 | 4-Cl | N | OEt | Et | |
| 3-160 | 4-Br | N | OEt | Et | |
| 3-161 | 4-Me | N | OEt | Et | |
| 3-162 | 4-Me | N | OPr | Me | |
| 3-163 | 4-Cl | N | OPr | Me | |
| 3-164 | 4-Me | CH | Me | Et | 92–95 |
| 3-165 | 4-Cl | CH | Me | Et | |
| 3-166 | 4-Me | CH | Et | Et | 91–94 |
| 3-167 | 4-Cl | CH | Et | Et | |
| 3-168 | 4-Me | N | Me | SMe | 180–183 |
| 3-169 | 4-Cl | N | SMe | SMe | 192–195 |
| 3-170 | 4-Br | N | SMe | SMe | |
| 3-171 | 4-Me | N | SMe | SMe | |
| 3-172 | 4-Cl | N | OMe | SMe | |
| 3-173 | 4-Me | N | OMe | SMe | |
| 3-174 | 4-Me | N | OMe | Ph | 170–173 |
| 3-175 | 4-Cl | N | NMe₂ | NMe₂ | 176–179 |
| 3-176 | H | CBr | OMe | OMe | |
| 3-177 | H | CMe | Cl | Cl | |
| 3-178 | 4-Me | COMe | H | H | |
| 3-179 | 4-Cl | COMe | H | H | |

TABLE 65

| Compound No. | Yn | A | R¹ | R² | m.p. (° C.) or RI ($n_D^{20}$) |
|---|---|---|---|---|---|
| 3-180 | 4-Me | N | Cl | Ph | |
| 3-181 | 4-Cl | N | Cl | Ph | |
| 3-182 | 4-Cl | CH | C≡CMe | Me | |
| 3-183 | 4-Cl | N | C≡CMe | Me | |
| 3-184 | 4-Cl | CH | CH=CH₂ | Me | |
| 3-185 | 4-Cl | N | CH=CH₂ | Me | |
| 3-186 | 4-Cl | CH | CHO | Me | |
| 3-187 | 4-Cl | N | CHO | Me | |
| 3-188 | 4-Cl | CH | COMe | Me | |
| 3-189 | 4-Cl | N | COMe | Me | |
| 3-190 | 4-Cl | CH | CH₂OMe | Me | |
| 3-191 | 4-Me | CH | CH₂OMe | Me | |
| 3-192 | H | CH | CN | CN | |
| 3-193 | H | CH | CN | Me | |
| 3-194 | H | N | CN | CN | |
| 3-195 | H | N | CN | Me | |
| 3-196 | H | CH | SO₂Me | SO₂Me | |
| 3-197 | H | N | SO₂Me | SO₂Me | |
| 3-198 | H | CH | SO₂Me | Me | |

BEST MODE FOR CARRYING OUT THE INVENTION

Now, the processes for producing the compound of the present invention, formulation methods and applications will be specifically described with reference to Examples.

PREPARATION EXAMPLE 1

1-(4-methoxypyrimidin-2-yl)-benzimidazole (Compound Number I-667)

Benzimidazole (0.50 g) was dissolved in dimethylformamide (10 ml), and sodium hydride (60% purity, oily) (0.18 g) was added thereto at room temperature. After stirring for 1 hour, 2-chloro-4-methoxypyrimidine (0.62 g) was added at room temperature, followed by stirring for 3 hours. Ice water was added, followed by extraction with ethyl acetate, washing with a saturated sodium chloride aqueous solution and drying over anhydrous magnesium sulfate. The solvent was distilled off, and the residue was purified by silica gel column chromatography to obtain 0.40 g of the desired product as a white powder (m.p. 114–116° C.).

PREPARATION EXAMPLE 2

1-(4,6-dimethoxypyrimidin-2-yl)-2-methylthiobenzimidazole (Compound Number I-4)

2-Methylthiobenzimidazole (0.50 g) was dissolved in dimethylformamide (10 ml), and sodium hydride (60% purity, oily) (0.13 g) was added thereto at room temperature. After stirring for 1 hour, 2-methylsulfonyl-4,6-dimethoxypyrimidine (0.67 g) was added at room temperature, followed by stirring for 8 hours. Ice water was added, followed by extraction with ethyl acetate, washing with a saturated sodium chloride aqueous solution and drying over anhydrous magnesium sulfate. The solvent was distilled off, and the residue was purified by silica gel column chromatography to obtain 0.80 g of the desired product as a white powder (m.p. 135–137° C.).

PREPARATION EXAMPLE 3

1-(4,6-dimethoxypyrimidin-2-yl)-2-methylsulfonylbenzimidazole (Compound Number I-5)

1-(4,6-dimethoxypyrimidin-2-yl)-2-methylthiobenzimidazole (0.70 g) and m-chloroperbenzoic acid (1.30 g) were dissolved in chloroform (30 ml), followed by stirring at room temperature for 3 hours. The reaction liquid was washed with a 5% aqueous potassium carbonate solution and water, and the organic solvent layer was dried over anhydrous magnesium sulfate. The solvent was distilled off, and the residue was purified by silica gel column chromatography to obtain 0.50 g of the desired product as a white powder (m.p. 114–117° C.).

PREPARATION EXAMPLE 4

1-(4,6-dimethoxypyrimidin-2-yl)-2-methoxybenzimidazole (Compound Number I-18)

1-(4,6-dimethoxypyrimidin-2-yl)-2-methylsulfonylbenzimidazole (0.40 g) was dissolved in tetrahydrofuran (20 ml), and sodium methylate (0.50 g) was added thereto under cooling with ice, followed by stirring for 1 hour. Ice water was added, followed by extraction with ethyl acetate, washing with a saturated sodium chloride aqueous solution and drying over anhydrous magnesium sulfate. The solvent was distilled off, and the mixture was purified by silica gel column chromatography to obtain 0.40 g of the desired product as a white powder (m.p. 121–122° C.).

PREPARATION EXAMPLE 5

1-(4,6-dimethoxypyrimidin-2-yl)-2,5-dimethylbenzimidazole (Compound Number I-186)

N'-(4,6-dimethoxypyrimidin-2-yl)-4-methylbenzene-1,2-diamine (2.50 g) was dissolved in acetic acid (20 ml) and acetic anhydride (10 ml), followed by reflux for 4 hours. Water was added, and the crystals were collected by filtration, washed with water and dried. Recrystallization from ethanol was carried out to obtain 1.90 g of the desired product as white feather-like crystals (m.p. 163–166° C.).

PREPARATION EXAMPLE 6

2-amino-1-(4,6-dimethoxypyrimidin-2-yl)-5-methylbenzimidazole (Compound Number I-362)

N'-(4,6-dimethoxypyrimidin-2-yl)-4-methylbenzene-1,2-diamine (2.00 g) was dissolved in ethanol, and cyanogen bromide (1.00 g) was added thereto at room temperature, followed by stirring at 60° C. for 1 hour. Water was added, and the crystals were collected by filtration, washed with water and dried to obtain 2.03 g of the desired product as a white powder (m.p. at least 300° C.)

PREPARATION EXAMPLE 7

2-chloro-1-(4,6-dimethoxypyrimidin-2-yl)-5-methylbenzimidazole (Compound Number I-258)

2-Amino-1-(4,6-dimethoxypyrimidin-2-yl)-5-methylbenzimidazole (1.67 g) and copper(II)chloride (0.94 g) were suspended in acetonitrile (30 ml), and tert-butyl nitrite (0.90 g) was added thereto at room temperature, followed by reflux for 30 minutes. Water was added, followed by extraction with ethyl acetate, washing with a saturated sodium chloride aqueous solution and drying over anhydrous magnesium sulfate. The solvent was distilled off, and the residue was purified by silica gel column chromatography to obtain 1.48 g of the desired product as white feather-like crystals (m.p. 145–148° C.).

PREPARATION EXAMPLE 8

1-(4,6-dimethoxypyrimidin-2-yl)-5-methyl-2-trifluoromethylbenzimidazole (Compound Number I-298)

2-(4,6-dimethoxypyrimidin-2-yl)amino-5-methyltrifluoroacetic anilide (0.60 g) and para-toluenesulfonic acid (0.05 g) were dissolved in toluene (30 ml), followed by reflux for 5 hours. Water and ethyl acetate were added, and the organic layer was washed with a saturated sodium hydrogencarbonate solution and a saturated sodium chloride aqueous solution and dried over anhydrous magnesium sulfate. The solvent was distilled off, and the residue was purified by silica gel column chromatography to obtain 0.56 g of the desired product as a white powder (m.p. 93–96° C.).

PREPARATION EXAMPLE 9

1-(4,6-dichloro-[1,3,5]triazin-2-yl)-2-methylbenzimidazole (Compound Number I-1066)

2-Methylbenzimidazole (5.0 g) was dissolved in tetrahydrofuran (50 ml), and sodium hydride (60% purity, oily) (1.6 g) was added thereto at room temperature. After stirring for 1 hour, cyanuric chloride (7.0 g) was added at room temperature, followed by stirring for 3 hours. Ice water was added, followed by extraction with ethyl acetate, washing with a saturated sodium chloride aqueous solution and drying over anhydrous magnesium sulfate. The solvent was distilled off, and the residue was purified by silica gel column chromatography to obtain 2.6 g of the desired product as a white powder (m.p. at least 300° C.)

PREPARATION EXAMPLE 10

1-(4,6-dimethylthio-[1,3,5]triazin-2-yl)-2-methylbenzimidazole (Compound Number I-1042)

1-(4,6-dichloro-[1,3,5]triazin-2)-2-methylbenzimidazole (0.5 g) was dissolved in methanol (10 ml), and a 15% aqueous methyl mercaptan sodium salt solution (0.25 g) was added at room temperature, followed by stirring for 1 hour. After the completion of the reaction, the reaction liquid was poured into ice water, and the crystals thus deposited were collected by filtration, washed with water and dried to obtain 0.46 g of the desired product as a white powder (m.p. 176–179° C.)

PREPARATION EXAMPLE 11

5-chloro-1-(4,6-dimethoxy-[1,3,5]triazin-2-yl)-2-methylbenzimidazole (Compound Number I-215)

4-Chloro-N'-(4,6-dimethoxy-[1,3,5]triazin-z-2-yl)benzene-1,2-diamine (0.5 g) was dissolved in acetic acid (10 ml), and acetic anhydride (10 ml) followed by reflux for 4 hours. Water was added, and the crystals were collected by filtration, washed with water and dried. Recrystallization from ethanol was carried out to obtain 0.47 g of the desired product as white feather-like crystals (m.p. 173–176° C.)

PREPARATION EXAMPLE 12

5-chloro-1-(4,6-dimethoxy-[1,3,5]triazin-2-yl)-2-methylbenzimidazole (Compound Number I-215)

2-Nitro-4-chloro-N-(4,6-dimethoxy-[1,3,5]triazin-2-yl) aniline (0.5 g) and iron powder (0.3 g) were dissolved in acetic acid (10 ml) and acetic anhydride (5 ml), followed by reflux for 4 hours. The reaction mixture was cooled to room temperature, followed by filtration. The filtrate was concentrated under reduced pressure, water was added to the residue, and the crystals were collected by filtration, washed with water and dried. Recrystallization from ethanol was carried out to obtain 0.39 g of the desired product as white feather-like crystals (m.p. 173–176° C.)

PREPARATION EXAMPLE 13

2-amino-5-chloro-1-(4,6-dimethoxy-[1,3,5]triazin-2-yl)benzimidazole (Compound Number I-368)

4-Chloro-N'-(4,6-dimethoxy-[1,3,5]triazin-2-yl)benzene-1,2-diamine (1.5 g) was dissolved in ethanol (50 ml), and cyanogen bromide (0.6 g) was added thereto at room temperature, followed by stirring at 60° C. for 1 hour. Water was added, and the crystals were collected by filtration, washed with water and dried to obtain 1.2 g of the desired product as a pink powder (m.p. 293–296° C.)

PREPARATION EXAMPLE 14

2,5-dichloro-1-(4,6-dimethoxy-[1,3,5]triazin-2-yl)benzimidazole (Compound Number I-277)

2-Amino-5-chloro-1-(4,6-dimethoxy-[1,3,5]triazin-2-yl)benzimidazole (1.1 g) and copper(II)chloride (0.6 g) were suspended in acetonitrile (50 ml), and tert-butyl nitrite (0.5 g) was added thereto at room temperature, followed by reflux for 30 minutes. Water was added, followed by extraction with ethyl acetate, washing with a saturated sodium chloride aqueous solution and drying over anhydrous magnesium sulfate. The solvent was distilled off, and the residue was purified by silica gel column chromatography to obtain 0.5 g of the desired product as white feather-like crystals (m.p. 146–149° C.).

PREPARATION EXAMPLE 15

1-(4,6-dimethoxy-[1,3,5]triazin-2-yl)-5-methyl-2-trifluoromethylbenzimidazole (Compound Number I-312)

2-(4,6-dimethoxy-[1,3,5]triazin-2-yl)amino-5-methyltrifluoroacetic anilide (1.0 g) and para-toluenesulfonic acid (0.05 g) were dissolved in chlorobenzene (30 ml), followed by reflux for 5 hours. Water and ethyl acetate were added, and the organic layer was washed with a saturated sodium hydrogencarbonate solution and a saturated sodium chloride aqueous solution and dried over anhydrous magnesium sulfate. The solvent was distilled off, and the residue was purified by silica gel column chromatography to obtain 0.23 g of the desired product as a white powder (m.p. 137–140° C.).

Now, $^{1}$H-NMR (CDCl$_3$/TMS, δ (ppm)) data of some among examples of the compounds of the present invention, will be shown below.

PREPARATION EXAMPLE 18

2-(4,6-dimethoxypyrimidin-2-yl)amino-5-methyltrifluoroacetic anilide (Compound Number 1-196)

N'-(4,6-dimethoxypyrimidin-2-yl)-4-methylbenzene-1,2-diamine (0.80 g) was dissolved in pyridine (10 ml), and trifluoroacetic anhydride (0.97 g) was added thereto under cooling with ice salt. After stirring for 1 hour, diluted hydrochloric acid was added thereto, followed by extraction with ethyl acetate, washing with diluted hydrochloric acid and a saturated sodium chloride aqueous solution and drying over anhydrous magnesium sulfate. The solvent was distilled off, and the residue was purified by silica gel column chromatography to obtain 0.88 g of the desired product as a white powder (m.p. 144–147° C.).

TABLE 66

| Compound No. | $^{1}$H-NMR δ(ppm), solvent CDCl$_3$ |
|---|---|
| I-30 | 2.99(6H, s); 4.03(6H, s); 5.99(1H, s); 7.03–7.09(1H, m); 7.17–7.22(1H, m); 7.48–7.51(1H, m); 7.84–7.85(1H, m); 8.01(1H, s) |
| I-34 | 3.64(6H, s); 5.92(1H, s); 7.42–7.36(5H, m); 7.56–7.60(2H, m); 7.58–7.88(1H, m); 8.20–8.23(1H, m) |
| I-840 | 1.41(6H, d, J=6.3Hz); 2.52(3H, s); 2.98(3H, s); 5.39–5.47(1H, m); 6.46(1H, s); 7.26–7.33(2H, m); 7.69–7.72(1H, m); 8.25–8.28(1H, m) |
| I-872 | 1.01(3H, t, J=7.5Hz); 1.49–1.57(2H, m); 1.80–1.87(2H, m); 2.51(3H, s); 4.50(2H, t, J=6.57Hz); 6.45(1H, s); 7.33–7.43(2H, m); 7.82–7.85(1H, m); 8.55–8.59(1H, m); 9.05(1H, s) |
| I-906 | 1.66–2.11(8H, m); 2.45(3H, s); 5.51–5.56(1H, m); 6.36(1H, s); 7.28–7.41(2H, m); 7.81–7.83(1H, m); 8.45–8.52(1H, m); 9.05(1H, s) |
| I-907 | 1.65–2.04(8H, m); 2.51(3H, s); 3.98(3H, s); 5.51–5.55(1H, m); 6.46(1H, s); 7.26–7.34(2H, m); 7.68–7.73(1H, m); 8.25–8.31(1H, m) |
| I-959 | 1.03(3H, t, J=7.41Hz); 1.81–1.89(2H, m); 2.76(2H, t, J=7.14Hz); 3.00(3H, s); 4.08(3H, s); 6.51(1H, s); 7.27–7.33(2H, m); 7.70–7.73(1H, m); 8.28–8.34(1H, m) |
| I-960 | 1.03(3H, t, J=7.29Hz); 1.81–1.89(2H, m); 2.77(2H, t, J=7.29Hz); 4.07(3H, s); 6.58(1H, s); 7.30–7.37(2H, m); 7.71–7.74(1H, m); 8.00–8.05(1H, m) |

Now, Preparation Examples of intermediates for the synthesis of the compounds of the present invention will be shown below.

PREPARATION EXAMPLE 16

N-(4,6-dimethoxypyrimidin-2-yl)-4-methyl-2-nitroaniline (Compound Number 2-6)

N-formyl-4-methyl-2-nitroaniline (25.00 g) was dissolved in dimethylformamide (400 ml), and sodium hydride (60% purity, oily) (6.11 g) was added thereto at room temperature. After stirring for 10 minutes, 2-methylsulfonyl-4,6-dimethoxypyrimidine (30.28 g) was added at room temperature, followed by stirring for 3 hours. A 10% NaOH aqueous solution was added thereto, and the crystals were collected by filtration, washed with water and dried to obtain 37.50 g of the desired product as a yellow powder (m.p. 158–161° C.).

PREPARATION EXAMPLE 17

N'-(4,6-dimethoxypyrimidin-2-yl)-4-methylbenzene-1,2-diamine (Compound Number 3-6)

N-(4,6-dimethoxypyrimidin-2-yl)-4-methyl-2-nitroaniline (37.50 g) was dissolved in ethyl acetate (600 ml), and 10% palladium carbon (3.75 g) was added thereto. Stirring was carried out at room temperature under normal pressure in an atmosphere of hydrogen for 4 hours, followed by filtration. The solvent of the filtrate was distilled off to obtain 32.70 g of the desired product as a white powder (m.p. 128–129° C.)

PREPARATION EXAMPLE 19

N-(4,6-dimethoxy-[1,3,5]triazin-2-yl)-4-methyl-2-nitroaniline (Compound Number 2-56)

N-formyl-4-methyl-2-nitroaniline (7.2 g) was dissolved in tetrahydrofuran (50 ml), and sodium hydride (60% purity, oily) (2.0 g) was added thereto at room temperature. After stirring for 10 minutes, 2-chloro-4,6-dimethoxy-[1,3,5]triazine (7.0 g) was added at room temperature, followed by stirring for 3 hours. A 10% aqueous sodium hydroxide solution was added thereto, and the crystals were collected by filtration, washed with water and dried to obtain 10.0 g of the desired product as a yellow powder (m.p. 189–191° C.)

SYNTHESIS EXAMPLE 20

N'-(4,6-dimethoxy-[1,3,5]triazin-2-yl)-4-methylbenzene-1,2-diamine (Compound Number 3-56)

N-(4,6-dimethoxy-[1,3,5]triazin-2-yl)-4-methyl-2-nitroaniline (10 g) was dissolved in ethyl acetate (50 ml) and water (50 ml), and 10 g of iron power and acetic acid (2 ml) were added thereto, followed by reflux for 2 hours. Insoluble matters were removed by filtration, and the ethyl acetate layer was washed with a saturated sodium chloride aqueous solution and dried over anhydrous magnesium sulfate. The solvent was distilled off to obtain 8.8 g of the desired product as a white powder (m.p. 180–183° C.).

PREPARATION EXAMPLE 21

2-(4,6-dimethoxy-[1,3,5]triazin-2-yl)amino-5-methyltrifluoroacetic anilide (Compound Number 1-210)

N'-(4,6-dimethoxy-[1,3,5]triazin-2-yl)-4-methylbenzene-1,2-diamine (1.0 g) was dissolved in pyridine (50 ml), and trifluoroacetic anhydride (0.8 g) was added thereto under cooling with ice salt. After stirring for 1 hour, diluted hydrochloric acid was added thereto, followed by extraction with ethyl acetate, washing with diluted hydrochloric acid and a saturated sodium chloride aqueous solution and drying over anhydrous magnesium sulfate. The solvent was distilled off, and the residue was purified by silica gel column chromatography to obtain 1.3 g of the desired product as a white powder (m.p. 195–198° C.).

PREPARATION EXAMPLE 22

4-chloro-N-(4,6-dimethoxy-[1,3,5]triazin-2-yl)-2-nitroaniline (Compound Number 2-53)

4-Chloro-2-nitroaniline (5.0 g) and sodium hydrogencarbonate (3.6 g) were dissolved in tetrahydrofuran (50 ml), and cyanuric chloride (8.0 g) was added thereto, followed by stirring for 8 hours. To the reaction solution, 28% sodium methylate (11.2 g) was added, followed by reflux for 1 hour. Water was added thereto, followed by extraction with ethyl acetate, washing with a saturated sodium chloride aqueous solution and drying over anhydrous magnesium sulfate. The solvent was distilled off, and the residue was subjected to recrystallization from ethanol to obtain 6.3 of the desired product as a yellow powder (m.p. 206–208° C.).

The agricultural/horticultural fungicides of the present invention contain triazinylbenzimidazole derivatives represented by the general formula [I] as the active ingredients. When the compounds of the present invention are used for agricultural/horticultural fungicides, the active ingredient can be used in appropriate formulations depending on the purpose. The active ingredient is usually diluted with an inert liquid or solid carrier and is used in an appropriate dosage form such as a dust, a wettable powder, an emulsifiable concentrate or a granule by blending it with a surfactant and other ingredients, depending on its use.

Preferable examples of carriers include solid carriers such as talc, bentonite, clay, kaolin, diatomaceous earth, white carbon, vermiculite, slaked lime, silica sand, ammonium sulfate and urea and liquid carriers such as isopropyl alcohol, xylene, cyclohexanone and methylnaphthalene. Examples of surfactants and dispersants include dinaphthylmethanesulfonates, alcohol-sulfuric acid ester salts, alkylarylsulfonates, lignin sulfonate, polyoxyethylene glycol ether, polyoxyethylene alkyl aryl ethers and polyoxyethylene sorbitan monoalkylate. Examples of adjuvants include carboxymethyl cellulose and the like. These formulations are applied after diluted to appropriate concentrations or directly.

The agricultural/horticultural fungicides of the present invention can be used for foliage treatment, soil treatment or submerged treatment. The blending proportion of the active ingredient is suitably selected depending on the case. However, the preferable proportion is from 0.1 to 20% (by weight) in the cases of a dust or a granule, and from 5 to 80% (by weight) in the cases of an emulsifiable concentrate or a wettable powder.

The dose of the agricultural/horticultural fungicides of the present invention depends on the type of the compound to be used, the disease to be controlled, the tendency of disease development, the degrees of the damage, the environmental conditions and the type of the formulation to be used. For example, for direct use as a dust or a granule, the dose of the active ingredient is selected suitably within a range of from 0.1 g to 5 kg, preferably from 1 g to 1 kg, per 10 are. For use in a liquid state as an emulsifiable concentrate or a wettable powder, the dose is selected suitably within a range of from 0.1 ppm to 10,000 ppm, preferably from 1 to 3,000 ppm.

The compounds of the present invention in the above formulations can control plant diseases caused by Oomycetes, Ascomycetes, Deuteromycetes and Basidiomycetes. Specific but non-restrictive examples of microorganisms are given below. *Pseudoperonospora* genus such as *Pseudoperonospora cubensis, Erysiphe* genus such as *Erysiphe graminis, Venturia* genus such as *Venturia inaequalis, Pyricularia* genus such as *Pyricularia oryzae, Botrytis* genus such as *Botrytis cinerea, Rhizoctonia* genus such as *Rhizoctonia solani* and *Puccinia* genus such as *Puccinia recondita*.

The compounds of the present invention can be used in combination with insecticides, other fungicides, herbicides, plant growth regulators or fertilizers, as the case requires. Now, typical formulations of the agricultural/horticultural fungicides of the present invention will be described with reference to Formulation Examples. Hereinafter, "%" means "% by weight".

FORMULATION EXAMPLE 1

Dust b 2% of Compound (I-45), 5% of diatomaceous earth and 93% of clay were uniformly mixed and pulverized to give a dust.

FORMULATION EXAMPLE 2

Wettable Powder

50% of Compound (I-170), 45% of diatomaceous earth, 2% of sodium dinaphthylmethanedisulfonate and 3% of sodium lignin sulfonate were uniformly mixed and pulverized to give a wettable powder.

FORMULATION EXAMPLE 3

Emulsifiable Concentrate

30% of Compound (I-309), 20% of cyclohexanone, 11% of polyoxyethylene alkyl aryl ether, 4% of calcium alkylbenzenesulfonate and 35% of methylnaphthalene were uniformly dissolved to give an emulsifiable concentrate.

FORMULATION EXAMPLE 4

Granule

5% of Compound (I-121), 2% of the sodium salt of the lauryl alcohol sulfuric ester, 5% of sodium lignin sulfonate, 2% of carboxymethyl cellulose and 86% of clay were uniformly mixed and pulverized. The resulting mixture was kneaded with 20% of water, granulated to 14 to 32 mesh by means of an extrusion granulator and dried to give a granule.

Now, the effects of the agricultural/horticultural fungicides of the present invention will be described with reference to specific Test Example.

TEST EXAMPLE 1

Test for Preventive Effect on Wheat Powdery Mildew

9 Wheat seeds (variety: Norin-61-go) were sown in each 9 cm×9 cm polyvinyl chloride pot, grown in a greenhouse for 8 days, then treated with 10 ml per pot of aqueous solutions of wettable powders prepared in accordance with Formulation Example 2, at a concentration of 500 ppm in terms of the active ingredients and dried in the air. Then, the seedlings were inoculated with *Erysiphe graminis* spores by sprinkle over the plant and placed in a greenhouse of from 20 to 25° C. 10 days after the inoculation, the total diseases area of the first leaves in each pot was observed and evaluated on the basis of the standards shown in Table 67. The results are shown in Tables 68 and 69.

TABLE 67

| Evaluation | |
|---|---|
| A | No diseased area |
| B | Diseased area of less than 25% |
| C | Diseased area of at least 25% but less than 50% |
| D | Diseased area of at least 50% |

TABLE 68

| Compound No. | Biological effectiveness |
|---|---|
| I-1 | A |
| I-2 | A |
| I-3 | A |
| I-6 | B |
| I-7 | A |
| I-10 | B |
| I-22 | A |
| I-23 | A |
| I-25 | A |
| I-26 | A |
| I-27 | B |
| I-29 | B |
| I-30 | B |
| I-35 | B |
| I-38 | B |
| I-40 | B |
| I-41 | A |
| I-45 | A |
| I-66 | A |
| I-82 | A |
| I-83 | B |
| I-84 | A |
| I-85 | A |
| I-87 | A |
| I-88 | B |
| I-91 | B |
| I-111 | B |
| I-112 | B |
| I-113 | B |
| I-114 | B |
| I-116 | B |
| I-122 | B |
| I-130 | A |
| I-131 | A |
| I-132 | A |
| I-133 | A |
| I-134 | A |
| I-135 | A |
| I-136 | B |
| I-141 | A |
| I-175 | A |
| I-176 | A |
| I-181 | B |
| I-183 | B |
| I-184 | A |
| I-185 | A |
| I-186 | A |
| I-188 | A |
| I-189 | A |
| I-192 | B |
| I-195 | B |

TABLE 68-continued

| Compound No. | Biological effectiveness |
|---|---|
| I-199 | B |
| I-200 | A |
| I-201 | A |
| I-202 | B |
| I-203 | B |
| I-204 | A |
| I-208 | B |
| I-209 | B |
| I-212 | B |
| I-214 | A |
| I-215 | A |
| I-216 | A |
| I-217 | A |
| I-218 | A |
| I-219 | A |
| I-220 | B |
| I-221 | B |
| I-222 | B |
| I-225 | A |
| I-226 | A |
| I-229 | A |
| I-232 | B |
| I-234 | A |
| I-235 | A |
| I-239 | A |
| I-242 | A |
| I-250 | B |
| I-251 | A |
| I-255 | A |
| I-256 | A |
| I-258 | A |
| I-259 | A |
| I-260 | A |
| I-261 | B |
| I-263 | A |
| I-271 | A |
| I-272 | A |
| I-277 | B |
| I-279 | A |
| I-295 | A |
| I-296 | A |
| I-298 | A |
| I-299 | A |
| I-300 | A |
| I-301 | A |
| I-307 | A |
| I-309 | A |
| I-310 | A |
| I-311 | A |
| I-312 | A |
| I-313 | A |
| I-314 | A |
| I-315 | B |
| I-316 | B |
| I-318 | A |
| I-321 | A |
| I-327 | A |
| I-332 | B |
| I-333 | A |
| I-334 | A |
| I-335 | A |
| I-336 | A |
| I-346 | A |
| I-358 | A |
| I-359 | A |
| I-360 | B |
| I-362 | A |
| I-364 | A |
| I-366 | A |
| I-368 | B |
| I-369 | B |
| I-375 | A |
| I-376 | B |
| I-377 | A |
| I-378 | A |

TABLE 68-continued

| Compound No. | Biological effectiveness |
|---|---|
| I-379 | A |
| I-380 | A |
| I-381 | A |
| I-388 | A |
| I-389 | B |
| I-394 | A |
| I-400 | A |
| I-404 | B |
| I-405 | A |
| I-406 | A |
| I-423 | A |
| I-424 | A |
| I-438 | A |
| I-457 | B |
| I-458 | A |
| I-461 | A |
| I-462 | B |
| I-465 | B |

TABLE 69

| Compound No. | Biological effectiveness |
|---|---|
| I-479 | A |
| I-480 | A |
| I-482 | A |
| I-483 | A |
| I-486 | A |
| I-490 | A |
| I-498 | A |
| I-499 | A |
| I-501 | A |
| I-502 | A |
| I-503 | A |
| I-507 | A |
| I-508 | B |
| I-510 | A |
| I-511 | A |
| I-514 | A |
| I-515 | A |
| I-516 | A |
| I-530 | A |
| I-531 | A |
| I-534 | A |
| I-543 | A |
| I-544 | A |
| I-545 | A |
| I-546 | A |
| I-550 | A |
| I-573 | B |
| I-580 | A |
| I-592 | A |
| I-595 | B |
| I-601 | A |
| I-667 | B |
| I-669 | B |
| I-670 | B |
| I-671 | B |
| I-672 | B |
| I-675 | B |
| I-682 | A |
| I-683 | A |
| I-690 | A |
| I-692 | B |
| I-693 | A |
| I-694 | B |
| I-695 | A |
| I-704 | B |
| I-705 | A |
| I-726 | B |

TABLE 69-continued

| Compound No. | Biological effectiveness |
|---|---|
| I-731 | B |
| I-752 | A |
| I-758 | A |
| I-762 | A |
| I-767 | B |
| I-768 | A |
| I-769 | A |
| I-771 | A |
| I-772 | A |
| I-775 | A |
| I-804 | A |
| I-805 | B |
| I-806 | B |
| I-809 | B |
| I-818 | B |
| I-831 | B |
| I-839 | A |
| I-840 | B |
| I-872 | B |
| I-883 | A |
| I-885 | B |
| I-894 | B |
| I-895 | B |
| I-903 | B |
| I-904 | B |
| I-915 | A |
| I-958 | B |
| I-959 | A |
| I-960 | A |
| I-962 | A |
| I-964 | B |
| I-965 | A |
| I-967 | A |
| I-999 | A |
| I-1004 | A |
| I-1019 | A |
| I-1022 | A |
| I-1043 | A |
| I-1046 | A |
| I-1048 | A |
| I-1058 | A |
| I-1059 | A |
| I-1064 | B |
| I-1071 | A |
| I-1079 | B |
| I-1082 | B |
| I-1085 | A |
| I-1086 | B |
| I-1087 | A |
| I-1088 | A |
| I-1090 | B |
| I-1093 | A |
| I-1094 | A |
| I-1095 | A |
| I-1096 | A |
| I-1098 | A |
| I-1103 | B |
| I-1104 | B |
| I-1106 | B |
| I-1123 | B |
| I-1147 | B |

The agricultural/horticultural fungicides of the present invention have a broad disease control spectrum, and have an excellent effect particularly on wheat powdery mildew. Further, they have high controlling effects on cucumber downy mildew, apple scab, rice blast, cucumber gray mold, rice sheath blight and wheat brown leaf rust, and are excellent in residual effectiveness and rain-fastness without damaging crops, and thus they are useful as agricultural/horticultural fungicides.

What is claimed is:

1. A pyrimidinylbenzimidazole compound represented by formula [I]:

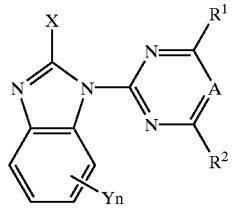

{wherein A is $CR^3$, each of $R^1$ and $R^2$ which are independent of each other, is a hydrogen atom, a halogen atom, a ($C_1$–$C_6$) alkyl group, a ($C_2$–$C_6$) alkenyl group, a ($C_2$–$C_6$) alkynyl group, a ($C_3$–$C_6$) cycloalkyl group, a ($C_1$–$C_4$) haloalkyl group, a ($C_1$–$C_6$) alkoxy group, a ($C_2$–$C_6$) alkenyloxy group, a ($C_2$–$C_6$) alkynyloxy group, a ($C_3$–$C_6$) cycloalkoxy group, a ($C_1$–$C_4$) haloalkoxy group, a cyano ($C_1$–$C_4$) alkyloxy group, a ($C_1$–$C_4$) alkoxy ($C_1$–$C_4$) alkyloxy group, a ($C_3$–$C_6$) cycloalkyl ($C_1$–$C_4$) alkoxy group, a benzyloxy group [said group may be substituted by a halogen atom, a ($C_1$–$C_4$) alkyl group or a ($C_1$–$C_4$) alkoxy group], a ($C_1$–$C_6$) alkylthio group, a ($C_1$–$C_4$) alkoxy ($C_1$–$C_4$) alkyl group, a phenoxy group [said group may be substituted by a halogen atom, a ($C_1$–$C_4$) alkyl group or a ($C_1$–$C_4$) alkoxy group], a ($C_1$–$C_4$) alkylcarbonyl group, a formyl group, a phenyl group, a di($C_1$–$C_4$) alkylamino group, a cyano group or a ($C_1$–$C_6$) alkylsulfonyl group, $R^3$ is a hydrogen atom, a ($C_1$–$C_6$) alkyl group, a ($C_1$–$C_6$) alkoxy group or a halogen atom, X is a hydrogen atom, a halogen atom, a nitro group, a cyano group, a ($C_1$–$C_6$) alkyl group, a ($C_2$–$C_6$) alkenyl group, a ($C_2$–$C_6$) alkynyl group, a ($C_3$–$C_6$) cycloalkyl group, a benzyl group [said group may be substituted by a halogen atom, a ($C_1$–$C_4$) alkyl group or a ($C_1$–$C_4$) alkoxy group], a ($C_1$–$C_6$) alkoxy group, a ($C_2$–$C_6$) alkenyloxy group, a ($C_2$–$C_6$) alkynyloxy group, a ($C_1$–$C_6$) alkylthio group, a ($C_1$–$C_6$) alkylsulfonyl group, a phenoxy group, a ($C_1$–$C_4$) alkoxy ($C_1$–$C_4$) alkyl group, a ($C_1$–$C_4$) haloalkyl group, a ($C_1$–$C_4$) haloalkoxy group, a ($C_1$–$C_4$) alkylcarbonyl group, a ($C_1$–$C_4$) alkoxycarbonyl group, an amino group, a mono($C_1$–$C_4$) alkylamino group, a di($C_1$–$C_4$) alkylamino group, an anilino group or a phenyl group [said group may be substituted by a halogen atom, a ($C_1$–$C_4$) alkyl group or a ($C_1$–$C_4$) alkoxy group], Y is a halogen atom, a nitro group, a cyano group, a ($C_1$–$C_6$) alkyl group, a ($C_2$–$C_6$) alkenyl group, a ($C_2$–$C_6$) alkynyl group, a ($C_1$–$C_6$) alkoxy group, a ($C_2$–$C_6$) alkenyloxy group, a ($C_2$–$C_6$) alkynyloxy group, a ($C_1$–$C_4$) haloalkoxy group, a ($C_1$–$C_6$) alkylthio group, a ($C_1$–$C_4$) alkoxy ($C_1$–$C_4$) alkyl group, a ($C_1$–$C_4$) haloalkyl group, a ($C_1$–$C_4$) alkylcarbonyl group, a ($C_1$–$C_4$) alkoxycarbonyl group, a benzoyl group, an amino group, a mono($C_1$–$C_4$) alkylamino group, a di($C_1$–$C_4$) alkylamino group, a phenyl group [said group may be substituted by a halogen atom, a ($C_1$–$C_4$) alkyl group or a ($C_1$–$C_4$) alkoxy group] or a phenoxy group [said group may be substituted by a halogen atom, a ($C_1$–$C_4$) alkyl group or a ($C_1$–$C_4$) alkoxy group], and n is 0 or an integer of from 1 to 3}.

2. An anilinopyrimidine compound represented by the formula [XVII]:

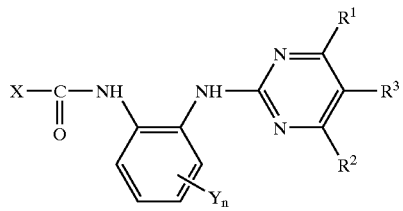

{wherein each of $R^1$ and $R^2$ which are independent of each other, is a hydrogen atom, a halogen atom, a ($C_1$–$C_6$) alkyl group, a ($C_2$–$C_6$) alkenyl group, a ($C_2$–$C_6$) alkynly group, a ($C_3$–$C_6$) cycloalkyl group, a ($C_1$–$C_4$) haloalkyl group, a ($C_1$–$C_6$) alkoxy group, a ($C_2$–$C_6$) alkenyloxy group, a ($C_2$–$C_6$) alkynyloxy group, a ($C_3$–$C_6$) cycloalkoxy group, a ($C_1$–$C_4$) haloalkoxy group, a cyano ($C_1$–$C_4$) alkyloxy group, a ($C_1$–$C_4$) alkoxy ($C_1$–$C_4$) alkyloxy group, a ($C_3$–$C_6$) cycloalkyl ($C_1$–$C_4$) alkoxy group, a benzyloxy group [said group may be substituted by a halogen atom, a ($C_1$–$C_4$) alkyl group or a ($C_1$–$C_4$) alkoxy group], a ($C_1$–$C_6$) alkylthio group, a ($C_1$–$C_4$) alkoxy ($C_1$–$C_4$) alkyl group, a phenoxy group [said group may be substituted by a halogen atom, a ($C_1$–$C_4$) alkyl group or a ($C_1$–$C_4$) alkoxy group], a ($C_1$–$C_4$) alkylcarbonyl group, a formyl group, a phenyl group, a di($C_1$–$C_4$) alkylamino group, a cyano group or a ($C_1$–$C_6$) alkylsulfonyl group, $R^3$ is a hydrogen atom, a ($C_1$–$C_6$) alkyl group, a ($C_1$–$C_6$) alkoxy group or a halogen atom, X is a hydrogen atom, a ($C_1$–$C_6$) alkyl group, a ($C_2$–$C_6$) alkenyl group, a ($C_2$–$C_6$) alkynyl group, a ($C_3$–$C_6$) cycloalkyl group a benzyl group [said group may be substituted by a halogen atom, a ($C_1$–$C_4$) alkyl group or a ($C_1$–$C_4$) alkoxy group], a ($C_1$–$C_4$) alkoxy group, a ($C_2$–$C_6$) alkenyloxy group, a ($C_2$–$C_6$) alkynyloxy group, a ($C_1$–$C_6$) alkylthio group, a ($C_1$–$C_6$) alkylsulfonyl group, a phenoxy group, a ($C_1$–$C_4$) alkoxy ($C_1$–$C_4$) alkyl group, a ($C_1$–$C_4$) haloalkyl group, a ($C_1$–$C_4$) haloalkoxy group, a ($C_1$–$C_4$) alkylcarbonyl group, a ($C_1$–$C_4$) alkoxycarbonyl group, an amino group, a mono ($C_1$–$C_4$) alkylamino group, a di($C_1$–$C_4$) alkylamino group, an anilino group or a phenyl group [said group may be substituted by a halogen atom, a ($C_1$–$C_4$) alkyl group or a ($C_1$–$C_4$) alkoxy group], Y is a halogen atom, a nitro group, a cyano group, a ($C_1$–$C_6$) alkyl group, a ($C_2$–$C_6$) alkenyl group, a ($C_2$–$C_6$) alkynyl group, a ($C_1$–$C_6$) alkoxy group, a ($C_2$–$C_6$) alkenyloxy group, a ($C_2$–$C_6$) alkynyloxy group, a ($C_1$–$C_4$) haloalkoxy group, a ($C_1$–$C_6$) alkylthio group, a ($C_1$–$C_4$) alkoxy ($C_1$–$C_4$) alkyl group, a ($C_1$–$C_4$) haloalkyl group, a ($C_1$–$C_4$) alkylcarbonyl group, a ($C_1$–$C_4$) alkoxycarbonyl group, a benzoyl group, an amino group, a mono ($C_1$–$C_4$) alkylamino group, a di($C_1$–$C_4$) alkylamino group, a phenyl group [said group may be substituted by a halogen atom, a ($C_1$–$C_4$) alkyl group or a ($C_1$–$C_4$) alkoxy group] or a phenoxy group [said group may be substituted by a halogen atom, a ($C_1$–$C_4$) alkyl group or a ($C_1$–$C_4$) alkoxy group], and n is 0 or an integer of from 1 to 3}.

3. An agricultural/horticultural fungicidal composition containing the pyrimidinylbenzimidazole compound as defined in claim 1, as the active ingredient and an agriculturally/horticulturally acceptable inert component.

4. The pyrimidinylbenzimidazole compound according to claim 1, wherein each of $R^1$ and $R^2$ which are independent of each other, is a hydrogen atom, a halogen atom, a ($C_1$–$C_6$) alkyl group, a ($C_2$–$C_6$) alkenyl group, a ($C_2$–$C_6$) alkynyl group, a ($C_3$–$C_6$) cycloalkyl group, a ($C_1$–$C_4$) haloalkyl group, a ($C_1$–$C_6$) alkoxy group, a ($C_2$–$C_6$) alkenyloxy group, a ($C_2$–$C_6$) alkynyloxy group, a ($C_3$–$C_6$) cycloalkoxy group, a ($C_1$–$C_4$) haloalkoxy group, a cyano ($C_1$–$C_4$) alkyloxy group, a ($C_1$–$C_4$) alkoxy ($C_1$–$C_4$) alkyloxy group, a ($C_3$–$C_6$) cycloalkyl ($C_1$–$C_4$) alkoxy group, a benzyloxy group [said group may be substituted by a halogen atom, a ($C_1$–$C_4$) alkyl group or a ($C_1$–$C_4$) alkoxy group], a ($C_1$–$C_6$) alkylthio group, a ($C_1$–$C_4$) alkoxy ($C_1$–$C_4$) alkyl group, a ($C_1$–$C_4$) alkylcarbonyl group, a formyl group, a phenyl group, a cyano group or a ($C_1$–$C_6$) alkylsulfonyl group, $R^3$ is a hydrogen atom, a ($C_1$–$C_6$) alkyl group, a ($C_1$–$C_6$) alkoxy group or a halogen atom, X is a hydrogen atom, a halogen atom, a nitro group, a ($C_1$–$C_6$) alkyl group, a ($C_2$–$C_6$) alkynyl group, a ($C_3$–$C_6$) cycloalkyl group, a benzyl group [said group may be substituted by a halogen atom, a ($C_1$–$C_4$) alkyl group or a ($C_1$–$C_4$) alkoxy group], a ($C_1$–$C_6$) alkoxy group, a ($C_2$–$C_6$) alkenyloxy group, a ($C_2$–$C_6$) alkynyloxy group, a ($C_1$–$C_6$) alkylthio group, a ($C_1$–$C_6$) alkylsulfonyl group, a phenoxy group, a ($C_1$–$C_4$) alkoxy ($C_1$–$C_4$) alkyl group, a ($C_1$–$C_4$) haloalkyl group, a ($C_1$–$C_4$) haloalkoxy group, a ($C_1$–$C_4$) alkylcarbonyl group, a ($C_1$–$C_4$) alkoxycarbonyl group, an amino group, a mono ($C_1$–$C_4$) alkylamino group, a di($C_1$–$C_4$) alkylamino group, an anilino group or a phenyl group [said group may be substituted by a halogen atom, a ($C_1$–$C_4$) alkyl group or a ($C_1$–$C_4$) alkoxy group], Y is a halogen atom, a nitro group, a cyano group, a ($C_1$–$C_6$) alkyl group, a ($C_2$–$C_6$) alkenyl group, a ($C_2$–$C_6$) alkynyl group, a ($C_1$–$C_6$) alkoxy group, a ($C_2$–$C_6$) alkenyloxy group, a ($C_2$–$C_6$) alkynyloxy group, a ($C_1$–$C_4$) haloalkoxy group, a ($C_1$–$C_6$) alkylthio group, a ($C_1$–$C_4$) alkoxy ($C_1$–$C_4$) alkyl group, a ($C_1$–$C_4$) haloalkyl group, a ($C_1$–$C_4$) alkylcarbonyl group, a ($C_1$–$C_4$) alkoxycarbonyl group, a benzoyl group, an amino group, a mono ($C_1$–$C_4$) alkylamino group, a di($C_1$–$C_4$) alkylamino group, a phenyl group [said group may be substituted by a halogen atom, a ($C_1$–$C_4$) alkyl group or a ($C_1$–$C_4$) alkoxy group] or a phenoxy group [said group may be substituted by a halogen atom, a ($C_1$–$C_4$) alkyl group or a ($C_1$–$C_4$) alkoxy group], and n is 0 or an integer of from 1 to 3.

5. An agricultural/horticultural fungicidal composition containing the pyrimidinylbenzimidazole compound as defined in claim 4, as the active ingredient and an agriculturally/horticulturally acceptable inert component.

* * * * *